(12) United States Patent
Brady et al.

(10) Patent No.: US 11,065,107 B2
(45) Date of Patent: *Jul. 20, 2021

(54) ACCOMMODATING INTRAOCULAR LENS DEVICE

(71) Applicant: LensGen, Inc., Irvine, CA (US)

(72) Inventors: Daniel Brady, Irvine, CA (US);
Thomas Silvestrini, Alamo, CA (US);
Ramgopal Rao, Irvine, CA (US)

(73) Assignee: LensGen, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,188

(22) Filed: Jun. 1, 2018

(65) Prior Publication Data
US 2018/0271645 A1 Sep. 27, 2018

Related U.S. Application Data

(63) Continuation of application No. PCT/US2016/064491, filed on Dec. 1, 2016.
(Continued)

(51) Int. Cl.
*A61F 2/16* (2006.01)
*B29D 11/02* (2006.01)
(Continued)

(52) U.S. Cl.
CPC .............. *A61F 2/16* (2013.01); *A61F 2/1624* (2013.01); *A61F 2/1648* (2013.01);
(Continued)

(58) Field of Classification Search
CPC ........ A61F 2/16; A61F 2/1624; A61F 2/1629; A61F 2/1635; A61F 2/1648;
(Continued)

(56) References Cited

U.S. PATENT DOCUMENTS 4,032,502 A 6/1977 Lee et al.
4,373,218 A 2/1983 Schachar
(Continued)

FOREIGN PATENT DOCUMENTS

DE 20 2010 003217 U1 8/2011
EP 0356050 A1 2/1990
(Continued)

OTHER PUBLICATIONS

International Search Report and Written Opinion dated Apr. 20, 2017 for PCT/US2016/064491 (14 pages).
(Continued)

*Primary Examiner* — Leslie Lopez
(74) *Attorney, Agent, or Firm* — Knobbe, Martens, Olson & Bear LLP

(57) ABSTRACT

An accommodating intraocular lens device is provided. The accommodating intraocular lens device comprises a base assembly and a power lens. The base assembly comprises a first open end, a second end coupled to a base lens, and a haptic surrounding a central cavity. The haptic may comprise an outer periphery, an inner surface and a height between a first edge and a second edge. The power lens is configured to fit within the central cavity. The power lens may comprise a first side, a second side, a peripheral edge coupling the first and second sides, and a closed cavity configured to house a fluid. The first side of the power lens may be positioned at a predetermined distance from the first edge of the haptic.

23 Claims, 48 Drawing Sheets

Related U.S. Application Data

(60) Provisional application No. 62/261,790, filed on Dec. 1, 2015.

(51) Int. Cl.
   *G02C 7/08* (2006.01)
   *G02C 7/04* (2006.01)
   *A61F 9/007* (2006.01)
   *G02B 3/14* (2006.01)

(52) U.S. Cl.
   CPC .......... *A61F 9/00736* (2013.01); *B29D 11/02* (2013.01); *B29D 11/026* (2013.01); *G02C 7/04* (2013.01); *G02C 7/08* (2013.01); *A61F 2002/169* (2015.04); *A61F 2002/1681* (2013.01); *A61F 2002/1682* (2015.04); *A61F 2220/0033* (2013.01); *G02B 3/14* (2013.01)

(58) Field of Classification Search
   CPC ...... A61F 2002/1681; A61F 2002/1682; A61F 2002/169; A61F 2002/16901; A61F 2002/16902
   See application file for complete search history.

(56) References Cited

U.S. PATENT DOCUMENTS

| | | |
|---|---|---|
| 4,512,040 A | 4/1985 | McClure |
| 4,585,457 A | 4/1986 | Kalb |
| 4,676,791 A | 6/1987 | LeMaster et al. |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,882,368 A | 11/1989 | Elias et al. |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,059,668 A | 10/1991 | Fukuda et al. |
| 5,074,876 A | 12/1991 | Kelman |
| 5,091,121 A | 2/1992 | Nakada et al. |
| 5,152,788 A | 10/1992 | Isaacson et al. |
| 5,167,883 A | 12/1992 | Takemasa et al. |
| 5,171,773 A | 12/1992 | Chaffe et al. |
| 5,227,447 A | 7/1993 | Sato et al. |
| 5,236,970 A | 8/1993 | Christ et al. |
| 5,264,522 A | 11/1993 | Mize et al. |
| 5,275,623 A | 1/1994 | Sarfarazi |
| 5,278,258 A | 1/1994 | Gerace et al. |
| 5,312,860 A | 5/1994 | Mize et al. |
| 5,326,506 A | 7/1994 | Vanderbilt |
| 5,336,487 A | 8/1994 | Refojo et al. |
| 5,443,506 A | 8/1995 | Garabet |
| 5,447,987 A | 9/1995 | Sato et al. |
| 5,489,302 A | 2/1996 | Skottun |
| 5,583,178 A | 12/1996 | Oxman et al. |
| 5,607,472 A | 3/1997 | Thompson |
| 5,665,794 A | 9/1997 | Maxson et al. |
| 5,854,310 A | 12/1998 | Maxson |
| 6,071,439 A | 6/2000 | Bawa et al. |
| 6,117,171 A | 9/2000 | Skottun |
| 6,197,057 B1 | 3/2001 | Peyman et al. |
| 6,361,561 B1 | 3/2002 | Huo et al. |
| 6,551,354 B1 | 4/2003 | Ghazizadeh et al. |
| 6,616,691 B1 | 9/2003 | Tran |
| 6,695,881 B2 | 2/2004 | Peng et al. |
| 6,730,123 B1 | 5/2004 | Klopotek |
| 6,836,374 B2 | 12/2004 | Esch et al. |
| 6,855,164 B2 | 2/2005 | Glazier |
| 6,858,040 B2 | 2/2005 | Nguyen et al. |
| 6,860,601 B2 | 3/2005 | Shadduck |
| 6,926,736 B2 | 8/2005 | Peng et al. |
| 6,930,838 B2 | 8/2005 | Schachar |
| 6,935,743 B2 | 8/2005 | Shadduck |
| 6,966,649 B2 | 11/2005 | Shadduck |
| 6,969,403 B2 | 11/2005 | Peng et al. |
| 7,041,134 B2 | 5/2006 | Nguyen et al. |
| 7,063,723 B2 | 6/2006 | Ran |
| 7,068,439 B2 | 6/2006 | Esch et al. |
| 7,122,053 B2 | 10/2006 | Esch |
| 7,150,760 B2 | 12/2006 | Zhang |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,316,713 B2 | 1/2008 | Zhang |
| 7,416,562 B2 | 8/2008 | Gross |
| 7,438,723 B2 | 10/2008 | Esch |
| 7,452,377 B2 | 11/2008 | Watling et al. |
| 7,453,646 B2 | 11/2008 | Lo |
| 7,485,144 B2 | 2/2009 | Esch |
| 7,591,849 B2 | 9/2009 | Richardson |
| 7,637,947 B2 | 12/2009 | Smith et al. |
| 7,662,179 B2 | 2/2010 | Sarfarazi |
| 7,675,686 B2 | 3/2010 | Lo et al. |
| 7,753,953 B1 | 7/2010 | Yee |
| 7,776,088 B2 | 8/2010 | Shadduck |
| 7,780,729 B2 | 8/2010 | Nguyen et al. |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,986,465 B1 | 7/2011 | Lo et al. |
| 7,998,198 B2 | 8/2011 | Angelopoulos et al. |
| 7,998,199 B2 | 8/2011 | Nun |
| 8,012,204 B2 | 9/2011 | Weinschenk, III et al. |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,062,361 B2 | 11/2011 | Nguyen et al. |
| 8,070,806 B2 | 12/2011 | Khoury |
| 8,158,712 B2 | 4/2012 | Your |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,216,306 B2 | 7/2012 | Coroneo |
| 8,246,679 B2 | 8/2012 | Nguyen et al. |
| 8,254,034 B1 | 8/2012 | Shields et al. |
| 8,257,827 B1 | 9/2012 | Shi et al. |
| 8,273,123 B2 | 9/2012 | Nun |
| 8,303,656 B2 | 11/2012 | Shadduck |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,377,124 B2 | 2/2013 | Hong et al. |
| 8,398,709 B2 | 3/2013 | Nun |
| 8,414,646 B2 | 4/2013 | De Juan, Jr. et al. |
| 8,425,597 B2 | 4/2013 | Glick et al. |
| 8,425,599 B2 | 4/2013 | Shadduck |
| 8,430,928 B2 | 4/2013 | Liao |
| 8,447,086 B2 | 5/2013 | Hildebrand et al. |
| 8,454,688 B2 | 6/2013 | Esch et al. |
| 8,475,529 B2 | 7/2013 | Clarke |
| 8,496,701 B2 | 7/2013 | Hermans et al. |
| 8,500,806 B1 | 8/2013 | Phillips |
| 8,545,556 B2 | 10/2013 | Woods et al. |
| 8,579,972 B2 | 11/2013 | Rombach |
| 8,585,758 B2 | 11/2013 | Woods |
| 8,608,799 B2 | 12/2013 | Blake |
| 8,608,800 B2 | 12/2013 | Portney |

(56) References Cited

U.S. PATENT DOCUMENTS

| | | |
|---|---|---|
| 8,613,766 B2 | 12/2013 | Richardson et al. |
| 8,647,384 B2 | 2/2014 | Lu |
| 8,657,878 B2 | 2/2014 | Mentak et al. |
| 8,668,734 B2 | 3/2014 | Hildebrand et al. |
| 8,690,942 B2 | 3/2014 | Hildebrand et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,858,626 B2 | 10/2014 | Noy |
| 8,867,141 B2 | 10/2014 | Pugh et al. |
| 8,900,298 B2 | 12/2014 | Anvar et al. |
| 8,900,300 B1 | 12/2014 | Wortz |
| 8,956,408 B2 | 2/2015 | Smiley et al. |
| 8,968,396 B2 | 3/2015 | Matthews et al. |
| 8,968,399 B2 | 3/2015 | Ghabra |
| 8,992,609 B2 | 3/2015 | Shadduck |
| 9,005,282 B2 | 4/2015 | Chang et al. |
| 9,005,283 B2 | 4/2015 | Nguyen et al. |
| 9,034,035 B2 | 5/2015 | Betser et al. |
| 9,044,317 B2 | 6/2015 | Hildebrand et al. |
| 9,072,600 B2 | 7/2015 | Tran |
| 9,090,033 B2 | 7/2015 | Carson et al. |
| 9,095,424 B2 | 8/2015 | Kahook et al. |
| 9,125,736 B2 | 9/2015 | Kahook et al. |
| 9,186,244 B2 | 11/2015 | Silvestrini et al. |
| 9,198,752 B2 | 12/2015 | Woods |
| 9,277,987 B2 | 3/2016 | Smiley et al. |
| 9,277,988 B1 | 3/2016 | Chu |
| 9,289,287 B2 | 3/2016 | Kahook et al. |
| 9,326,846 B2 | 5/2016 | Devita Gerardi et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,421,088 B1 | 8/2016 | Kahook et al. |
| 9,427,312 B2 | 8/2016 | DeBoer et al. |
| 9,433,497 B2 | 9/2016 | DeBoer et al. |
| 9,456,895 B2 | 10/2016 | Shadduck |
| 9,486,311 B2 | 11/2016 | Argento et al. |
| 9,610,155 B2 | 4/2017 | Matthews |
| 9,622,852 B2 | 4/2017 | Simonov et al. |
| 9,629,712 B2 | 4/2017 | Stenger |
| 9,636,213 B2 | 5/2017 | Brady |
| 9,655,716 B2 | 5/2017 | Cumming |
| 9,681,946 B2 | 6/2017 | Kahook et al. |
| 9,693,858 B2 | 7/2017 | Hildebrand et al. |
| 9,713,526 B2 | 7/2017 | Rombach |
| 9,713,527 B2 | 7/2017 | Nishi et al. |
| 9,717,589 B2 | 8/2017 | Simonov et al. |
| 9,744,027 B2 | 8/2017 | Jansen |
| 9,744,028 B2 | 8/2017 | Simonov et al. |
| 9,795,473 B2 | 10/2017 | Smiley et al. |
| 9,808,339 B2 | 11/2017 | Dorronsoro Diaz et al. |
| 9,814,568 B2 | 11/2017 | Ben Nun |
| 9,814,570 B2 | 11/2017 | Robert et al. |
| 9,820,849 B2 | 11/2017 | Jansen |
| 9,848,980 B2 | 12/2017 | McCafferty |
| 9,855,137 B2 | 1/2018 | Smiley et al. |
| 9,855,139 B2 | 1/2018 | Matthews et al. |
| 9,861,469 B2 | 1/2018 | Simonov et al. |
| 9,872,762 B2 | 1/2018 | Scholl et al. |
| 9,872,763 B2 | 1/2018 | Smiley et al. |
| 9,877,825 B2 | 1/2018 | Kahook et al. |
| 9,883,940 B2 | 2/2018 | Nishi et al. |
| 9,925,039 B2 | 3/2018 | Sohn et al. |
| 9,925,040 B2 | 3/2018 | Kahook et al. |
| 9,931,202 B2 | 4/2018 | Borja et al. |
| 9,987,126 B2 | 6/2018 | Borja et al. |
| 10,004,596 B2 | 6/2018 | Brady et al. |
| 10,028,824 B2 | 7/2018 | Kahook et al. |
| 10,045,844 B2 | 8/2018 | Smiley et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 10,195,018 B2 | 2/2019 | Salahieh et al. |
| 10,195,020 B2 | 2/2019 | Matthews |
| 10,647,831 B2 | 5/2020 | Silvestrini et al. |
| 10,772,721 B2 | 9/2020 | Rao et al. |
| 10,842,616 B2 | 11/2020 | Silvestrini et al. |
| 2002/0005344 A1 | 1/2002 | Heidlas et al. |
| 2002/0055776 A1 | 5/2002 | Juan, Jr. et al. |
| 2002/0071856 A1 | 6/2002 | Dillingham et al. |
| 2002/0120329 A1 | 8/2002 | Lang et al. |
| 2003/0093149 A1 | 5/2003 | Glazier |
| 2003/0105522 A1 | 6/2003 | Glazier |
| 2003/0109926 A1 | 6/2003 | Portney |
| 2003/0158295 A1 | 8/2003 | Fukuda et al. |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0162612 A1 | 8/2004 | Portney et al. |
| 2004/0169816 A1 | 9/2004 | Esch |
| 2004/0249455 A1 | 12/2004 | Tran |
| 2005/0021139 A1 | 1/2005 | Shadduck |
| 2005/0071002 A1 | 3/2005 | Glazier |
| 2005/0107873 A1 | 5/2005 | Zhou |
| 2005/0137703 A1 | 6/2005 | Chen |
| 2005/0251253 A1 | 11/2005 | Gross |
| 2005/0251254 A1 | 11/2005 | Brady et al. |
| 2005/0267575 A1 | 12/2005 | Nguyen et al. |
| 2006/0041307 A1 | 2/2006 | Esch et al. |
| 2006/0047339 A1 | 3/2006 | Brown |
| 2006/0069178 A1 | 3/2006 | Rastogi et al. |
| 2006/0074487 A1 | 4/2006 | Gilg |
| 2006/0111776 A1 | 5/2006 | Glick et al. |
| 2006/0134173 A1 | 6/2006 | Liu et al. |
| 2006/0135477 A1 | 6/2006 | Haitjema et al. |
| 2006/0212116 A1 | 9/2006 | Woods |
| 2006/0238702 A1 | 10/2006 | Glick et al. |
| 2006/0241752 A1 | 10/2006 | Israel |
| 2007/0016293 A1 | 1/2007 | Tran |
| 2007/0032868 A1 | 2/2007 | Woods et al. |
| 2007/0050024 A1 | 3/2007 | Zhang |
| 2007/0050025 A1 | 3/2007 | Nguyen et al. |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0132949 A1 | 6/2007 | Phelan |
| 2007/0213817 A1 | 9/2007 | Esch et al. |
| 2007/0260308 A1 | 11/2007 | Tran |
| 2007/0260310 A1 | 11/2007 | Richardson |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0046077 A1 | 2/2008 | Cumming |
| 2008/0051886 A1 | 2/2008 | Lin |
| 2008/0154364 A1 | 6/2008 | Richardson et al. |
| 2008/0200982 A1 | 8/2008 | Your |
| 2008/0269887 A1 | 10/2008 | Cumming |
| 2008/0300680 A1 | 12/2008 | Nun |
| 2008/0306587 A1 | 12/2008 | Your |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0043384 A1 | 2/2009 | Niwa et al. |
| 2009/0116118 A1 | 5/2009 | Frazier et al. |
| 2009/0125106 A1 | 5/2009 | Weinschenk, III et al. |
| 2009/0149952 A1 | 6/2009 | Shadduck |
| 2009/0198326 A1 | 8/2009 | Zhou et al. |
| 2009/0204209 A1 | 8/2009 | Tran |
| 2009/0204210 A1 | 8/2009 | Pynson |
| 2009/0264998 A1 | 10/2009 | Mentak et al. |

(56) References Cited

U.S. PATENT DOCUMENTS

| | | |
|---|---|---|
| 2009/0292355 A1 | 11/2009 | Boyd et al. |
| 2009/0319040 A1 | 12/2009 | Khoury |
| 2010/0004742 A1 | 1/2010 | Cumming |
| 2010/0055449 A1 | 3/2010 | Ota |
| 2010/0057095 A1 | 3/2010 | Khuray et al. |
| 2010/0094412 A1 | 4/2010 | Wensrich |
| 2010/0094413 A1 | 4/2010 | Rombach et al. |
| 2010/0131058 A1 | 5/2010 | Shadduck |
| 2010/0131059 A1 | 5/2010 | Callahan et al. |
| 2010/0179653 A1* | 7/2010 | Argento ............ A61F 2/1635 623/6.13 |
| 2010/0204787 A1 | 8/2010 | Noy |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0118834 A1 | 5/2011 | Lo et al. |
| 2011/0118836 A1 | 5/2011 | Jain |
| 2011/0208301 A1 | 8/2011 | Anvar et al. |
| 2011/0224788 A1 | 9/2011 | Webb |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078364 A1 | 3/2012 | Stenger |
| 2012/0095125 A1 | 4/2012 | Hu et al. |
| 2012/0232649 A1 | 9/2012 | Cuevas |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0035760 A1 | 2/2013 | Portney |
| 2013/0038944 A1 | 2/2013 | Chang et al. |
| 2013/0060331 A1 | 3/2013 | Shadduck |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0142558 A1 | 5/2014 | Culbertson et al. |
| 2014/0172092 A1 | 6/2014 | Carson et al. |
| 2014/0180404 A1 | 6/2014 | Tram |
| 2014/0180405 A1 | 6/2014 | Weinschenk, III et al. |
| 2014/0180406 A1 | 6/2014 | Simpson |
| 2014/0180407 A1* | 6/2014 | Sohn ............ A61F 2/1648 623/6.15 |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0309734 A1 | 10/2014 | Sohn et al. |
| 2015/0087743 A1 | 3/2015 | Anvar et al. |
| 2015/0105760 A1 | 4/2015 | Rao et al. |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0238310 A1 | 8/2015 | Matthews et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1 | 3/2016 | Salahieh et al. |
| 2016/0074154 A1 | 3/2016 | Woods |
| 2016/0184089 A1 | 6/2016 | Dudee et al. |
| 2016/0184092 A1 | 6/2016 | Smiley et al. |
| 2016/0208138 A1 | 7/2016 | Nishijima et al. |
| 2016/0256265 A1 | 9/2016 | Borja et al. |
| 2016/0262875 A1 | 9/2016 | Smith et al. |
| 2016/0281019 A1 | 9/2016 | Deklippel et al. |
| 2016/0287380 A1 | 10/2016 | Shi et al. |
| 2016/0317287 A1 | 11/2016 | Silvestrini et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0216021 A1 | 8/2017 | Brady |
| 2017/0247525 A1 | 8/2017 | Silverstrini et al. |
| 2017/0290658 A1 | 10/2017 | Hildebrand et al. |
| 2017/0319332 A1 | 11/2017 | Kahook et al. |
| 2017/0342096 A1 | 11/2017 | Silvestrini |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0256315 A1 | 9/2018 | Hildebrand et al. |
| 2018/0271642 A1 | 9/2018 | Wortz et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0000612 A1 | 1/2019 | Rao et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076243 A1 | 3/2019 | Hadba et al. |
| 2019/0083235 A1 | 3/2019 | Wortz |
| 2019/0099263 A1 | 4/2019 | Brady et al. |
| 2019/0374334 A1 | 12/2019 | Brady et al. |
| 2020/0369853 A1 | 11/2020 | Silvestrini et al. |

FOREIGN PATENT DOCUMENTS

| | | |
|---|---|---|
| EP | 0766540 B1 | 8/1999 |
| EP | 1881818 B1 | 7/2015 |
| JP | H09-150002 A | 6/1997 |
| JP | 2005-511201 | 4/2005 |
| JP | 2006-511245 | 4/2006 |
| JP | 2006-516002 | 6/2006 |
| JP | 2010-514507 | 5/2010 |
| JP | 2013-047290 | 3/2013 |
| WO | WO 92/17132 | 10/1992 |
| WO | WO 99/29266 | 6/1999 |
| WO | WO 1999/056670 | 11/1999 |
| WO | WO 2000/021467 | 4/2000 |
| WO | WO 2001/034067 | 5/2001 |

(56) References Cited

FOREIGN PATENT DOCUMENTS

| | | |
|---|---|---|
| WO | WO 2004/037127 | 5/2004 |
| WO | WO 2004/052242 | 6/2004 |
| WO | WO 2004/054471 | 7/2004 |
| WO | WO 2004/072689 | 8/2004 |
| WO | WO 2006/047383 | 5/2006 |
| WO | WO 2007/005778 | 1/2007 |
| WO | WO 2007/047529 | 4/2007 |
| WO | WO 2007/047530 | 4/2007 |
| WO | WO 2008/024766 | 2/2008 |
| WO | WO 2008/031231 | 3/2008 |
| WO | WO 2008/077040 | 6/2008 |
| WO | WO 2008/082957 | 7/2008 |
| WO | WO 2008/103798 | 8/2008 |
| WO | WO 2009/015161 | 1/2009 |
| WO | WO 2009/015226 | 1/2009 |
| WO | WO 2009/015234 | 1/2009 |
| WO | WO 2009/015240 | 1/2009 |
| WO | WO 2009/064876 | 5/2009 |
| WO | WO 2010/010565 | 1/2010 |
| WO | WO 2010/081093 | 7/2010 |
| WO | WO 2011/026068 | 3/2011 |
| WO | WO 2011/106435 | 9/2011 |
| WO | WO 2011/137191 | 11/2011 |
| WO | WO 2012/006616 | 1/2012 |
| WO | WO 2012/129407 | 9/2012 |
| WO | WO 2013/016804 | 2/2013 |
| WO | WO 2013/070924 | 5/2013 |
| WO | WO 2013/142323 | 9/2013 |
| WO | WO 2013/166068 | 11/2013 |
| WO | WO 2013/180254 | 12/2013 |
| WO | WO 2013/190130 | 12/2013 |
| WO | WO 2014/099630 | 6/2014 |
| WO | WO 2014/145562 | 9/2014 |
| WO | WO 2014/152017 | 9/2014 |
| WO | WO 2014/197170 | 12/2014 |
| WO | WO 2015/066502 | 5/2015 |
| WO | WO 2015/066532 | 5/2015 |
| WO | WO 2015/126604 | 8/2015 |
| WO | WO 2016/018932 | 2/2016 |
| WO | WO 2016/033217 | 3/2016 |
| WO | WO 2016/122805 | 8/2016 |
| WO | WO 2016/201351 | 12/2016 |
| WO | WO 2017/079449 | 5/2017 |
| WO | WO 2017/079733 | 5/2017 |
| WO | WO 2017/087358 | 5/2017 |
| WO | WO 2017/096087 | 6/2017 |
| WO | WO 2017/192855 | 11/2017 |
| WO | WO 2018/081595 | 5/2018 |
| WO | WO 2018/119408 | 6/2018 |
| WO | WO 2018/167099 | 9/2018 |
| WO | WO 2018/222579 | 12/2018 |
| WO | WO 2018/227014 | 12/2018 |
| WO | WO 2019/005859 | 1/2019 |
| WO | WO 2019/027845 | 2/2019 |

OTHER PUBLICATIONS

Ehrmann, et al., "Biomechanical analysis of the accommodative apparatus in primates", Clinical and Experimental Optometry, May 2008, vol. 91, Issue 3, pp. 302-312.

Ehrmann, et al., "Ex Vivo Accommodation Simulator II—Concept and Preliminary Results", Proceedings of SPIE vol. 5314, Ophthalmic Technologies XIV, Jul. 2004, pp. 48-58.

Gabel, et al., "Silicone oil with high specific gravity for intraocular use", British Journal of Ophthalmology, Apr. 1987, vol. 71, 262-267.

Ghallagher-Wetmore, et al., "Supercritical fluid processing: a new dry technique for photoresist developing", SPIE's 1995 Symposium on Microlithography, 1995, vol. 2438, 16 pages.

Lane, et al., "Comparison of the biomechanical behavior of foldable intraocular lenses", Journal of Cataract Refract Surg, Nov. 2004, vol. 30, pp. 2397-2402.

Nakamura, et al., "Analysis and Fractionation of Silicone and Fluorosilicone Oils for Intraocular Use", Investigative Ophthalmology & Visual Science, vol. 31, No. 10, Oct. 1990, 2059-2069.

National Center for Biotechnology Information. PubChem Substance Database; SID=184590955, https://pubchem.ncbi.nlm.nih.gov/substance/184590955 (accessed Sep. 20, 2017).

Zhang, et al., "Fluidic adaptive lens with high focal length tunability", Applied Physics Letters, May 2003, vol. 82, No. 19, pp. 3171-3172.

Zhang, et al., "Integrated fluidic adaptive zoom lens", Optics Letters, Dec. 2004, vol. 29, No. 24, pp. 2855-2857.

Zhao, et al., "Strategies for Supercritical $CO_2$ Fractionation of Polydimethylsiloxane," Journal of Applied Polymer Science, 1995, vol. 55, 773-778.

Aliancy, et al., "Long-term capsule clarity with a disk-shaped intraocular lens", Journal of Cataract & Refractive Surgery, Apr. 2018, vol. 44, Issue 4, pp. 504-509.

Kramer, et al., "Prevention of postoperative capsular bag opacification using intraocular lenses and endocapsular devices maintaining an open or expanded capsular bag", Journal of Cataract & Refractive Surgery, Mar. 2016, vol. 42, Issue 3, pp. 469-484.

Leishman, et al., "Prevention of capsular bag opacification with a modified hydrophilic acrylic disk-shaped intraocular lens", Journal of Cataract & Refractive Surgery, Sep. 2012, vol. 38, Issue 9, pp. 1664-1670.

Response to Non-Final Rejection filed in U.S. Appl. No. 16/207,658, dated Sep. 14, 2020, in 14 pages.

Notice of Allowance issued in U.S. Appl. No. 16/207,658, dated Sep. 28, 2020 in 7 pages.

\* cited by examiner

ACCOMMODATING INTRAOCULAR LENS DEVICE

CROSS-REFERENCE TO RELATED APPLICATIONS

The present application is a continuation of International Patent Application No. PCT/US2016/064491, filed on Dec. 1, 2016, which in turn claims the benefit of U.S. Provisional Application No. 62/261,790, filed Dec. 1, 2015, the contents of which are incorporated herein by reference in their entireties into the present disclosure.

FIELD OF THE INVENTION

The invention relates generally to an accommodating intraocular lens device and, more particularly, to an accommodating intraocular lens device configured for implantation in a lens capsule or sulcus of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to increase as average life expectancies continue to rise. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lens. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

BRIEF SUMMARY

In one embodiment, an accommodating intraocular lens device having one of a high profile or a low profile. The accommodating intraocular lens device may comprise a base assembly and a power lens. The base assembly may comprise a first open end, a second end coupled to a base lens, and a haptic surrounding a central cavity. The haptic may comprise an outer periphery, an inner surface and a height between a first edge and a second edge. The power lens may comprise a first side, a second side, a peripheral edge coupling the first and second sides, and a closed cavity configured to house a fluid. The power lens may be configured to fit within the central cavity. The first side of the power lens may be positioned at a predetermined distance from the first edge of the haptic.

In one optional aspect, the accommodating intraocular lens may have a high profile, with the predetermined distance being in the range of about 0 mm to about 0.75 mm. In another optional aspect, the predetermined distance may be about 0.01% to about 37% of the height of the outer periphery.

In another optional aspect, the accommodating intraocular lens may have a low profile, with the predetermined distance being in the range of about 0.75 mm to about 1.5 mm. In a further optional aspect, the predetermined distance may be about 38% to about 75% of the height of the outer periphery.

In another optional aspect, the inner surface of the haptic may face the central cavity and the inner surface may comprise a plurality of spaced apart contact points configured to engage a portion of the peripheral edge of the power lens.

In another optional aspect, outer grooves may be provided to extend along at least a portion of the height of the haptic. The outer grooves may be configured to permit the haptic to be radially compressed, radially expanded, or both. The outer grooves may be disposed in the outer periphery opposite the inner surface contact points.

In another optional aspect, the haptic may further comprise a plurality of tabs extending radially inwardly into the cavity. The power lens may be secured to the base assembly by the plurality of tabs. In one aspect, the plurality of tabs comprise a bottom surface that is configured to contact the first side of the power lens. The bottom surface of the plurality of tabs may be positioned at a distance of about 0 mm to about 0.75 mm from the first edge of the haptic. The bottom surface of the tabs may also be provided at a distance, from the first edge of the haptic, of about 0.01% to about 37% of the height of the haptic. In another aspect, the bottom surface of the plurality of tabs may be positioned at a distance of about 0.75 mm to about 1 mm from the first edge of the haptic. The bottom surface of the tabs may also be provided at a distance, from the first edge of the haptic, of about 38% to about 75% of the height of the haptic.

In another optional aspect, the haptic may further comprise a plurality of tables extending radially inwardly into the cavity. A channel may be formed between the plurality of tabs and the plurality of tables to secure the power lens to the base assembly.

In another optional aspect, the accommodating intraocular lens device may further comprise a plurality of arms coupling the base lens to the haptic. The plurality of arms may vault the base lens away from the central cavity.

In another optional aspect, the first side of the power lens may comprise one of a flexible membrane and an optic and the second side of the power lens may comprise the other of the flexible membrane and the optic. The power lens may further comprise an optic coupler disposed from the peripheral edge to couple the optic to the peripheral edge. The optic coupler may be angled to vault the optic toward the flexible membrane.

In another optional aspect, the fluid contained in the closed cavity of the power lens may be one or a combination selected from the group consisting of: a silicone oil, a fluorinated silicone oil, a polyphenyl ether, and a fluorinated polyphenyl ether. The fluorinated polyphenyl ether may be one or a combination of a pentafluoro m-phenoxyphenyl ether and an m(pentafluorophenoxy)phenyl m-phenoxyphenyl ether.

In another embodiment, an accommodating intraocular lens device is provided. The accommodating intraocular lens device may comprise a base and a power lens. The base may comprise an outer portion, an inner portion and a closed space defined between the outer and inner portions. The closed space may comprise a reservoir configured to contain a fluid. The inner portion may circumscribe a substantially circular space. The power lens may comprise a flexible membrane on one side, an optic on the opposing side and a circumferential peripheral edge coupling the flexible membrane and the optic. A portion of the circumferential peripheral edge may be configured to be in facing relation to at least a portion of the inner portion of the base.

In one optional aspect, the base may be shaped as a ring.

In another optional aspect, the base may comprise a base lens.

In another optional aspect, the base may be shaped as an incomplete ring having two closed ends. The reservoir may extend around a portion of the circumference of the base at an arc degree of about 90 to about 350.

In another optional aspect, a thickness of the inner portion is less than a thickness of the outer portion.

In another optional aspect, the reservoir contains a fluid. The fluid may be any one or a combination selected from the group consisting of: a silicone oil, a fluorinated silicone oil, a polyphenyl ether, and a fluorinated polyphenyl ether. The fluorinated polyphenyl ether may be one or a combination of a pentafluoro m-phenoxyphenyl ether and an m(pentafluorophenoxy)phenyl m-phenoxyphenyl ether.

In another optional aspect, the power lens may further comprise a membrane coupler extending radially inwardly from the circumferential edge to couple the membrane with the peripheral edge.

In another optional aspect, the power lens may further comprise an optic coupler disposed from the circumferential peripheral edge to couple the optic to the peripheral edge. The optic coupler is angled to vault the optic toward the flexible membrane.

In another optional aspect, the base may further comprise upper and lower flanges extending radially inwardly and forming a channel adapted to accommodate the peripheral edge of the power lens.

In another optional aspect, the reservoir may comprise an outer reservoir, an inner reservoir and a narrowed channel between the outer and the inner reservoir. The inner reservoir may comprise a support structure or a braided structure.

In another optional aspect, the circumferential peripheral edge facing the inner portion of the base may be in direct physical contact with the inner portion.

In another optional aspect, the flexible membrane, the optic and the circumferential peripheral edge define a closed cavity within the power lens. The closed cavity may be configured to contain a fluid. The fluid may be any one or a combination selected from the group consisting of: a silicone oil, a fluorinated silicone oil, a polyphenyl ether, and a fluorinated polyphenyl ether. The fluorinated polyphenyl ether may be one or a combination of a pentafluoro m-phenoxyphenyl ether and an m(pentafluorophenoxy)phenyl m-phenoxyphenyl ether.

In another embodiment, a toric base assembly for an accommodating intraocular lens device is provided. The toric base assembly can be used as a part of a two-part accommodating intraocular lens device that further includes a power lens that can be provided in connection with the toric base assembly. The toric base assembly provides for an asymmetric translation of a radially compressive force onto a power lens that is provided centrally within the toric base assembly. The toric base assembly may thus comprise a base assembly comprising a base lens and a substantially circular haptic surrounding the base lens. The substantially circular haptic may have an outer periphery and at least one region in which the flexibility of the haptic is greater than the flexibility in remaining regions of the haptic. Application of a radially compressive force may result in an asymmetric deformation of the substantially circular haptic and the asymmetric deformation of the substantially circular haptic may provide a toric power change in one or both of the base lens and the power lens.

In one optional aspect, the at least one region may comprise two regions on opposing sides of the substantially circular haptic.

In another optional aspect, the greater structural flexibility may be provided by reducing a thickness of the at least one region.

In another optional aspect, the greater structural flexibility may be provided by forming one or more shaped cut-outs in the circular haptic in the at least one region.

In another optional aspect, the circular haptic may comprise at least one portion that extends radially outwardly of the outer periphery.

In another optional aspect, the circular haptic may comprise two portions that extend radially outwardly of the outer periphery. The two regions may be on opposing sides of the circular haptic.

In another optional aspect, in the at least one region, the substantially circular haptic may comprise at least one portion that extends radially outwardly of the outer periphery.

In another optional aspect, the accommodating intraocular lens device may further comprise one or more tabs extending radially inwardly from the outer periphery.

In another optional aspect, the accommodating intraocular lens device may further comprise a power lens configured to engage the circular haptic.

In another optional aspect, the asymmetric deformation of the substantially circular haptic provides a toric power change in both of the base lens and the power lens.

In another embodiment, an accommodating intraocular lens device may be provided with a retaining system that permits the power lens and the base assembly to couple or interlock. The accommodating intraocular lens device may comprise a base assembly comprising a first open end, a second end comprising a base lens, and a haptic surrounding the base lens. The haptic may comprise an outer periphery surrounding a cavity. A power lens may be sized to fit within the cavity and a retaining system may be provided to secure the power lens within the cavity.

In one optional aspect, the retaining system may comprise a plurality of tabs extending radially inwardly from the haptic and into the cavity.

In another optional aspect, the retaining system may comprise a plurality of fins extending from a peripheral edge of the power lens and a plurality of corresponding recesses defined within an inner periphery of the haptic. The plurality of recesses may each be defined by a raised portion and an entry passage on at least one side of the raised portion.

In another optional aspect, the retaining system may comprise a pair of flanges extending outwardly from a peripheral edge of the power lens and a channel. The channel may be formed in the inner periphery of the haptic. The channel may also be formed between a pair of opposing tabs extending from the inner periphery of the haptic.

In another optional aspect, the retaining system may comprise a plurality of tabs that extend radially inwardly from the first open end of the base assembly.

In another optional aspect, the haptic is substantially circular.

In another embodiment, an accommodating intraocular lens device is provided in which the power lens is attachable or attached to a base assembly. The accommodating intraocular lens device may comprise a base assembly and a power lens. The base assembly may comprise a first open end, an open second end, and a substantially circular haptic surrounding the base lens. The substantially circular haptic may comprise an outer periphery and an inner periphery facing a cavity. The power lens may be sized to fit within the cavity. The power lens may comprise a circumferential peripheral edge, wherein at least a portion of the circumferential peripheral edge may be engaged with the inner periphery of the substantially circular haptic.

In one optional aspect, the base assembly does not comprise an optic or lens in addition to the power lens.

In another optional aspect, a portion of the power lens may be attached to the substantially circular haptic. The portion of the power lens that is attached to the substantially circular haptic may be one or both of the circumferential peripheral edge or the posterior edge of the power lens.

In another optional aspect, the power lens may be attached to the substantially circular haptic by one or a combination selected from the group consisting of: bonding and insert-molding.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

Like numerals refer to like parts throughout the several views of the drawings.

DETAILED DESCRIPTION OF THE PREFERRED EMBODIMENTS

Figure 1A:
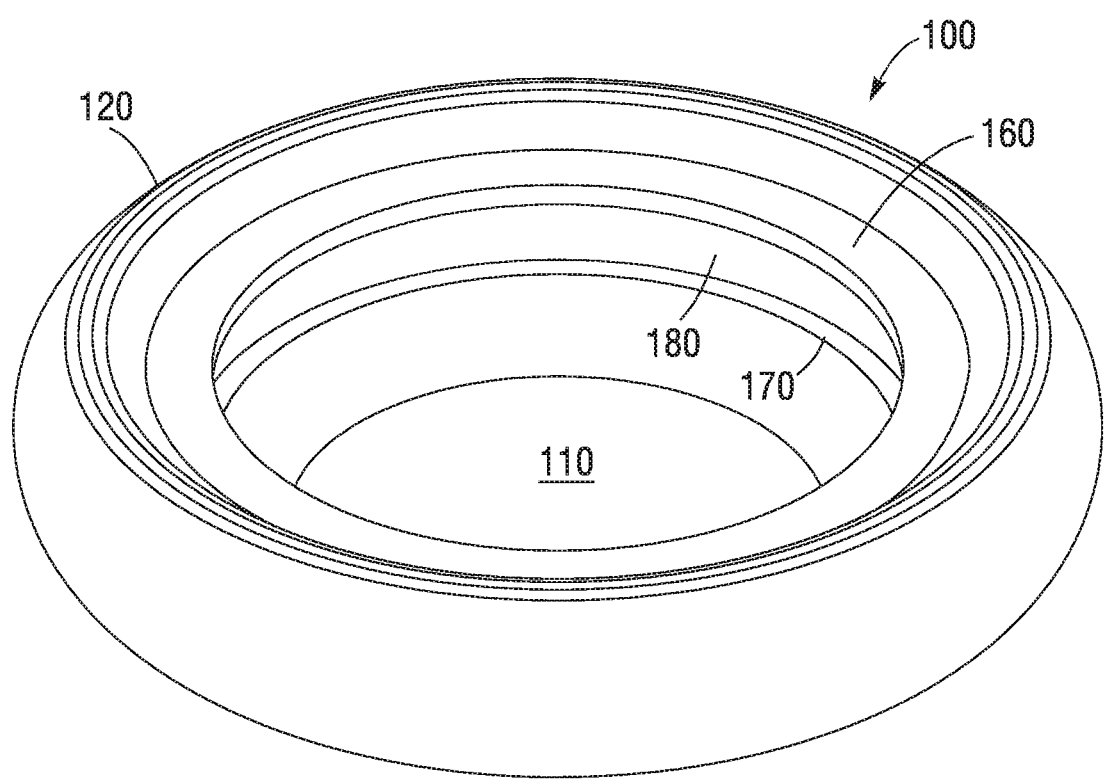
FIG. 1A depicts a perspective view of a fluid-filled base assembly, in accordance with an embodiment of the present disclosure.

Specific, non-limiting embodiments of the present invention will now be described with reference to the drawings. It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention.

Various embodiments of accommodating intraocular lenses (IOL) described herein and may comprise the power changing feature of a power lens in connection with a base lens. In one optional embodiment, the power changing feature of the IOL is driven by fluid optics within a closed volume of a power lens that comprises a flexible membrane and a lens or optic. One significant advantage of this embodiment is that the closed volume of the power lens that spaces apart the flexible membrane and the lens maintains a substantially constant volume and therefore avoids many of the problems associated with fluid optic IOLs that require substantial changes in volume, i.e., fluid being fed into the chamber from reservoirs. The many disadvantages exhibited by fluid optics having changing volumes include non-uniform power change and buckling. Certain embodiments of the IOLs and the power lens disclosed herein may avoid or mitigate such problems by maintaining a substantially constant volume, while at the same time maintaining good optical quality throughout the range of power change. Additionally, various embodiments of the IOLs that comprise a two-part assembly of the power lens and the base assembly as described herein provide a smaller delivery profile, a smaller implant profile or both, so as to require a substantially smaller incision size for implantation. This, in turn, may have the concomitant advantage of reducing biocompatibility issues associated with the delivery and implantation of larger IOLs and may result in faster healing and a more stable refraction.

The IOLs disclosed herein may be configured in any number of ways. Generally, the IOLs may comprise a base assembly and a power lens that can be coupled within the base assembly. In one embodiment, the radially compressive forces exerted on an implanted IOL may be concentrated onto a flexible membrane of the power lens to cause the flexible membrane to change in curvature. The lens or optic of the power lens may be configured to axially displace toward the flexible membrane in response to its change in curvature. This axial displacement may be facilitated by coupling the optic to the peripheral edge of the IOL in a manner that permits the optic to float. As the flexible membrane of the power lens changes in curvature, fluid adhesion or surface tension may pull the optic or lens of the power lens toward the flexible membrane. In another embodiment, the radially compressive forces exerted on the power lens may be concentrated onto the optic to cause the optic to axially displace and to push the flexible membrane in the same direction as the axial displacement of the optic to effectuate the change in curvature of the flexible membrane. In yet a further embodiment, the radially compressive forces on the power lens may be exerted on both the optic and the flexible membrane to cause the axial displacement and change in curvature, respectively.

In a further embodiment, the radially compressive forces exerted on the power lens may be applied to one or both of the flexible membrane and the optic to cause the change in curvature of the flexible membrane and to cause axial displacement of the optic toward the flexible membrane, while maintaining a constant volume during radial compression.

In one embodiment, the term "constant volume" includes a volume which changes no more than about 1% from its resting state, no more than about 2% from its resting state, no more than about 3% from its resting state, no more than about 4% from its resting state, no more than about 5% from its resting state, no more than about 10% from its resting state, no more than about 15% from its resting state, no more than about 20% from its resting state, no more than about 25% from its resting state, no more than about 30% from its resting state, no more than about 35% from its resting state, no more than about 40% from its resting state, no more than about 45% from its resting state, no more than about 50% from its resting state, no more than about 55% from its resting state, no more than about 60% from its resting state, no more than about 65% from its resting state, no more than about 70% from its resting state, and no more than about 75% from its resting state. In another embodiment, the term "constant volume" refers to a volume that changes in a range that includes and is between any two of the foregoing values. The term "resting state" describes the configuration of the IOL or power lens when no radially compressive forces are exerted on the IOL or the power lens.

As used herein, the term "power lens" may refer to an assembly that provides a range of accommodation or refractive correction in response to the application of radially compressive or expansive forces. In one embodiment, the power lens may provide a range of accommodation of about 1 diopter, about 2 diopters, about 3 diopters, about 4 diopters, about 5 diopters, about 6 diopters, about 7 diopters, about 8 diopters, about 9 diopters, about 10 diopters, about 11 diopters, about 12 diopters, about 13 diopters, about 14 diopters, about 15 diopters, about 16 diopters, about 17 diopters, about 18 diopters, about 19 diopters, or about 20 diopters. In another embodiment, the power lens may provide a range of accommodation between and including any two of the foregoing values. The term "power lens" may also include an assembly which comprises a first side, a second side, a peripheral edge coupling the first and second sides, and a closed cavity configured to house a fluid. In one aspect, the first and second sides may be a flexible membrane or an optic. In another aspect, the first side may be one of a flexible membrane or an optic and the second side may be the other of a flexible membrane or an optic. In a further aspect, the power lens may further be characterized as having a closed fluid-filled cavity having a constant volume throughout the range of accommodation.

Certain embodiments of the two-part accommodating IOL devices disclosed herein may provide a number of advantages owing to their separate two-part construction. Implantation of the two-part IOL device may require a significantly reduced incision size, as the two parts of the IOL device (e.g., the base assembly and the power lens) are implanted separately and thus significantly reducing the delivery profile for implantation. The reduced incision size may provide a number of advantages, including obviating the need for anesthesia and sutures to close the incision site and improved surgical outcomes. In one embodiment, the incision size required to implant the two-part accommodating IOL devices is less than about 5 mm, less than about 4 mm, less than about 3 mm, or less than about 2 mm. Stated a different way, each part of the two-part accommodating IOL device may be provided in a delivery state having a delivery profile that is less than about 5 mm, less than about 4 mm, less than about 3 mm, or less than about 2 mm. The delivery state of each part of the two-part accommodating IOL device may be provided when each part is rolled, folded or otherwise compressed to reduce its size for delivery. A hinge or a predetermined crease may be provided on one or both of the base assembly and the power lens to facilitate folding or rolling into the delivery state.

Additionally, greater control is afforded with respect to adjusting the sizing and the power of the IOL during surgery. Implanting the base assembly into the lens capsule will provide the physician an impression as to the size of the patient's lens capsule and will thus help select the correct size of the power changing lens that will subsequently be implanted into the base assembly.

Figure 1B:
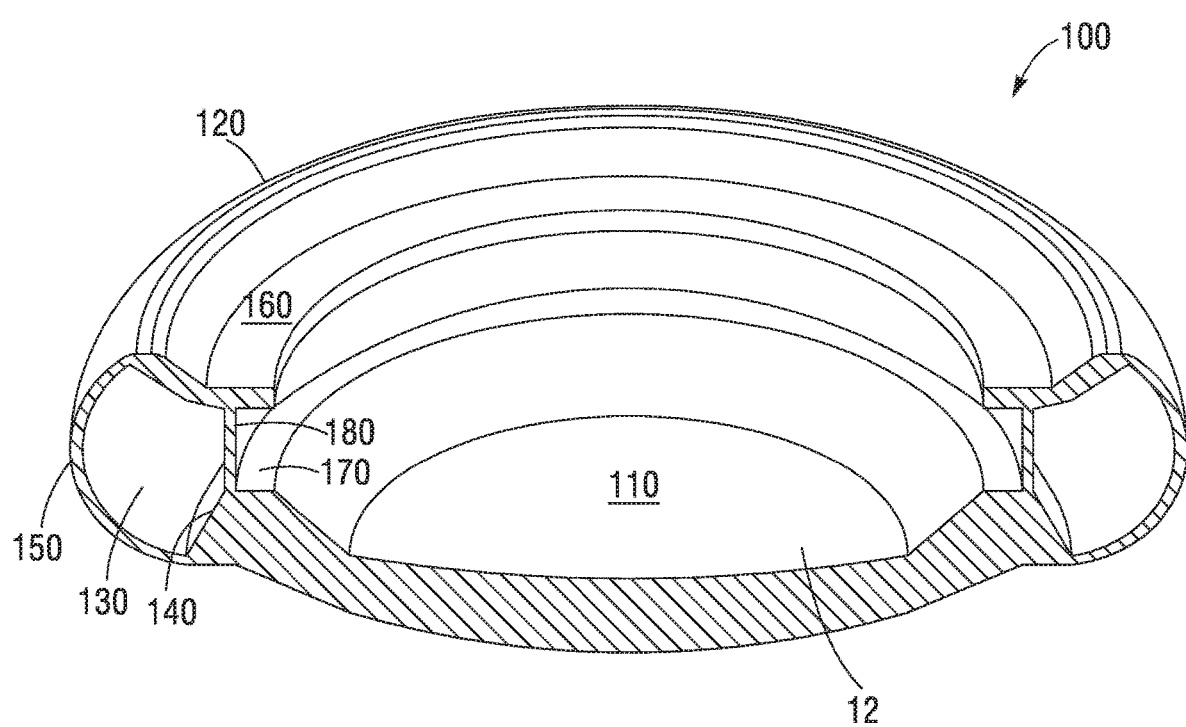
FIG. 1B depicts a cross-sectional view of the fluid-filled base assembly of FIG. 1A.

FIG. 1A depicts a perspective of an embodiment of a fluid-filled base assembly 100 of an accommodating IOL. FIG. 1B provides a cross-sectional view of the fluid-filled base assembly 100. The base assembly 100 shown in FIGS. 1A-1B may include a base lens 110 and a haptic system 120 disposed substantially circumferentially around the base lens 110. The haptic system 120 may be sized and configured to receive a separate power lens, such as the power lens 195, 350 depicted in FIGS. 1C and 3C respectively. The power lens 195, 350 can be inserted within the base assembly 100 to form a two-part accommodating IOL device.

In one embodiment, the haptic system 120 may include a reservoir 130 that extends through at least a portion of the haptic system 120. In accordance with one aspect, the reservoir 130 can extend around a portion of the circumference of the haptic system 120, as depicted in FIGS. 2A-2C and 4B, such that the reservoir 130 has an arc degree of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or about 360. In accordance with another aspect, the reservoir 130 can extend around a portion of the circumference of the haptic system 120 within a range that includes and is between any two of the foregoing values, e.g. 180 arc degrees to 270 arc degrees. In accordance with another aspect, the reservoir 130 can extend around an entire circumference of the haptic system 120, e.g., 360 arc degrees, as provided in the embodiment depicted in FIGS. 1A-1C.

Figure 1C:
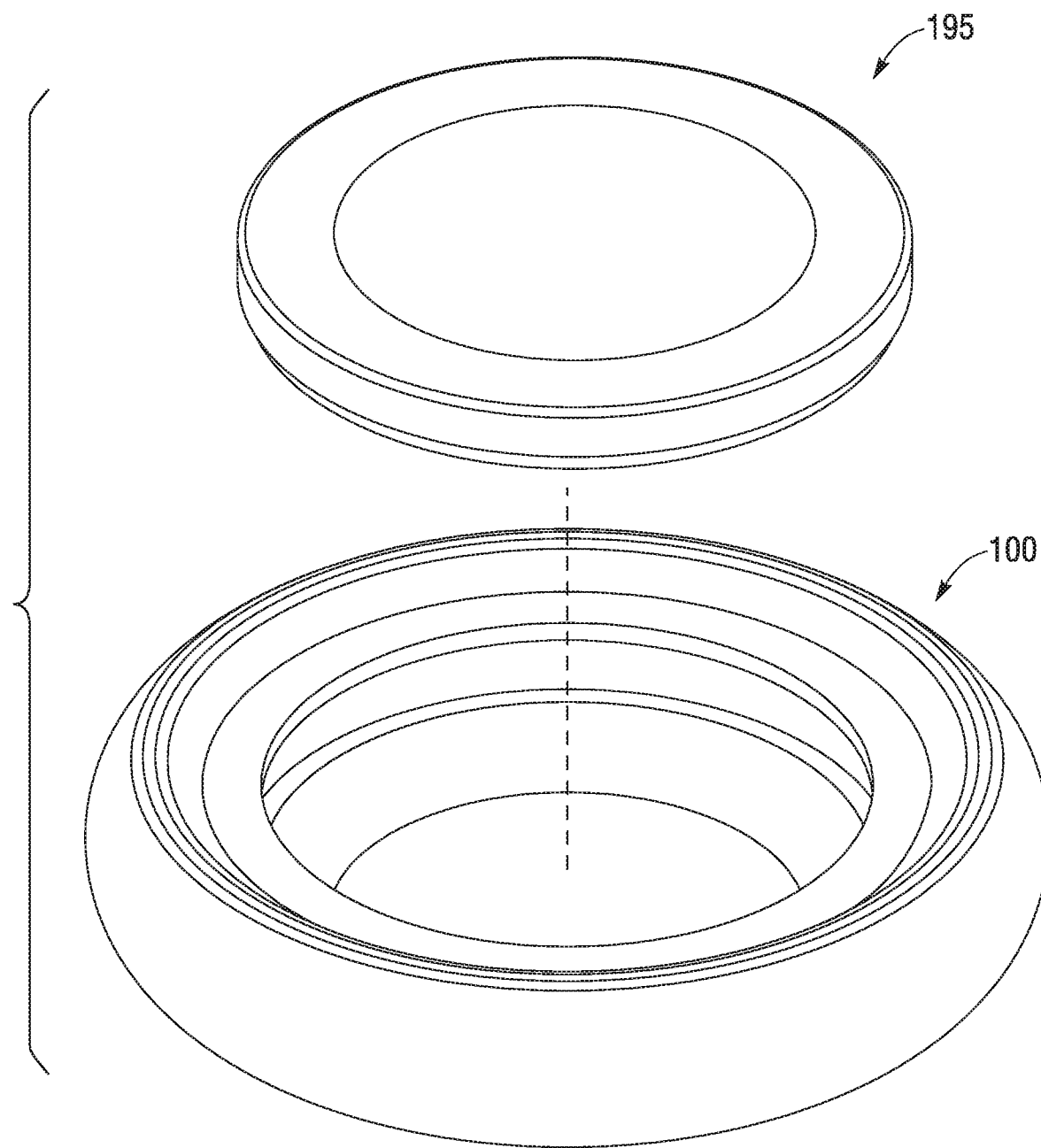
FIG. 1C depicts an exploded perspective view of a power lens being inserted into the fluid-filled base assembly of FIG. 1A.

The reservoir 130 can be defined or bounded by an inner region 180 and outer region 150. The reservoir 130 is configured to contain a fluid (e.g., a liquid or a gas). In certain embodiments, the fluid can be selected from the group consisting of: a silicone oil, a fluorinated silicone oil, a polyphenyl ether, and a fluorinated polyphenyl ether. The fluorinated polyphenyl ether may be one or a combination of a pentafluoro m-phenoxyphenyl ether and an m(pentafluorophenoxy)phenyl m-phenoxyphenyl ether. The fluid contained within the reservoir 130 can function to distribute forces applied to the outer region 150 of the haptic system 120 to the inner region 180. For example, fluid contained within the reservoir 130 can be used to substantially evenly transmit compressive forces applied to the outer region 150 of the haptic system 120, e.g. forces caused from the relaxation of the ciliary muscles, to the inner region 180. Forces transmitted to the inner region 180 can subsequently be transmitted to a power lens (195, 350 as depicted in FIGS. 1C and 3C respectively) that is coupled centrally within the base assembly 100. Alternatively or in addition, forces transmitted to the inner region 180 can be transmitted to the base lens 110.

The fluid-filled base assembly 100 can include an upper flange 160 and a lower flange 170 extending inwardly from the haptic system 120 along at least a portion of the circumference of the haptic system 120. The upper flange 160 and the lower flange 170 define a channel that is configured to secure a power lens 195 to the fluid-filled base assembly 100. FIG. 1C depicts an exploded perspective view of a power lens 195 being inserted into the base assembly 100, with the peripheral edge 197 of the power lens 195 being adapted to fit within the channel defined by the upper and lower flanges 160, 170. Additionally, at least a portion of the peripheral edge 197, if not the entirety of the peripheral edge 197 is configured to engage or directly contact the inner region 180 so as to effectively transmit the forces transmitted to the inner region 180 onto one or both of the first and second sides 196, 199 of the power lens 195 to provide accommodation. As explained above, the first and second sides may be a flexible membrane or an optic or, alternatively, the first side may be one of a flexible membrane or an optic and the second side may be the other of a flexible membrane or an optic.

Figure 2A:
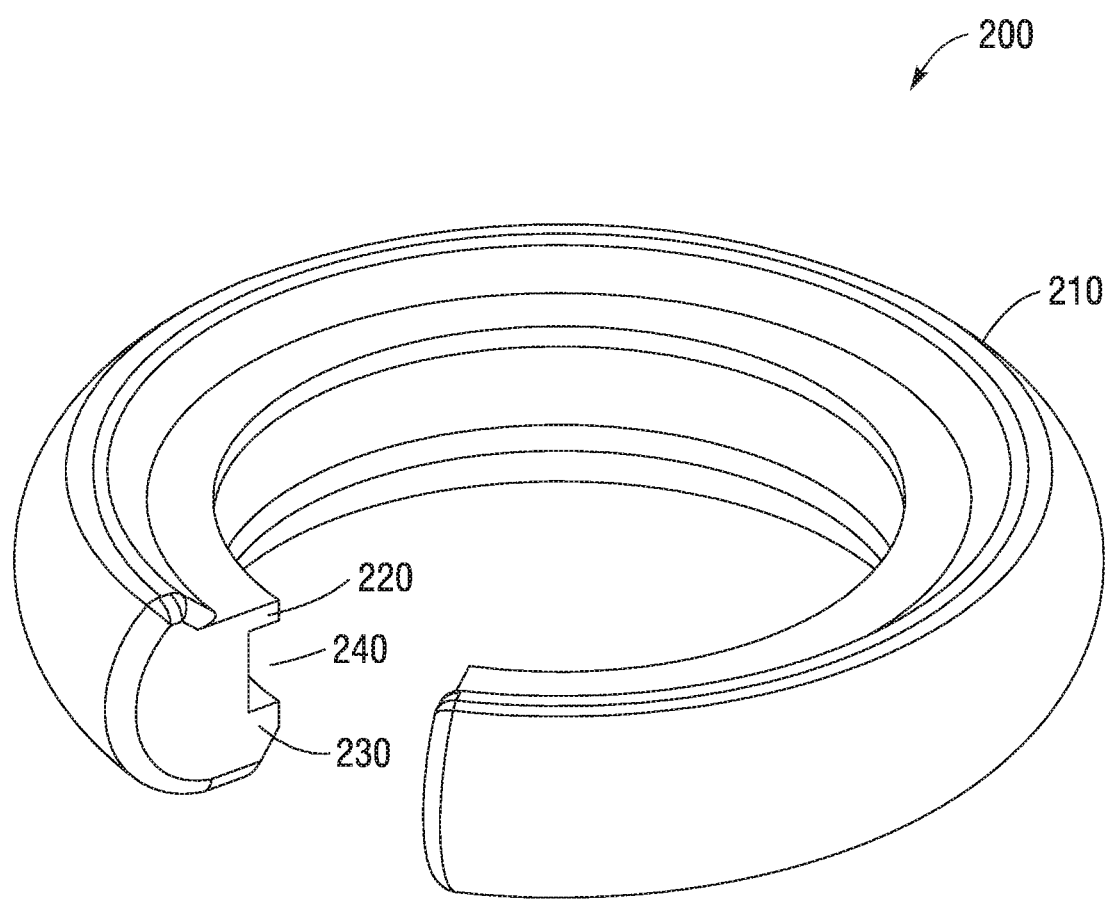
FIG. 2A depicts a perspective view of a fluid-filled open base ring, in accordance with an embodiment of the present disclosure.
Figure 2B:
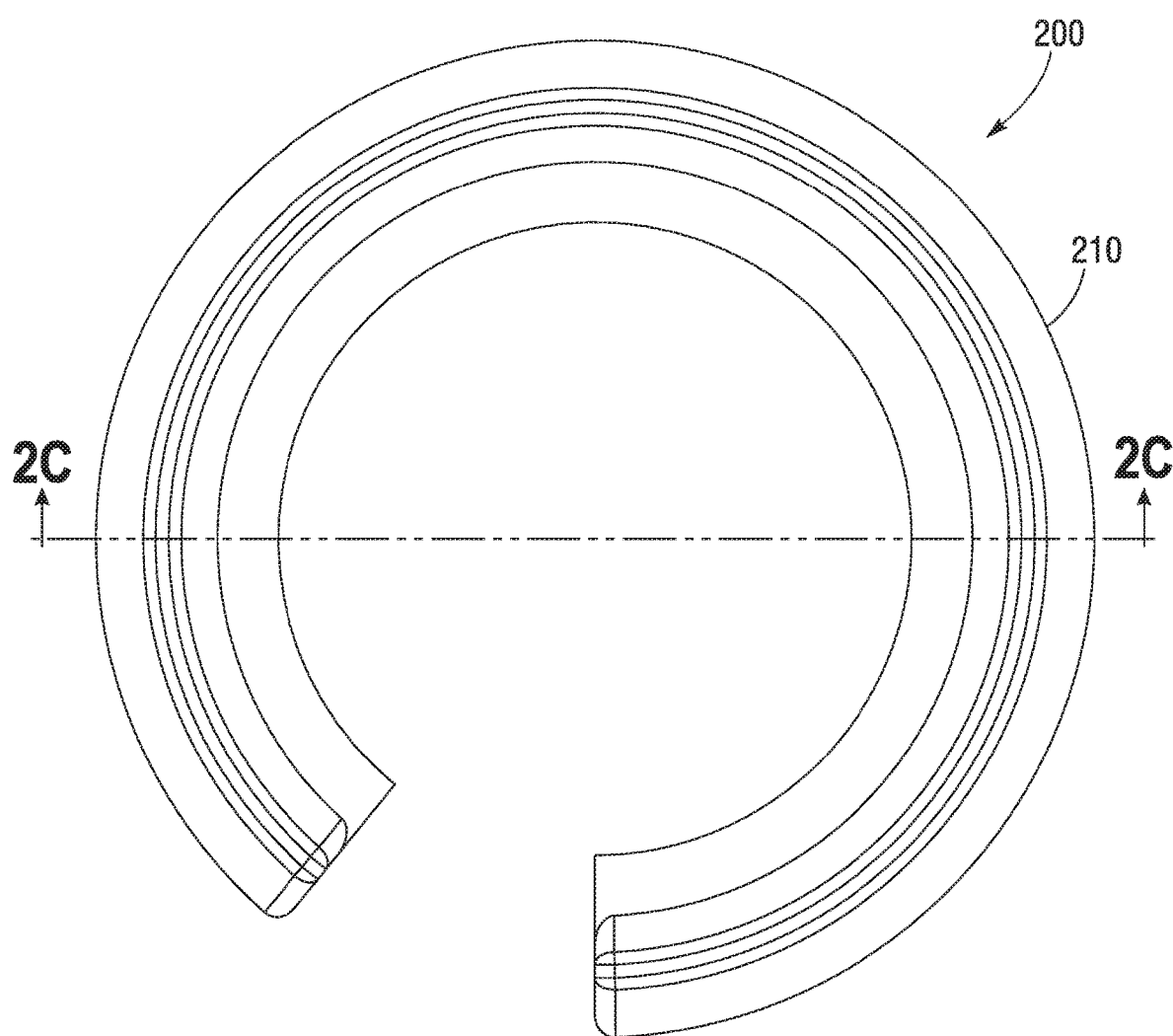
FIG. 2B depicts a top plan view of the fluid-filled open base ring of FIG. 2A.
Figure 2C:
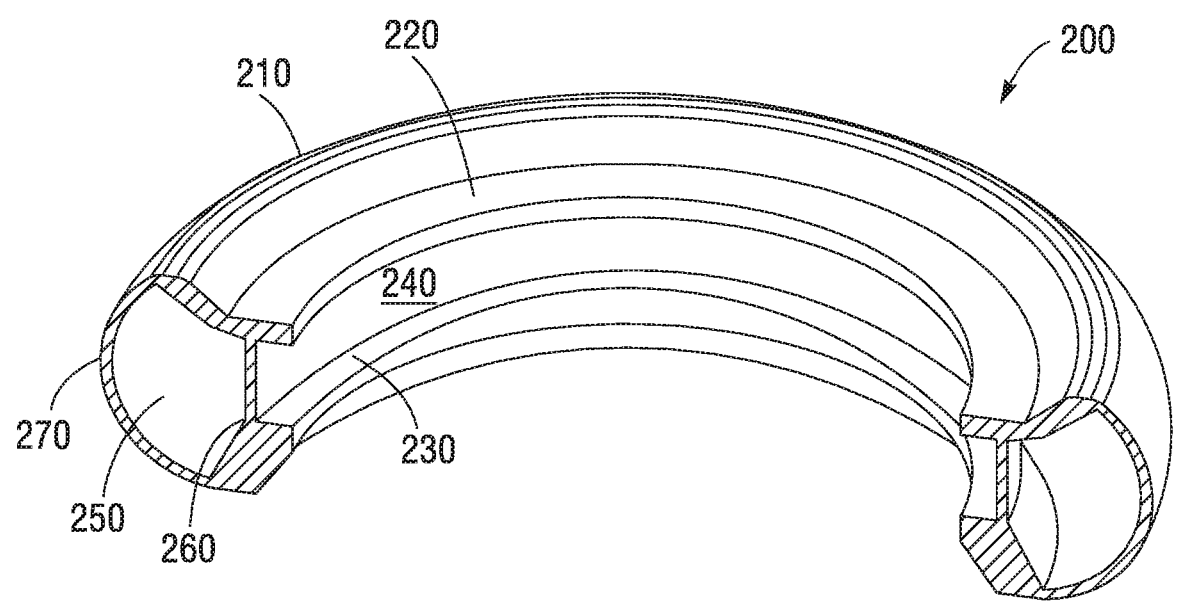
FIG. 2C depicts a cross-sectional view of the fluid-filled open base ring of FIG. 2A.

FIG. 2A depicts a perspective view of an open fluid-filled base ring 200 of an accommodating IOL. FIGS. 2B and 2C depict top plan and cross-sectional views of the open fluid-filled base ring 200, respectively. The open fluid-filled base ring 200 represents an alternative embodiment of the fluid-filled base assembly 100 discussed above with reference to FIGS. 1A-1C and can be used in connection with the power lens 195 depicted in relation to FIG. 1C. The open fluid-filled base ring 200 includes a haptic system 210. The open fluid-filled base ring 200 differs from the base assembly 100 of FIG. 1 in that the open fluid-filled base ring 200 does not include a base lens. As such, any visual correction must be provided by a power lens 195 that may be inserted into the open fluid-filled base ring 200 in a manner depicted in relation to FIG. 1C.

In one embodiment, the open fluid-filled base ring 200 is an open ring, i.e., it is not a complete ring. In one embodiment, the open fluid-filled base ring 200 is provided as a C-shape having two closed ends, 210A, 210B, in which its outer periphery is less than 360 arc degrees. In another embodiment, the open fluid filled base ring 200 is provided as a circular shape of substantially about 360 arc degrees but comprises a pair of closed ends such that the inner cavity 250 is not a continuous circumferential volume but comprises a circumferential volume having a pair of closed ends. Both embodiments permit for the open fluid-filled base ring 200 to increase the diameter defined within the central area of the haptic 210 and accommodate power lenses of varying diameters. The C-shaped or incomplete ring configuration can also allow for toric or non-uniform deformation of a power lens, as a portion of the periphery of the power lens will not be contacted by the open fluid-filled base ring 200 and, therefore, the uncontacted portion of the periphery of the power lens will not experience radially-inward forces applied by the open fluid-filled base ring 200. Thus in one embodiment, the open fluid-filled base ring 200 can transmit a radially-compressive forces around only a pre-determined portion of the circumference of a power lens 195 peripheral edge 197 that is provided or coupled within the open fluid-filled base ring 200 so as to provide an asymmetric radial compression of the power lens 195 implanted within the open fluid-filled base ring 200.

In one embodiment, the open fluid-filled base ring 200 has an arc degree of at least 180, at least 190, at least 200, at least 210, at least 220, at least 230, at least 240, at least 250, at least 260, at least 270, at least 280, at least 290, at least 300 at least 310, at least 320, at least 330, at least 340, at least 350, or 360. In each of the foregoing embodiments, the open-fluid filled base ring has a circumference that defines an angle that is provided within a range between any two of the foregoing values.

The open fluid-filled base ring 200 includes upper and lower flanges 220 and 230, forming a channel 240 therebetween. The channel 240 may be configured to receive and secure the power lens. The haptic system 210 includes a reservoir 250 (see FIG. 2C) that extends through at least a portion of the haptic system 210, e.g. around substantially the entire haptic system 210. The haptic system 210 may include an inner wall 260 and an outer wall 270 that define the reservoir 250. In one embodiment, the inner wall 260 may have a thickness that is less than a thickness of the outer wall 270. The thickness of the inner wall 260 may be about 90%, about 80%, about 70%, about 60%, about 50%, about 40%, about 30%, about 20%, about 10% and about 5% of the thickness of the outer wall 270. The thickness of the inner wall 260 may also be within a range that is between and includes any two of the foregoing values.

The reservoir 250 may be configured to contain a fluid. In certain embodiments, the fluid may be selected from the group consisting of: a silicone oil, a fluorinated silicone oil, a polyphenyl ether, and a fluorinated polyphenyl ether. The fluorinated polyphenyl ether may be one or a combination of a pentafluoro m-phenoxyphenyl ether and an m(pentafluorophenoxy)phenyl m-phenoxyphenyl ether. The fluid contained within the reservoir 250 may function to distribute forces applied to the outer wall 270 of the haptic system 210 to the inner wall 240. For example, the fluid contained within the reservoir 250 may be used to substantially evenly transmit compressive forces applied to a periphery of the haptic system 210, e.g. forces caused from the contraction and/or relaxation of the ciliary muscles. Forces transmitted to the inner wall 260 may subsequently be transmitted to a power lens contained within the channel 240.

Figure 3A:
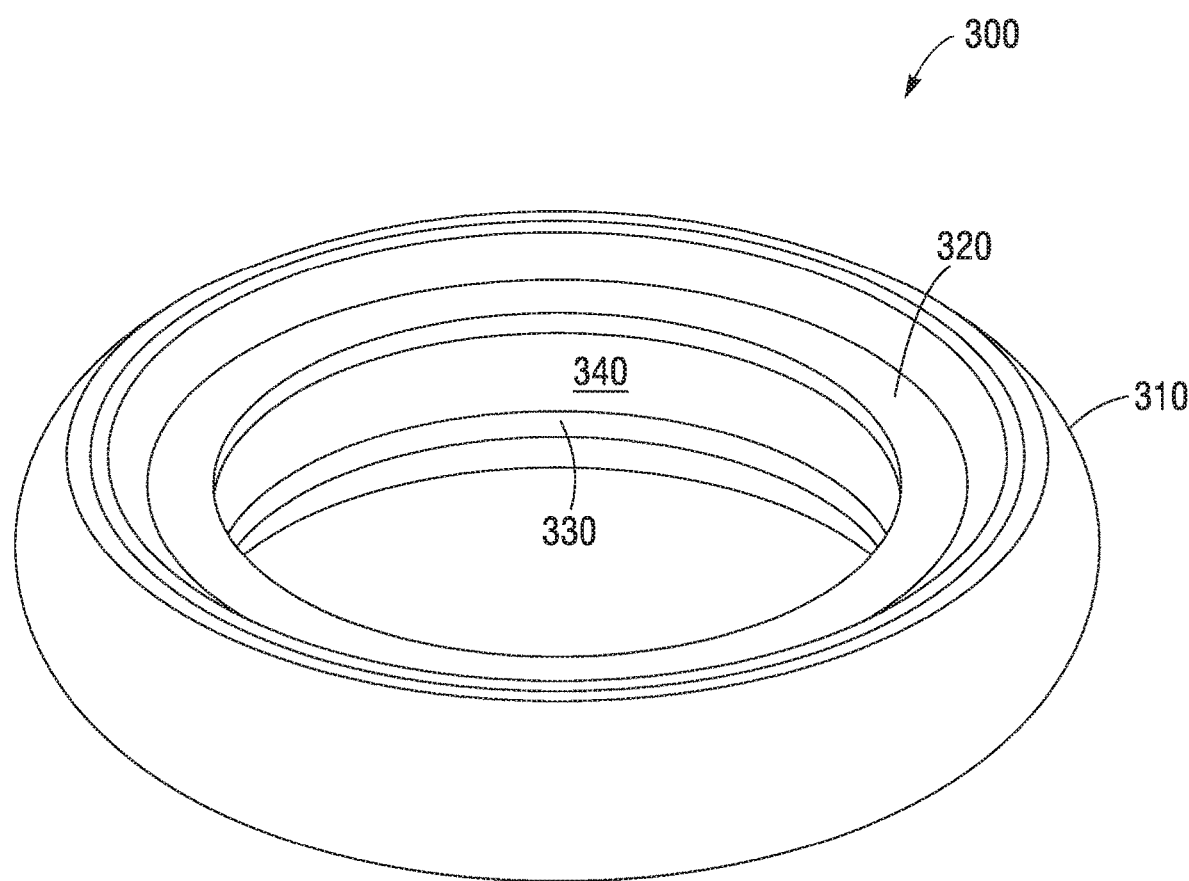
FIG. 3A depicts a perspective view of a fluid-filled closed base ring, in accordance with an embodiment of the present disclosure.
Figure 3B:
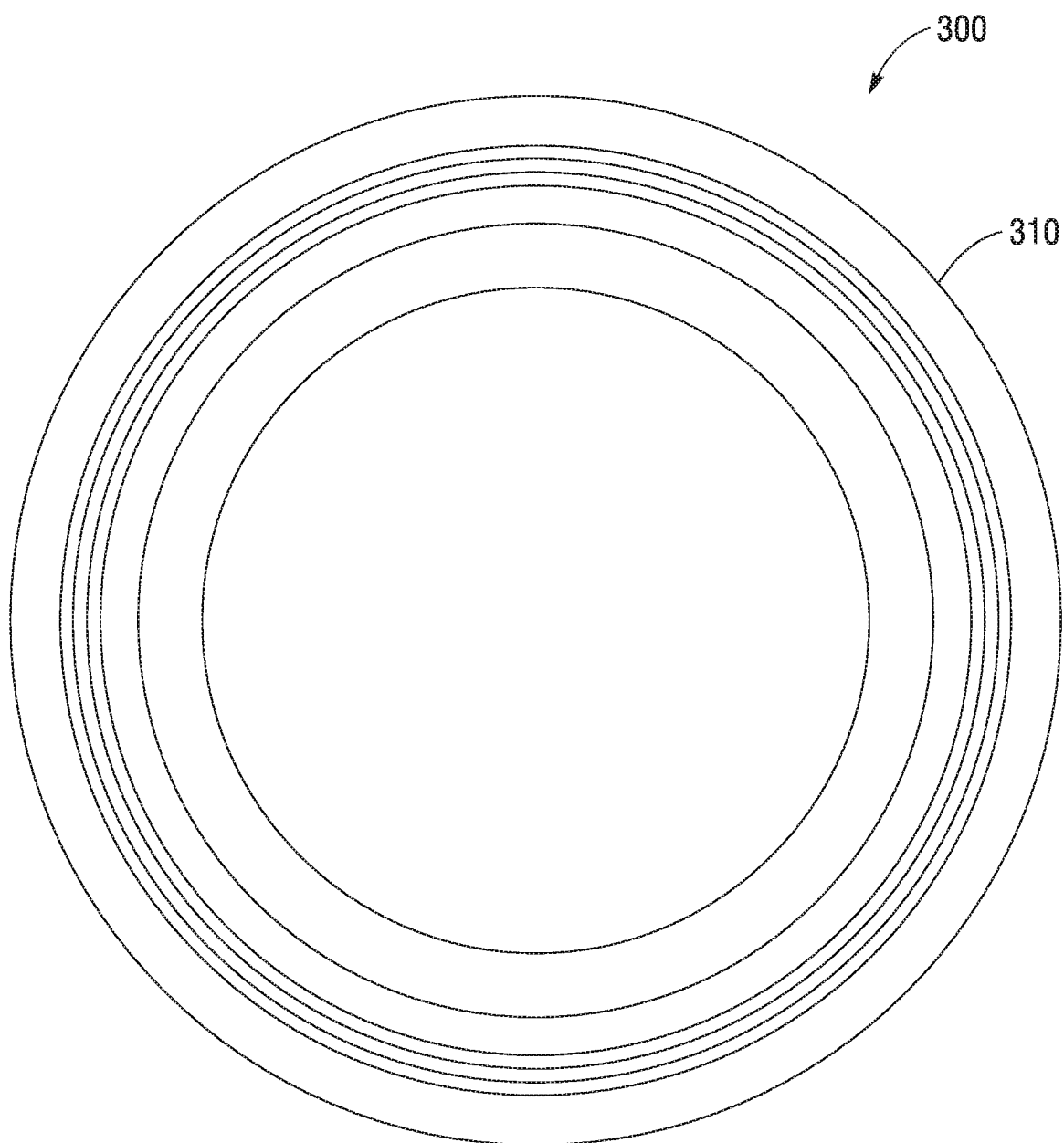
FIG. 3B depicts a top plan view of the fluid-filled closed base ring of FIG. 3A.
Figure 3C:
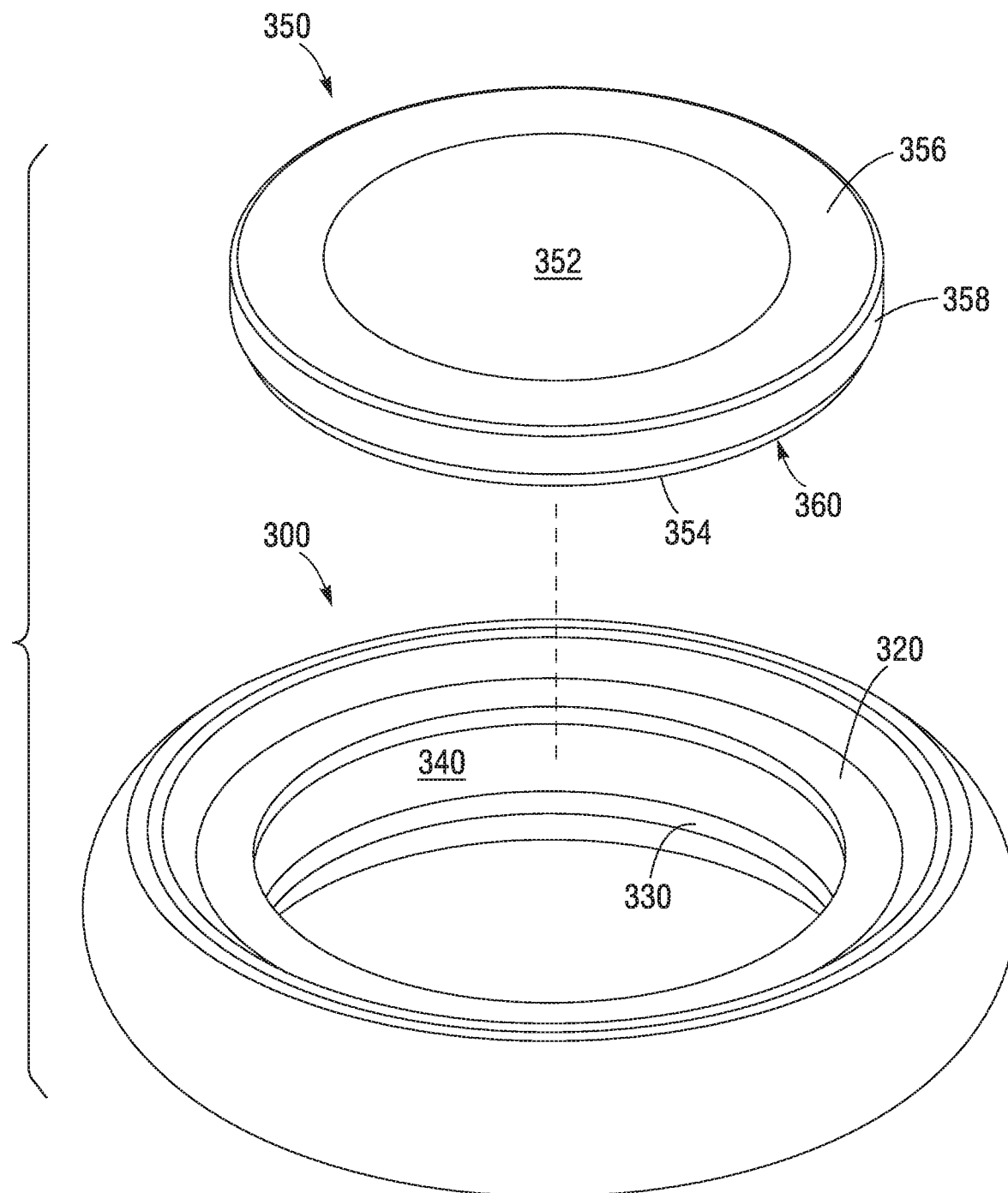
FIG. 3C depicts an exploded perspective view of a power lens coupled to the fluid-filled closed base ring of FIG. 3A.

FIG. 3A depicts a perspective view of a fluid-filled base ring 300, in accordance with another embodiment of the present disclosure. FIG. 3B is a top plan view of the fluid-filled base ring 300. The fluid-filled base ring 300 is substantially similar to the open fluid-filled base ring 200 of FIGS. 2A-C, with the primary difference being that the fluid-filled base ring 300 is a closed ring, rather than an open ring. The fluid-filled base ring 300 may also include a haptic system 310 that is ring shaped. The fluid-filled base ring 300 may also include an upper flange 320 and a lower flange 330 extending radially inwardly from the haptic system 310. The upper flange 320 and the lower flange 330 together define a channel that is configured to secure a power lens within a central portion of the fluid-filled base ring 300. An inner wall 340 is defined between the upper flange 320 and the lower flange 330. As described above with the embodiments of FIGS. 1 and 2, external forces applied to the outer wall of the haptic system 310 (e.g., by the ciliary muscles of an eye) can be translated through the fluid-filled base ring 300 to the inner wall 340 of the haptic system 310 (the channel) to apply forces to a power lens inserted into the channel.

FIG. 3C depicts an exploded perspective view of a power lens 350 that is configured to be coupled to the fluid-filled base ring 300. The fluid-filled base ring 300 is configured to secure the power lens 350 to form an accommodating IOL.

In various embodiments, the power lens 350 includes a flexible membrane 352 on one side, an optic 354 on the opposing side, and a circumferential peripheral edge 358 coupling the flexible membrane and the optic 354. A membrane coupler 356 can extend radially inwardly from the internal side of the circumferential peripheral edge 358 to couple the membrane 352 to the peripheral edge 358. In accordance with one optional aspect, at least a portion of the peripheral edge 358 is in direct contact with the inner wall 340 of the fluid-filled base ring 300. In accordance with another optional aspect, the entirety of the peripheral edge 358 is in direct contact with the inner wall 340 of the fluid-filled base ring 300. The power lens 350 can comprise an optic coupler 360 extending radially inwardly from the internal side of the circumferential peripheral edge 358 to couple the optic 354 to the peripheral edge 358. Preferably, the optic coupler 360 is angled toward the flexible membrane 352 such that it vaults the optic 354 toward the flexible membrane 352. See, e.g., power lens 920 of FIG. 9C and power lens 1020 of FIG. 10D for exemplary cross-sectional views. Thus, in one embodiment, the power lens 350 can be identical to the power lens 920 of FIG. 9C or the power lens 1020 of FIG. 10D.

Other examples of accommodating IOLs are disclosed in U.S. Patent Application Publication No. 2013/0053954, entitled Accommodating Intraocular Lens; U.S. Patent Application Publication No. 2014/0180403, entitled Accommodating Intraocular Lens; U.S. Patent Application Publication No. 2015/0105760, entitled Method and System for Adjusting the Refractive Power of an Implanted Intraocular Lens; and U.S. patent application Ser. No. 14/447,621, entitled Accommodating Intraocular Lens, the entire contents of which are incorporated by reference in their entirety as if fully set forth herein. Any of the features disclosed with respect to the accommodating intraocular lenses in the above-cited references may be applied to any of the base assemblies, the power lenses, or the accommodating IOLs disclosed herein. For example, the various one-piece accommodating IOL embodiments disclosed in U.S. Patent application Publication Nos. 2013/0053954, 2014/0180403, and 2015/0105760 can be utilized as the power lens 350. U.S. patent application Ser. No. 14/447,621 discloses a two-piece accommodating IOL that utilizes a base assembly and a power lens inserted into the base assembly (sometimes referred to as an accommodating IOL or IOL). It should be understood that various embodiments are possible.

Figure 4A:
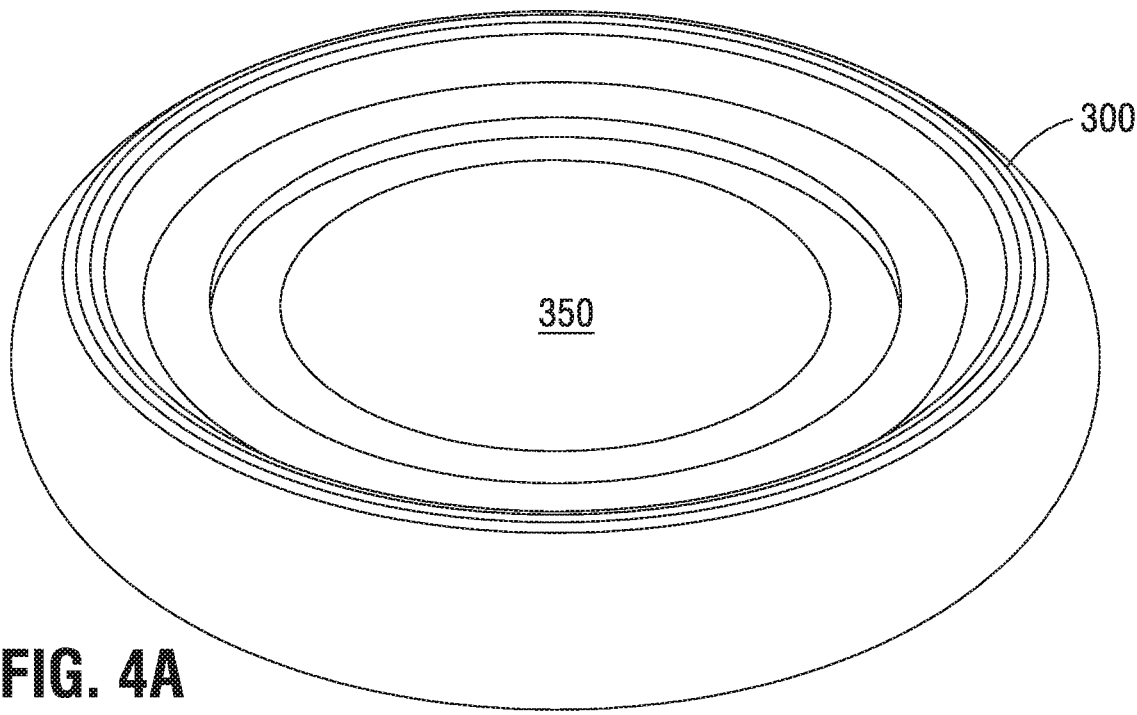
FIG. 4A depicts a perspective view of a power lens coupled to a fluid-filled closed base ring, in accordance with an embodiment of the present disclosure.
Figure 4B:
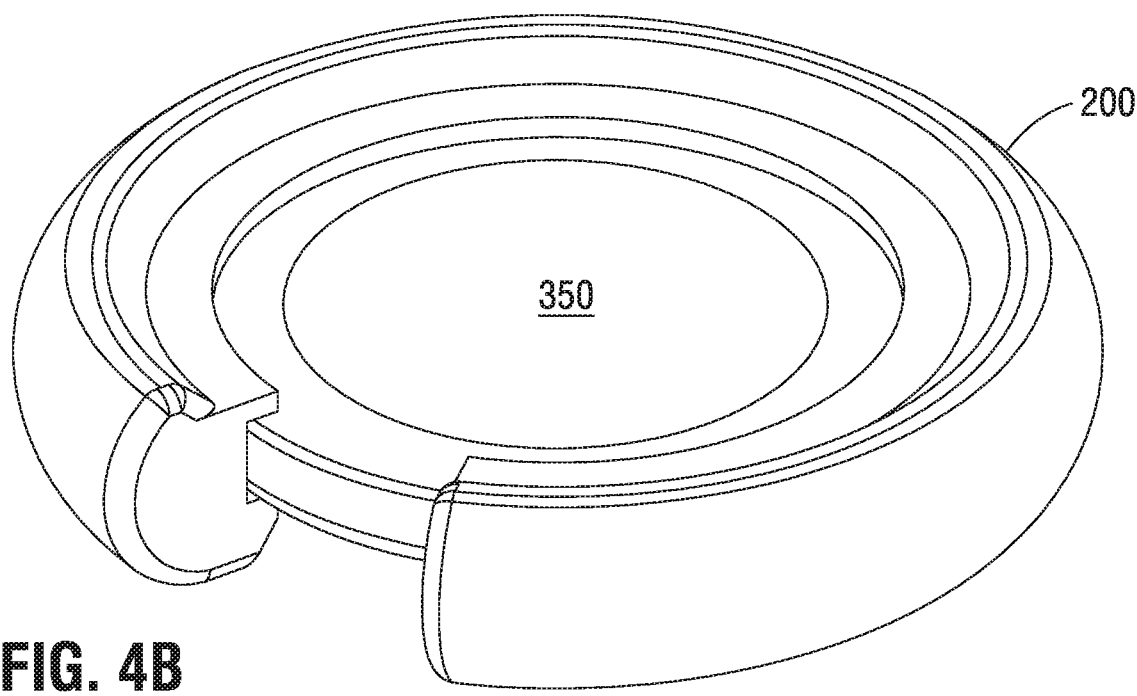
FIG. 4B depicts a perspective view of a power lens coupled to a fluid-filled open base ring, in accordance with an embodiment of the present disclosure.

FIG. 4A depicts a perspective view of a power lens 350 coupled to a fluid-filled base ring 300. FIG. 4B depicts a perspective view of a power lens 350 coupled to an open fluid-filled base ring 200. In accordance with one aspect, only at least a portion of the circumferential peripheral edge 358 is in direct physical contact with the inner wall 240, 340 of the fluid-filled base ring 200, 300 (e.g. FIG. 4B). In accordance with another aspect, the entire circumferential edge 358 is in direct contact with the inner wall 340 of the fluid-filled base ring 300 (e.g., FIG. 4A).

Figure 5A:
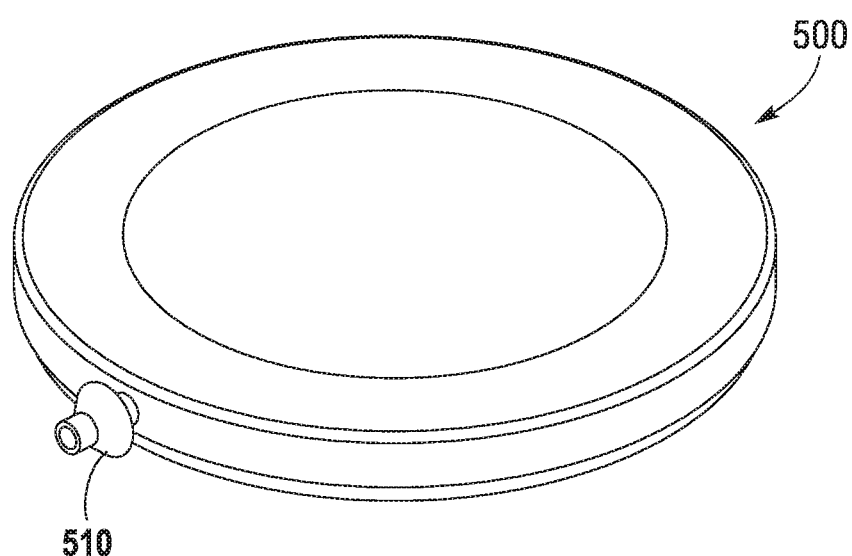
FIG. 5A depicts a perspective view of a power lens having a fluid transfer system, in accordance with an embodiment of the present disclosure.

FIG. 5A provides a perspective view of a fluid-exchange power lens 500 in accordance with an embodiment of the present disclosure. The power lens 500 shown in FIG. 5A can include the components as described with respect to the power lens 350 shown in, for example, FIG. 3C. In various embodiments, the power lens 500 includes a reservoir for storing a fluid that can be transferred to a fluid-filled base assembly that forms part of an accommodating IOL. The power lens 500 includes a fluid transfer valve 510 that is configured to be removably coupled to the fluid-filled base assembly (see FIG. 5B). The fluid transfer valve 510 functions to provide a fluid communication between the power lens 500 and a base assembly shown in FIGS. 1-4.

Figure 5B:
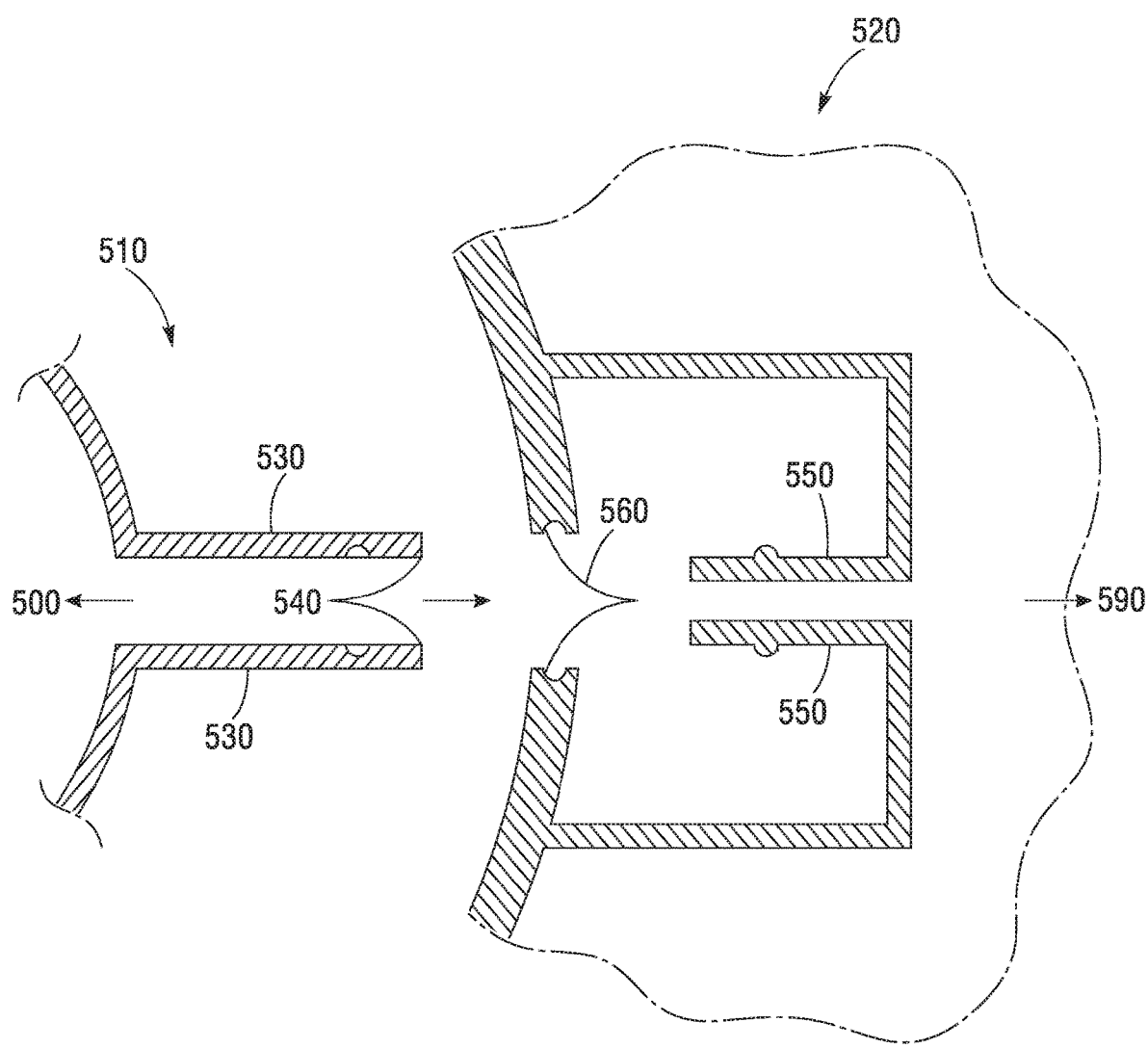
FIG. 5B is a close up view of a fluid transfer system, in accordance with an embodiment of the present disclosure.

FIG. 5B depicts an embodiment of a fluid transfer system for transferring fluid between a power lens and a fluid-filled base assembly of an accommodating IOL. The fluid transfer valve 510 is configured to interact with a receiving valve 520 that is disposed on an inner wall of the fluid-filled base assembly (e.g., 180, 240, 340 of FIGS. 1B, 2A, 3A, respectively. In various embodiments, the fluid transfer valve 510 can be implemented as part of a power lens 500 and the receiving valve 520 can be implemented as part of a fluid-filled base assembly 590 or vice versa. The fluid transfer valve 510 includes a canal 530 leading to a one-way valve 540. The receiving valve 520 includes valve release canal 550. The receiving valve 520 includes its own one-way valve 560. When the fluid transfer valve 510 and the receiving valve 520 stand alone, both one-way valves 530, 560 are closed, and no fluid escapes either the power lens 500 or the fluid-filled base assembly 590. When the canal 530 of the fluid transfer valve 510 is inserted into the one-way valve 560 of the fluid-filled base assembly 590, the canal 530 forces open the one-way valve 560. Similarly, the valve release canal 550 forces open the one-way valve 540. As a result, both one-way valves 540, 560 are pushed open, and fluid can freely flow between the power lens 500 and the fluid-filled base assembly 590.

FIGS. 6 and 7 depict embodiments of a toric base assembly 600, 700. The base assembly 600, 700 comprises a base lens 610, 710 and a substantially circular haptic system 620, 720 having an outer periphery and at least two regions having different flexibility. Because at least two regions have greater flexibility 640, 730 than in the remaining regions of the haptic system 620, 720, the application of a radially-compressive force onto the outer periphery of the haptic system 620, 720 results in an asymmetric deformation of the haptic system 620, 720 in the regions of greater flexibility 640, 730. In other words, the regions of greater flexibility 640, 730 are radially compressed or compressible to a greater extent than the remaining regions of the haptic system 620, 720. This asymmetric deformation, in turn, may provide a toric power change in one or both of a base lens 610, 710 and a power lens that is provided within the haptic system 620, 720.

Figure 6A:
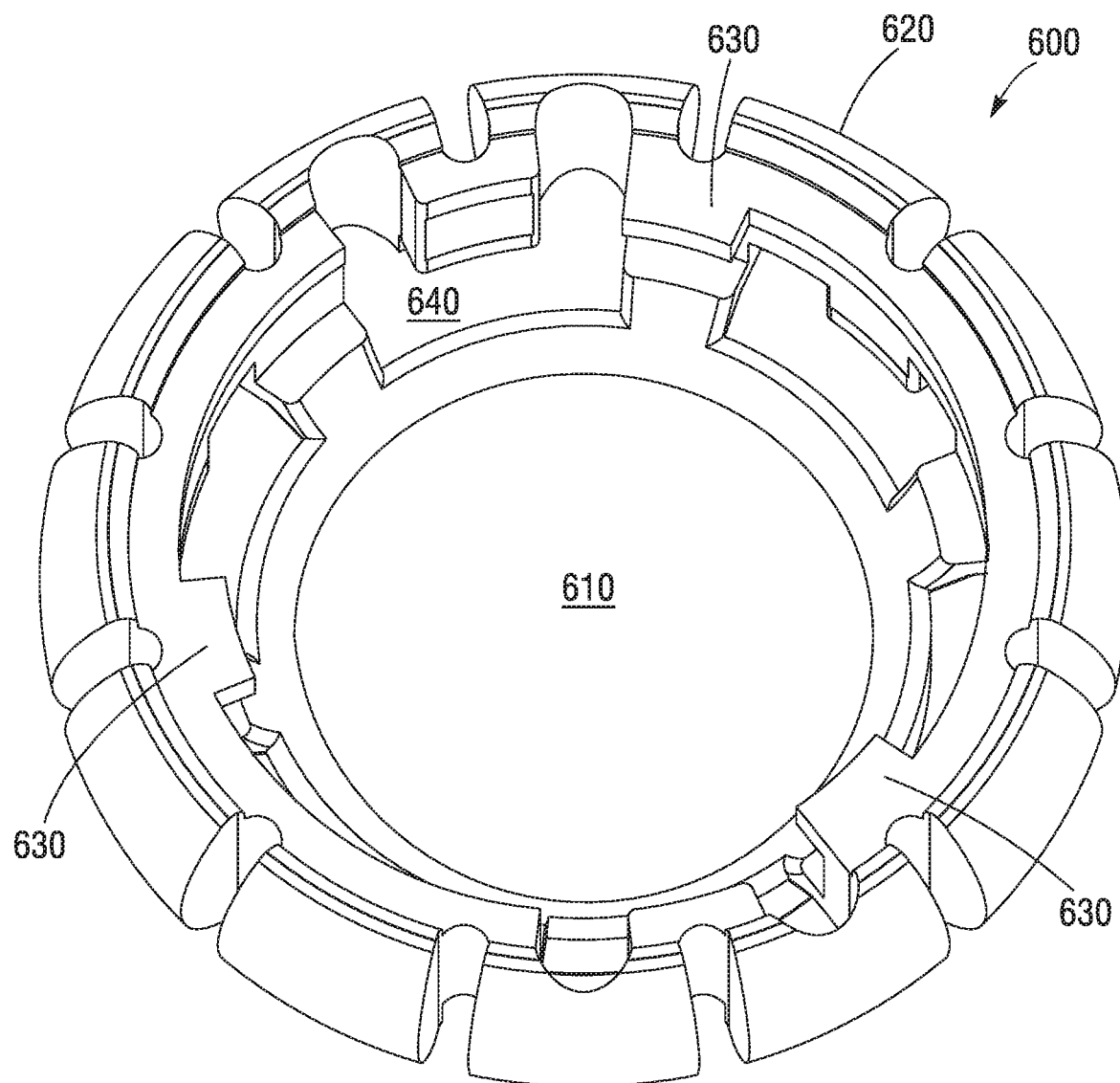
FIG. 6A depicts a perspective view of a toric base assembly, in accordance with an embodiment of the present disclosure.
Figure 6B:
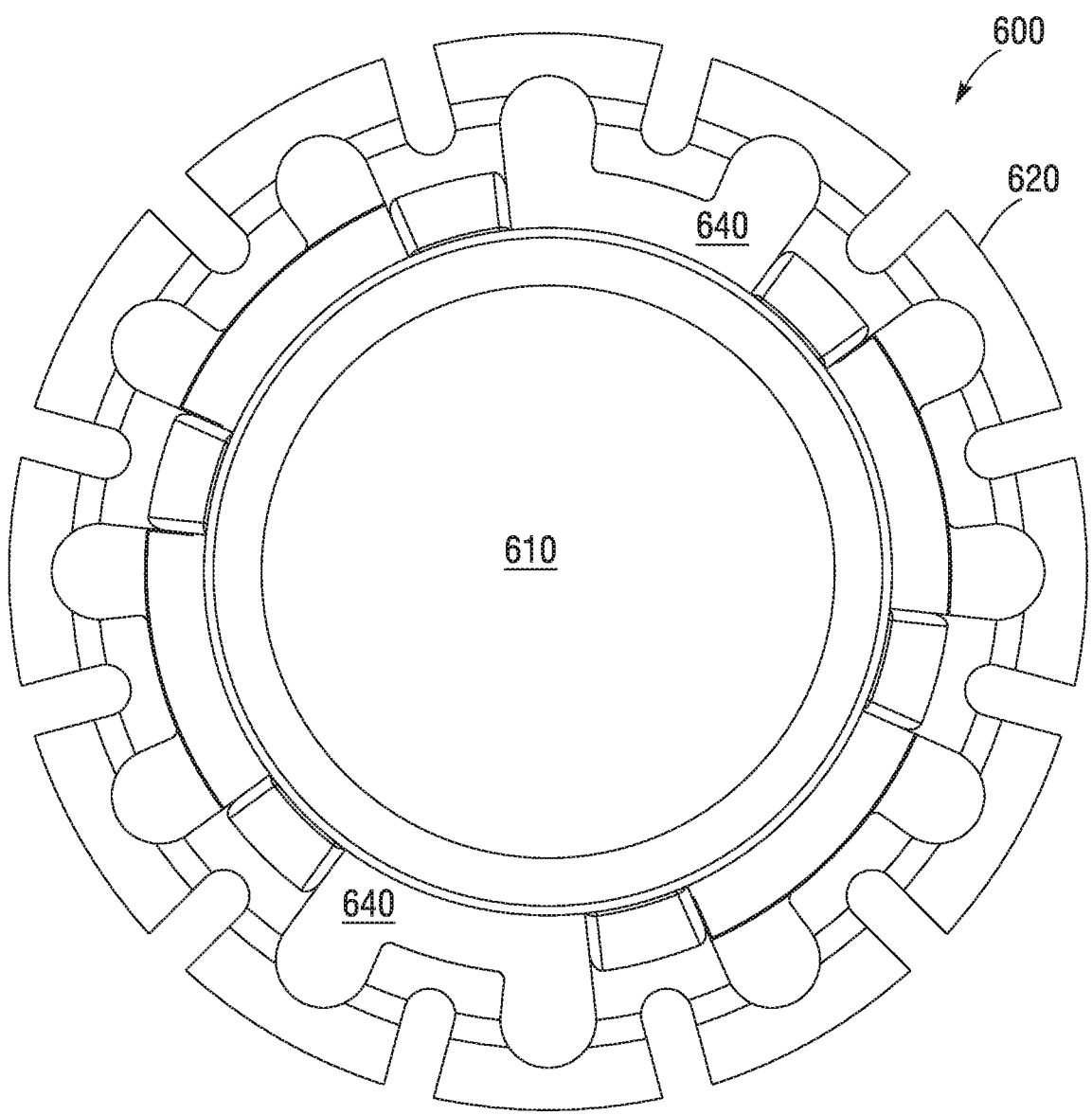
FIG. 6B depicts a top plan view of the toric base assembly of FIG. 6A.

FIGS. 6A-6B depicts one embodiment of the toric base assembly 600. FIG. 6A depicts a perspective view of a toric base assembly 600 of an accommodating toric IOL, in accordance with an embodiment of the present disclosure. FIG. 6B provides a top plan view of the toric base assembly 600. The toric base assembly 600 includes a base lens 610 and substantially circular haptic system 620. The toric base assembly 600 includes a plurality of tabs 630 to engage an inserted power lens (not depicted). The outer periphery of the haptic system 620 is configured to receive deforming forces caused by the ciliary muscles of the eye to cause radially-inward compression of the haptic system 620. These forces are then translated to either one or both of the base lens 610 and/or a power lens that can be inserted into the base assembly 600. In the embodiment shown in FIGS. 6A and 6B, portions of the haptic system 620 have greater structural flexibility, leading to uneven translation of a radially-inwardly applied force by various portions of the haptic system 620. In the embodiment shown, cutouts 640 are formed in the haptic system 620 to create greater flexibility proximate the cutouts 640. The cutouts 640 can be formed to provide an area of the haptic 620 that is thinner than the remaining areas of the haptic 620. As a result, greater compressive forces are applied by the haptic system 620 proximate the cutouts 640, which in turn results in toric deformation of either or both the base lens 610 and an inserted power lens.

Figure 7A:
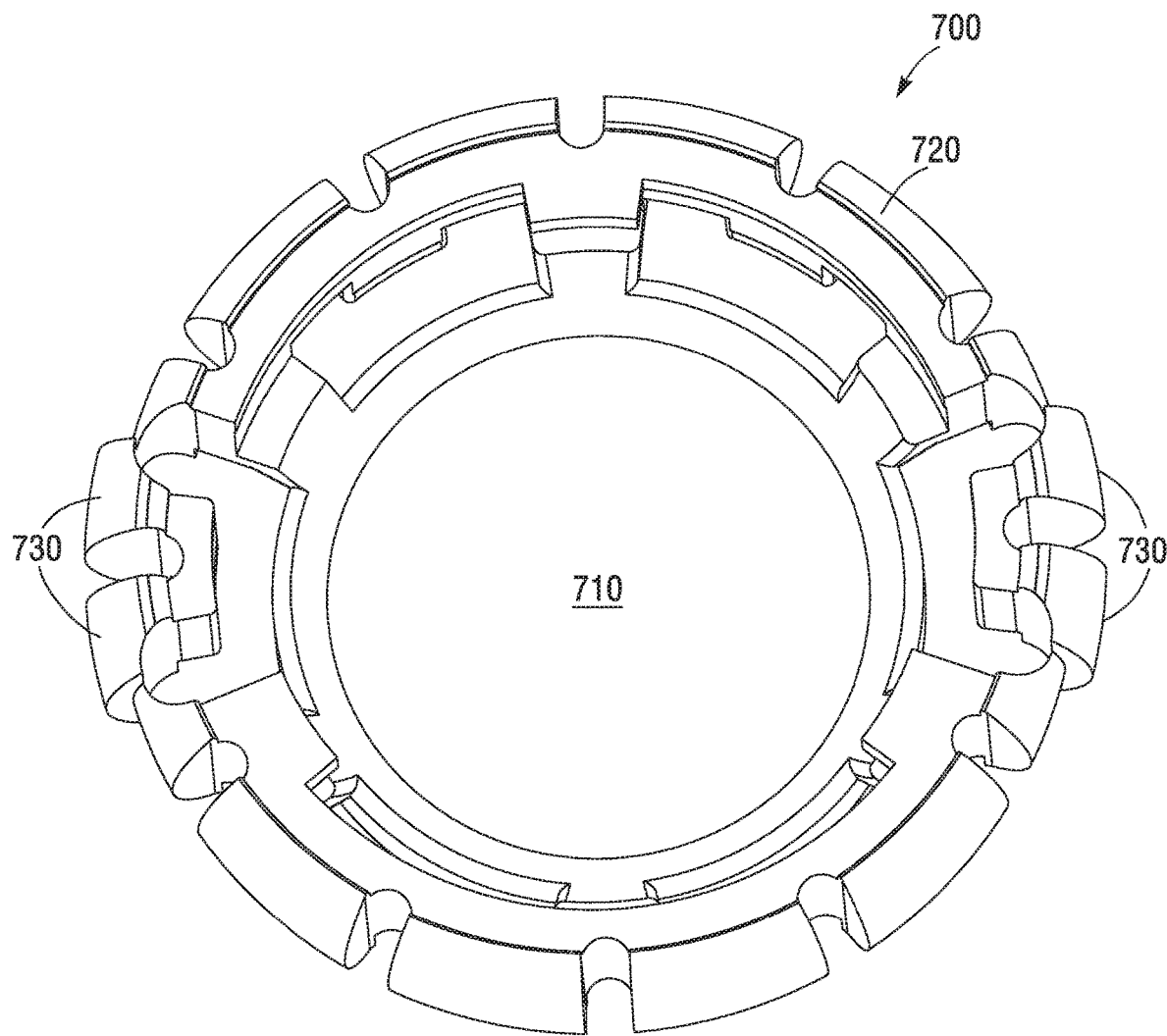
FIG. 7A depicts a perspective view of a toric base assembly, in accordance with an embodiment of the present disclosure.
Figure 7B:
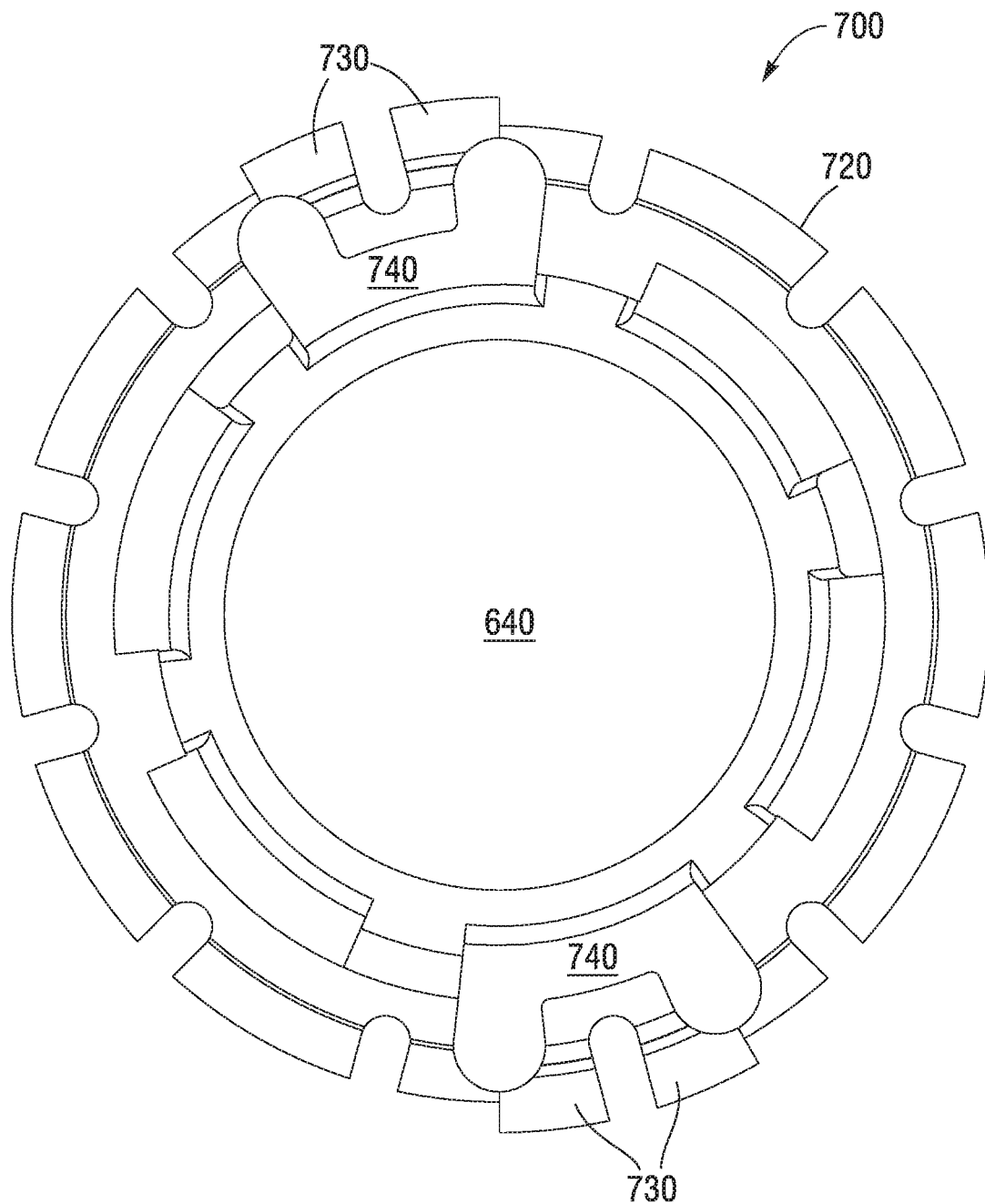
FIG. 7B depicts a top plan view of the toric base assembly of FIG. 7A.

FIGS. 7A and 7B provide perspective and top plan views, respectively, of an alternative toric base assembly 700, in accordance with an embodiment of the present disclosure. The toric base assembly 700 includes a base lens 710 and a haptic system 720. In the toric base assembly 700 shown in FIGS. 7A and 7B, in addition to having cutouts 740 to create greater flexibility in certain regions of the haptic system 720, the haptic system 720 includes two extended regions 730 that extend beyond the circumference defined by the haptic system 720. The extended regions 730 and the cutouts 740 cause an unequal distribution of compressive forces, resulting in toric deformation of either or both the base lens 710 and an inserted power lens.

The accommodating IOL may be provided with a base assembly that permits for varying profiles. The varying profiles may be provided by configuring the base assembly such that the power lens is placed farther away from the base lens (i.e., high profile) or closer to the base lens (i.e., low profile).

Figure 8A:
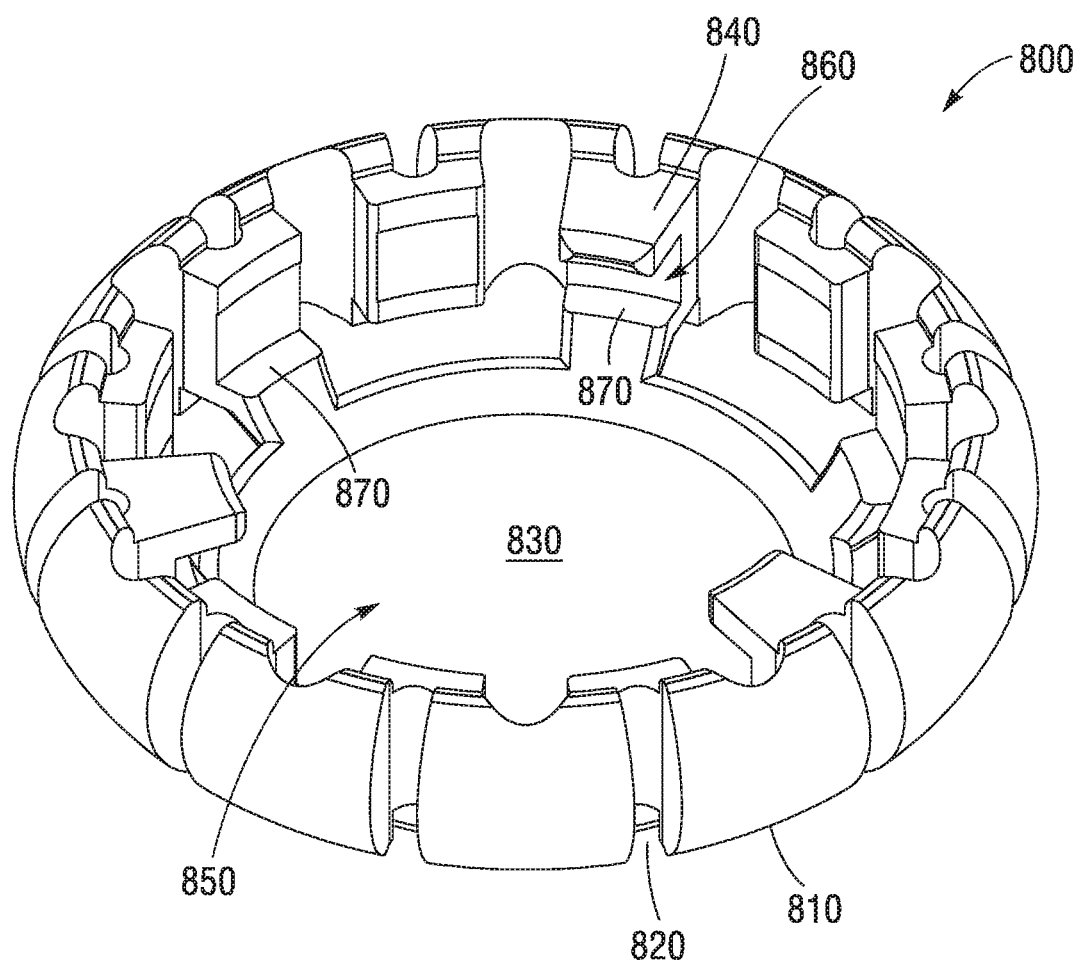
FIG. 8A depicts a perspective view of a base assembly, in accordance with an embodiment of the present disclosure.
Figure 8B:
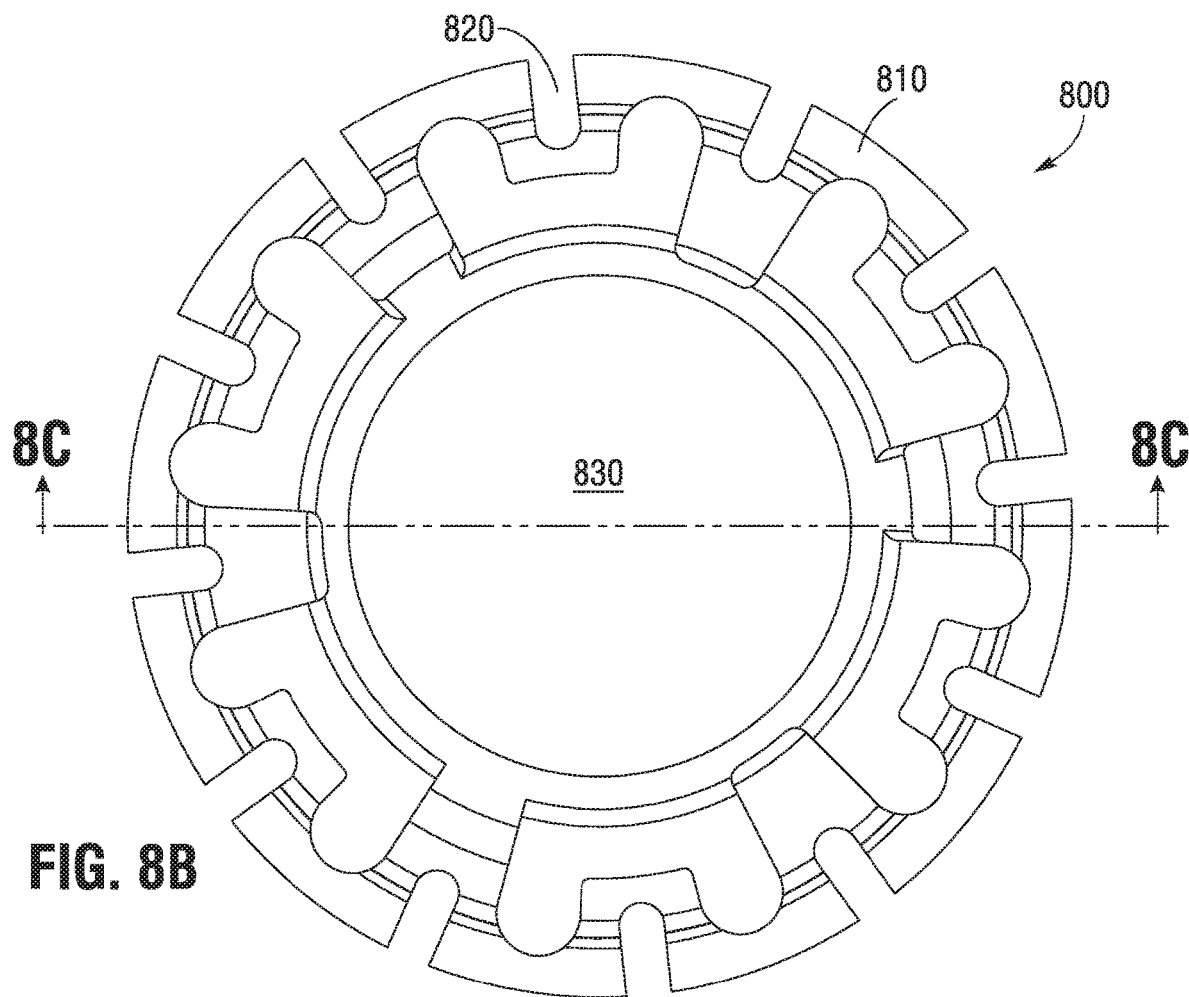
FIG. 8B depicts a top plan view of the base assembly of FIG. 8A.
Figure 8C:
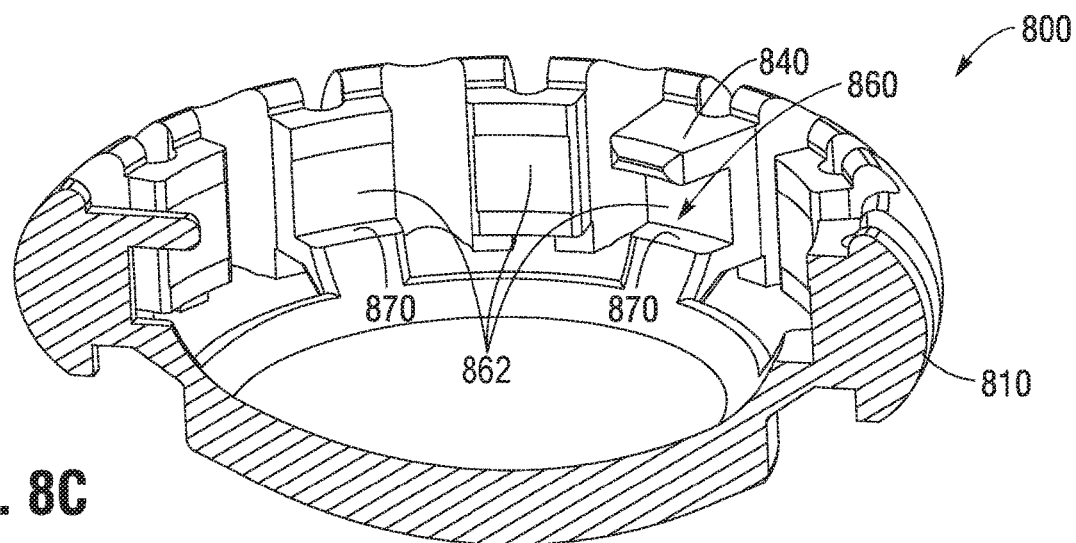
FIG. 8C depicts a cross-sectional view of the base assembly of FIG. 8A.

FIGS. 8A-8C depict an embodiment of a high profile IOL base assembly 800. FIG. 8A depicts a perspective view of the base assembly 800 and FIGS. 8B and 8C depict top plan and cross-sectional views, respectively, of the base assembly 800.

The base assembly 800 includes a first open end 800A and a second end 800B that may optionally include a base lens 830. The haptic system 810 includes an outer periphery and an inner surface facing a central cavity. The inner surface may comprise a plurality of spaced-apart contact points 862 configured to engage a portion of a peripheral edge of an implanted power lens (not depicted) that may be provided to fit within a central cavity of the base assembly 800. A plurality of tabs 840 may be provided to extend into a cavity 850 and to create a plurality of recesses 860 within the cavity 850 to retain a portion of a peripheral edge of a power lens. A plurality of tables 870 extend from a bottom of the base assembly 800 into the cavity 850 along portions of a periphery of the cavity 850. The tables 870 rise to a level such that a top surface of the tables 870 is in substantially the same plane formed by the bottom surfaces of the recesses 860. The tables 870 in combination with the recesses 860 ensure that an inserted power lens is secured at a desired position within the cavity 850 with respect to the base lens 830.

The haptic system 810 has a height $h_2$ between a first edge and a second edge of its outer periphery. The power lens comprises a first side, a second side and a peripheral edge coupling the first and second sides. The power lens may further comprise a closed cavity configured to house a fluid The first side of the power lens is positioned at a predetermined distance $h_1$ from the first edge of the haptic system 810. This predetermined distance $h_1$ determines the profile of the base assembly 800. In one exemplary embodiment, the predetermined distance $h_1$ may be in the range of about 0 mm to about 0.75 mm. In accordance with another embodiment, the predetermined distance $h_1$ may be in the range of about 0.01% to about 37% of the height of the haptic $h_2$. As shown in FIG. 8C, the predetermined distance can be measured by reference to a bottom surface of a plurality of tabs 840 that is used to secure a first side of the power lens. Thus, in accordance with this embodiment, the bottom surface of the tabs may be positioned at a distance of about 0 mm to about 0.75 mm from the first edge of the haptic system 810 or at a distance, from the first edge of the haptic system 810, of about 0.01% to about 37% of the height $h_2$ of the haptic system 810.

The haptic system 810 may be is substantially circular with a plurality of outer grooves 820. The outer grooves 820 may extend along at least a portion of the height of the haptic system 810. The outer grooves 820 may be configured to permit the haptic to be radially compressed, radially expanded, or both. In one embodiment, the outer grooves 820 may be disposed in the outer periphery of the haptic system 810 opposite the inner surface contact points 862.

FIGS. 9 and 10 depict embodiments of a low profile base assembly.

Figure 9A:
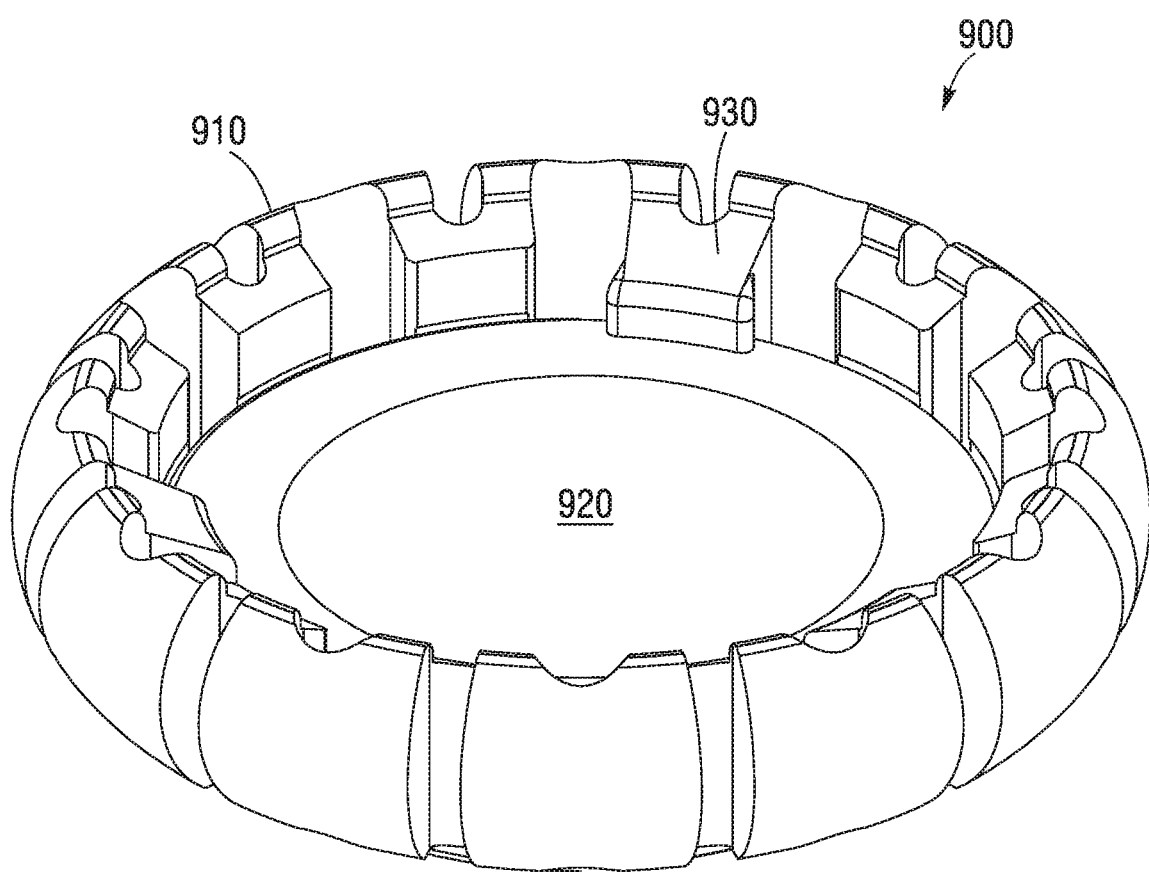
FIG. 9A depicts a perspective view of an accommodating IOL configured to position a power lens closer to a base lens of the base assembly, in accordance with an embodiment of the present disclosure.
Figure 9B:
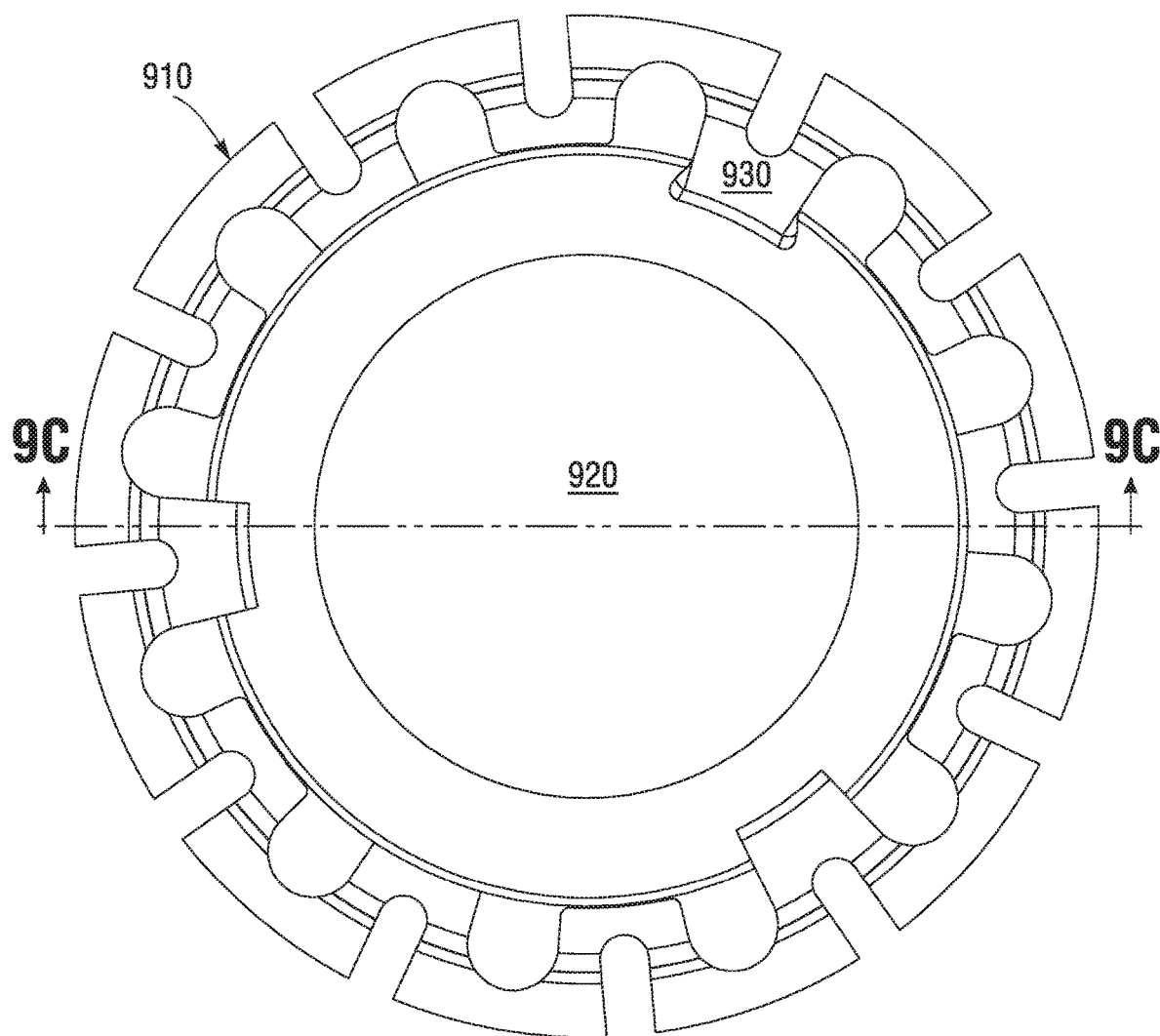
FIG. 9B depicts a top plan view of the accommodating IOL of FIG. 9A.
Figure 9C:
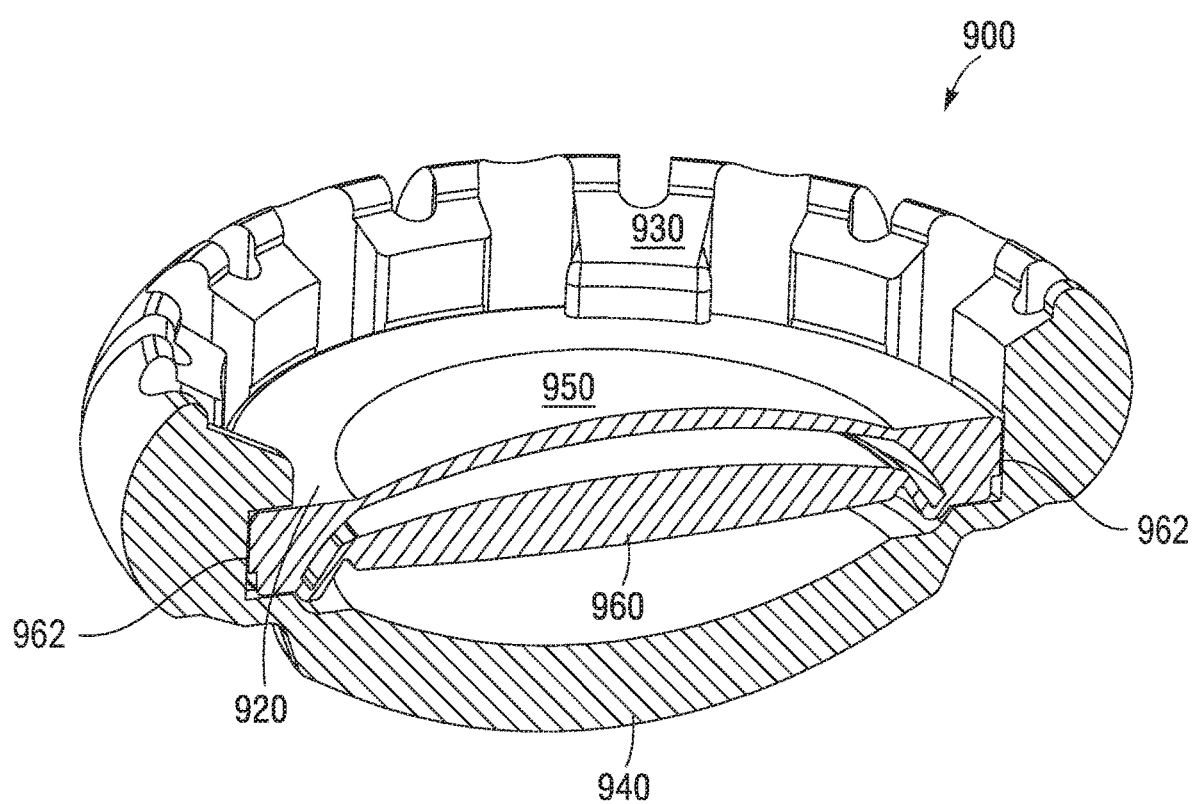
FIG. 9C depicts a cross-sectional view of the accommodating IOL of FIG. 9A.

FIG. 9A depicts a perspective view of an accommodating intraocular lens 900 including a base assembly 900 and a power lens 920 coupled to the base assembly 910. Compared to the base assembly 800 of FIG. 8A, the base assembly 900 of the accommodating IOL 900 is configured to position the power lens 920 deeper within the base assembly 910, and closer to a base lens of the base assembly 910. FIG. 9B provides a top plan view of the accommodating IOL and FIG. 9C provides a cross-sectional view of the accommodating IOL including the base assembly 900 and the power lens 920. The accommodating IOL includes a power lens 920 that is secured in the base assembly 900, and held in place, in part, by a plurality of tabs 930 that extend radially inwardly from the base assembly 900 into a central cavity within the base assembly 900. The bottom surface of the tabs 930 contact a first side of the power lens 920, similarly as with FIG. 8C. As can be seen most clearly in FIG. 9C, the power lens 920 is positioned proximate a base lens 940. In the embodiment shown, the power lens 920 comprises a flexible membrane 950, and a power lens optic 960. The flexible membrane 950 and the power lens optic are spaced apart, and a fluid fills the space between the two. The power lens optic 960 and the base lens 940 are proximate one another.

A haptic system 910 has a height $h_2$ between a first edge and a second edge of its outer periphery. The power lens comprises a first side, a second side and a peripheral edge coupling the first and second sides. The power lens may further comprise a closed cavity configured to house a fluid The first side of the power lens is positioned at a predetermined distance $h_1$ from the first edge of the haptic system 910. This predetermined distance $h_1$ determines the profile of the base assembly 900. In one exemplary embodiment, the predetermined distance $h_1$ may be in the range of about 0 mm to about 0.75 mm. In accordance with another embodiment, the predetermined distance $h_1$ may be in the range of about 0.01% to about 37% of the height of the haptic $h_2$. As shown in FIG. 9C, the predetermined distance can be measured by reference to a bottom surface of a plurality of tabs 930 that is used to secure a first side of the power lens. Thus, in accordance with this embodiment, the bottom surface of the tabs may be positioned at a distance of about 0.75 mm to about 1.5 mm from the first edge of the haptic system 810 or at a distance, from the first edge of the haptic system 910, of about 38% to about 75% of the height $h_2$ of the haptic system 910.

The haptic system 910 may be substantially circular with a plurality of outer grooves 920. The outer grooves 920 may extend along at least a portion of the height of the haptic system 910. The outer grooves 920 may be configured to permit the haptic to be radially compressed, radially expanded, or both. In one embodiment, the outer grooves 920 may be disposed in the outer periphery of the haptic system 910 opposite the inner surface contact points 962.

The lower profile of the accommodating IOL amplifies power change by the accommodating IOL 900, as will be described in greater detail below with respect to FIG. 10.

FIGS. 10A-10D depict another embodiment of a low profile accommodating IOL 1000, in which a low profile base assembly 1010 is configured to place a power lens 1020 deeper within the base assembly 1010, in close proximity with a base lens 1030, to create a greater range of optical power possible with a particular IOL configuration. The low profile accommodating IOL 1000 includes a base assembly 1010, and a power lens 1020 configured to be secured within the base assembly 1010. The base assembly 1010 comprises a haptic portion 1015 for translating forces applied to the periphery of the haptic portion 1015 to the power lens 1020.

Figure 10A:
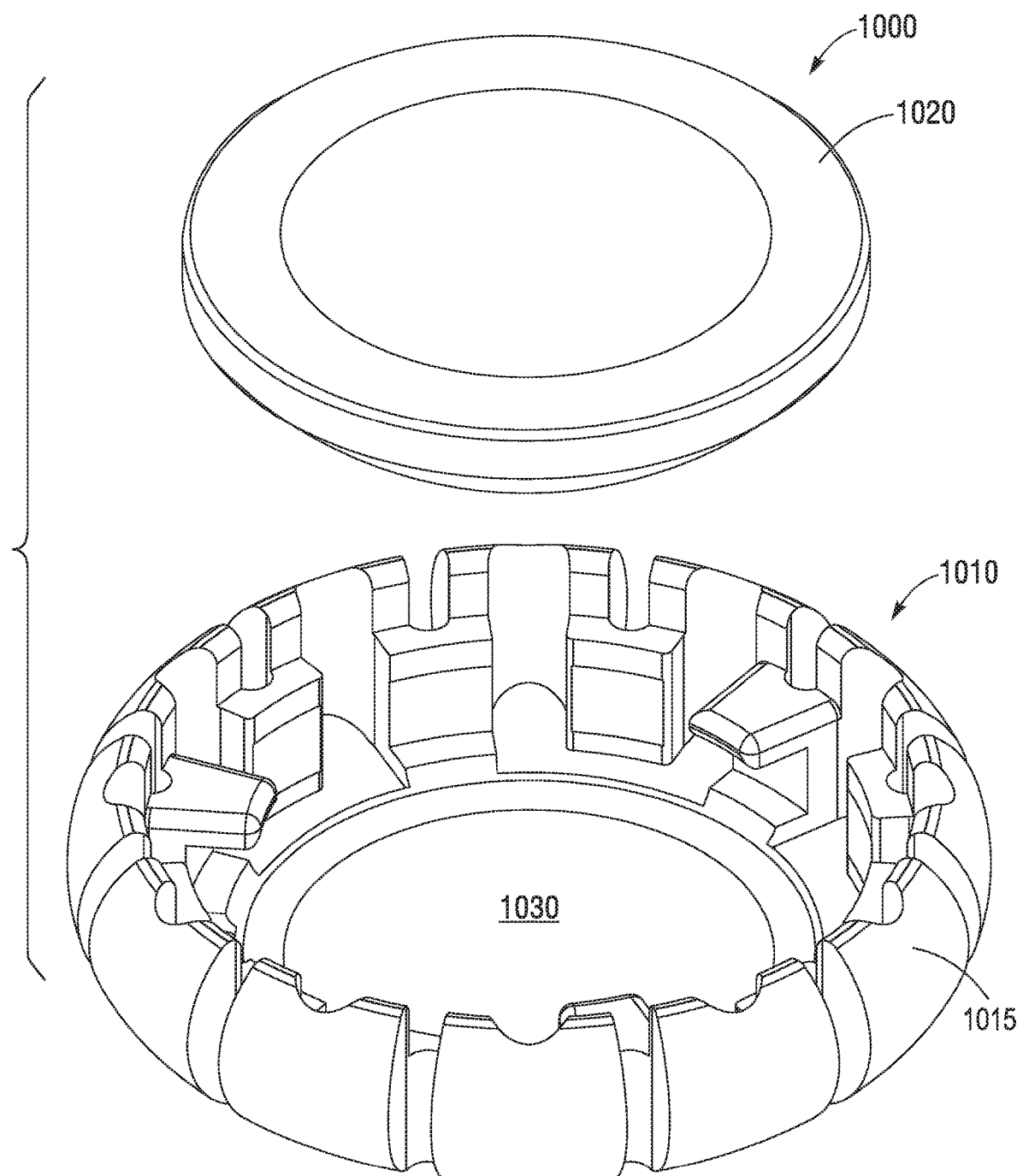
FIG. 10A depicts an exploded perspective view of a low profile accommodating IOL, in accordance with an embodiment of the present disclosure.
Figure 10B:
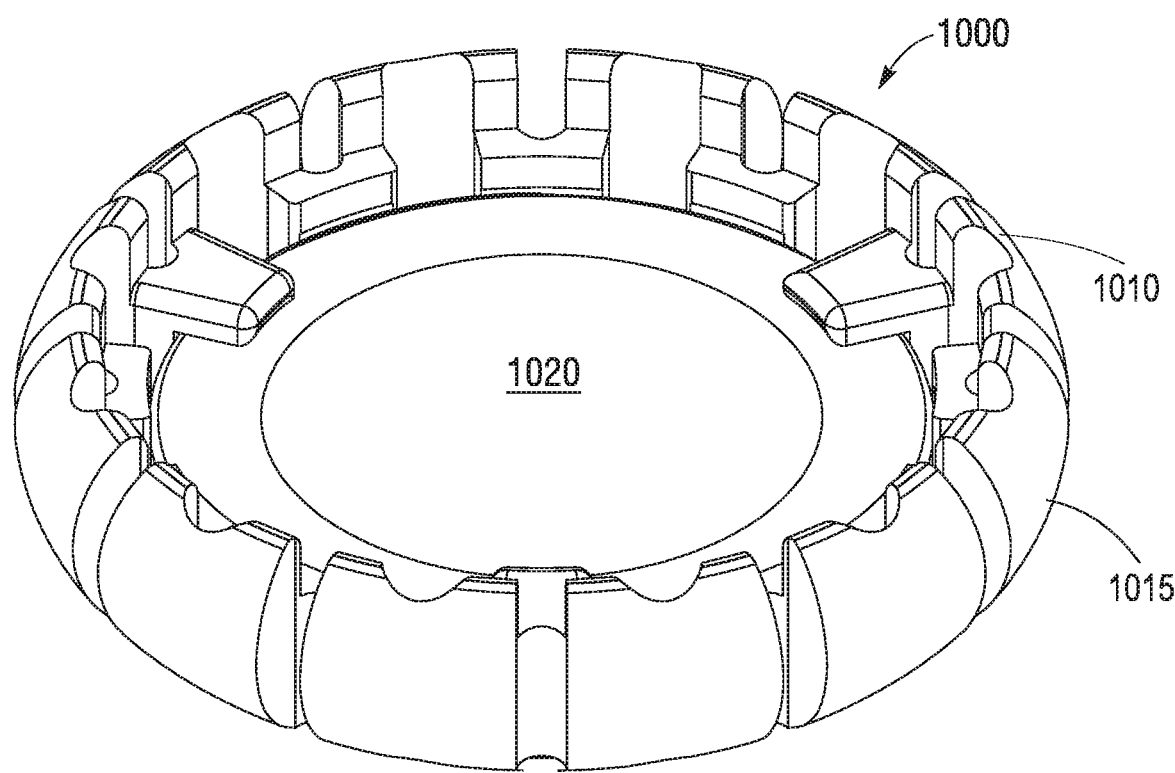
FIG. 10B depicts a perspective view of the low profile accommodating IOL of FIG. 10A.
Figure 10C:
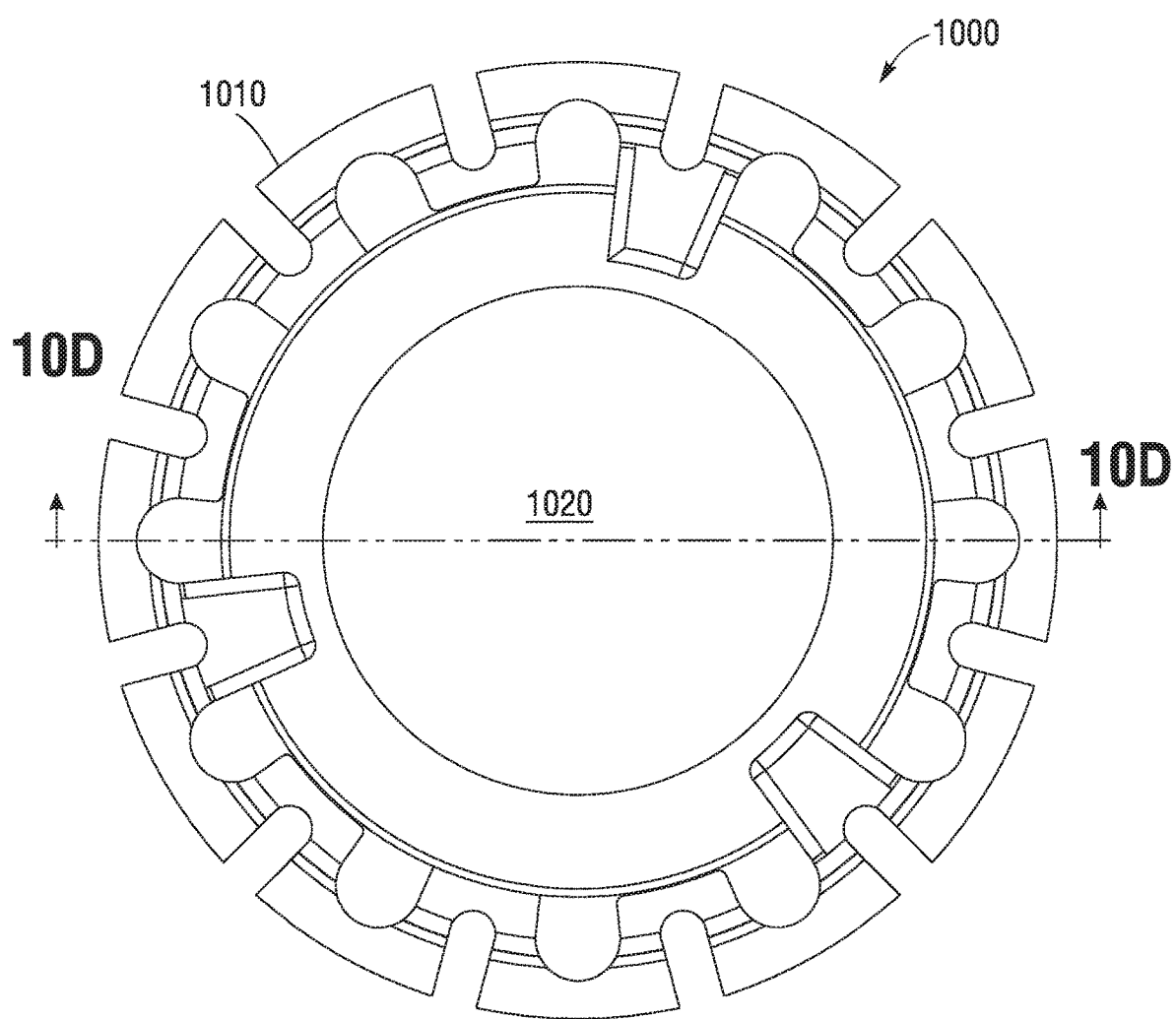
FIG. 10C depicts a top plan view of the low profile accommodating IOL of FIG. 10A.
Figure 10D:
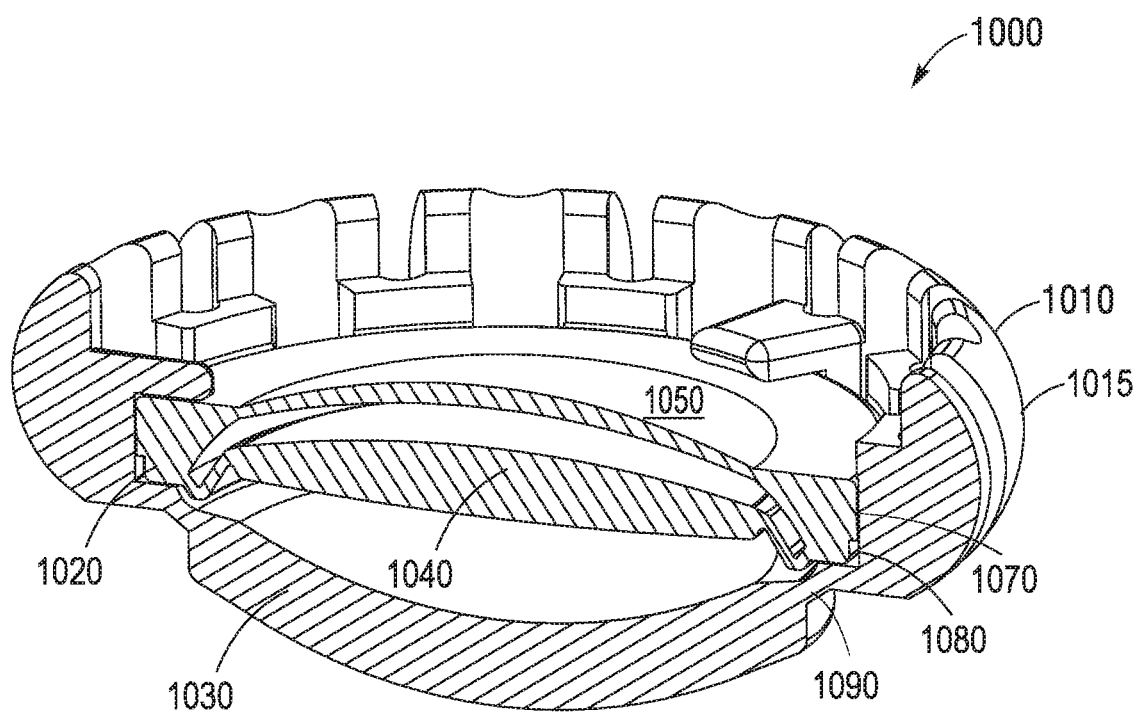
FIG. 10D depicts a perspective cross-sectional view of the low profile accommodating IOL of FIG. 10A.

As can be seen in cross sectional view of FIG. 10D, the power lens 1020 includes a flexible membrane 1050 and a power lens optic 1040, while the base assembly 1010 includes a haptic portion 1015 for translating forces applied to the periphery of the haptic portion 1015 to the power lens 1020 and a base lens 1030. The base lens 1030 and the power lens optic 1040 are proximate one another, and the lower profile of the accommodating IOL amplifies power change by the power lens 1020. Change in power by the accommodating IOL 1000 is largely produced by accommodation of the power lens 1020. Furthermore, accommodation of the power lens 1020 is most effectively produced by applying forces to the membrane 1050, rather than to the power lens optic 1040. As such, power change of the accommodating IOL 1000 is most efficient when forces applied to the periphery of the haptic 1015 are translated efficiently to the membrane 1050.

The low profile accommodating IOL 1000 efficiently translates forces from the haptic 1015 to the membrane 1050 in several ways. First, placement of the power lens 1020 deeper within the haptic 1015 leads to more efficient translation of forces from the haptic 1015 to the power lens 1020 (which comprises the membrane 1050). This is due, at least in part, to the fact that when the power lens 1020 is positioned higher up within the haptic 1015, a greater proportion of the forces exerted on the periphery of the haptic 1015 are distributed to the base lens 1030, rather than the power lens 1020. The portion of the force that is distributed to the base lens 1030 does not significantly affect accommodation and/or power change, and therefore, is not utilized efficiently to effect power change by the accommodating IOL 1000. By moving the power lens 1020 lower within the haptic 1015, a greater proportion of forces are distributed to the power lens 1020 rather than being lost to the base lens 1030. Furthermore, placement of the power lens 1020 proximate the base lens 1030 allows for the power lens 1020 to be in closer proximity with a hinge portion 1090, which translates at least a portion of the forces being distributed to the base lens 1030 to the power lens 1020.

As discussed above, even if forces are applied to the power lens 1020, accommodation is maximized when forces are applied to the membrane 1050 rather than the power lens optic 1040. A cutout 1080 on a lower portion of a periphery of the power lens 1020 results in forces being translated to the membrane 1050 rather than the power lens optic 1040. By removing a lower portion of the periphery of the power lens 1020 (cutout 1080), the haptic 1015 engages primarily with an upper portion 1070 of the periphery of the power lens 1020 and forces are exerted primarily on the membrane 1050 (which is on the upper portion of the power lens 1020) rather than the power lens optic 1040 (which is on the lower portion of the power lens 1020), thereby affecting greater power change in the power lens 1020.

In the embodiment depicted in FIGS. 8A-8C, the accommodating intraocular lens may have a higher profile as compared to the embodiments depicted in FIGS. 9 and 10. In other words, in the high profile embodiments, the power lens is positioned closer to the open end of the haptic system 810 and farther away from the base lens 830 (FIGS. 8A-8C) and in the low profile embodiments, the power lens 920, 1020 is placed farther away from the open end and closer to the base lens 940, 1030 (FIGS. 9A-9C and FIGS. 10A-10D). The position of the power lens is represented in FIGS. 8C and 10D with reference to the distance $h_1$ of the peripheral edge of the power lens from the first edge of the outer periphery of the haptic.

Thus, in accordance with one aspect, the power lens is positioned at a predetermined distance from the first edge of the outer periphery of the haptic, as represented by $h_1$ in FIGS. 8C and 10D. In one aspect, the predetermined distance $h_1$ may be about 0 mm. about 0.1 mm, about 0.15 mm, about 0.2 mm, about 0.25 mm, about 0.30 mm, about 0.35 mm, about 0.40 mm, about 0.45 mm, about 0.50 mm, about 0.55 mm, about 0.60 mm, about 0.65 mm, about 0.70 mm, about 0.75 mm, about 0.80 mm, about 0.85 mm, about 0.90 mm, about 0.95 mm, about 1 mm, about 1.1 mm, about 1.15 mm, about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, about 1.7 mm, about 1.75 mm, about 1.8 mm, about 1.85 mm, about 1.9 mm, about 1.95 mm, and about 2 mm. In another aspect, the predetermined distance $h_1$ is may be provided within a range that is between and includes any two of the foregoing values. In a further aspect, the predetermined distance $h_1$ for a high profile accommodating IOL may be in the range of about 0 mm to about 0.75 mm. In yet a further aspect, the predetermined distance $h_1$ for a low profile accommodating IOL may be in the range of greater than 0.75 mm to about 1 mm.

The predetermined distance $h_1$ may also be provided as a percentage of the total height $h_2$ of the outer periphery of the haptic system 810, 1015. In one aspect, the predetermined distance $h_1$ may be about 0.01%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, and about 90% of the total height $h_2$ of the outer periphery of the haptic system 810, 1015. In another aspect, the predetermined distance $h_1$ may be provided within a range that is between and includes any two of the foregoing values. In a further aspect, the predetermined distance $h_1$ for a high profile accommodating IOL may be about 0.01% to about 37% of the total height $h_2$ of the outer periphery of the haptic system 810, 1015. In yet a further aspect, the predetermined distance $h_1$ for a high profile accommodating IOL may be about 38% to about 75% of the total height $h_2$ of the outer periphery of the haptic system 810, 1015.

Figure 11A:
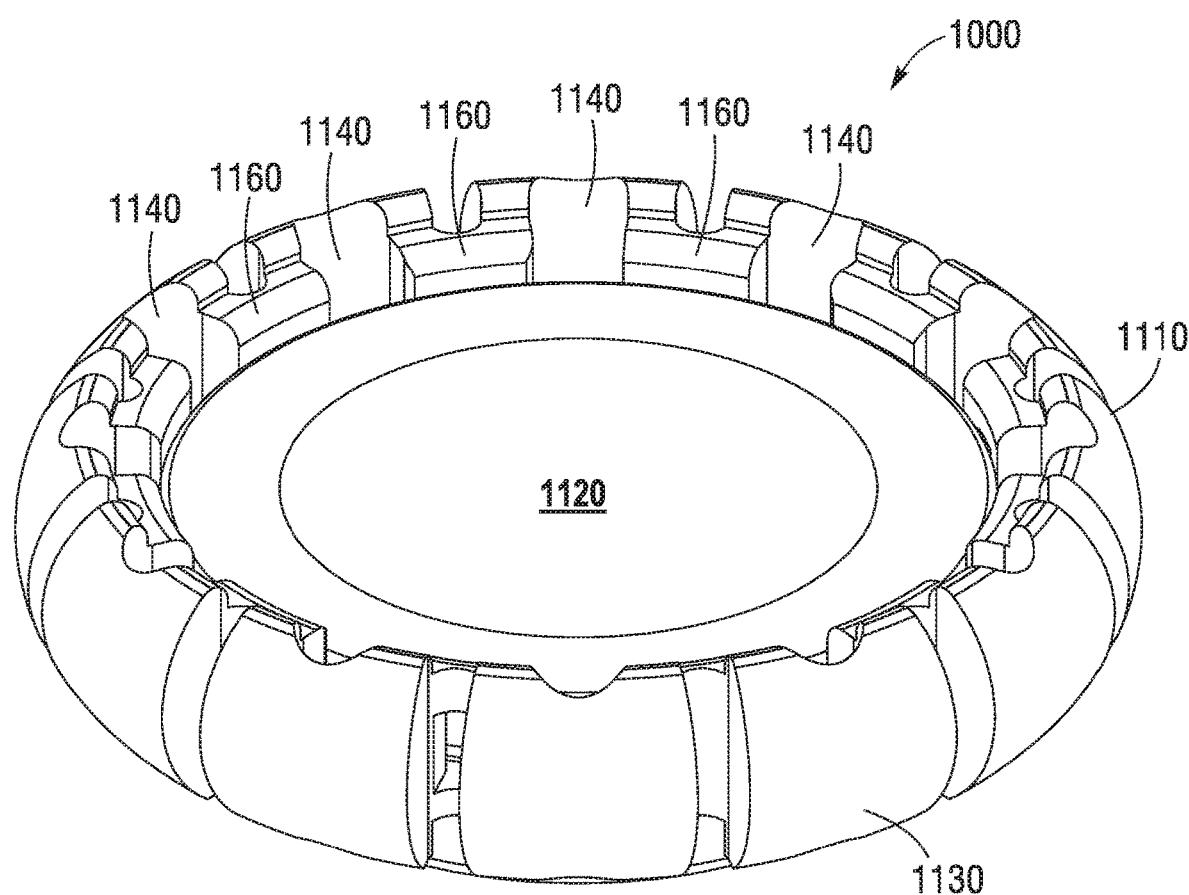
FIG. 11A depicts a perspective view of an accommodating IOL comprising a base assembly and a power lens having a fin-lock, in accordance with an embodiment of the present disclosure.
Figure 11B:
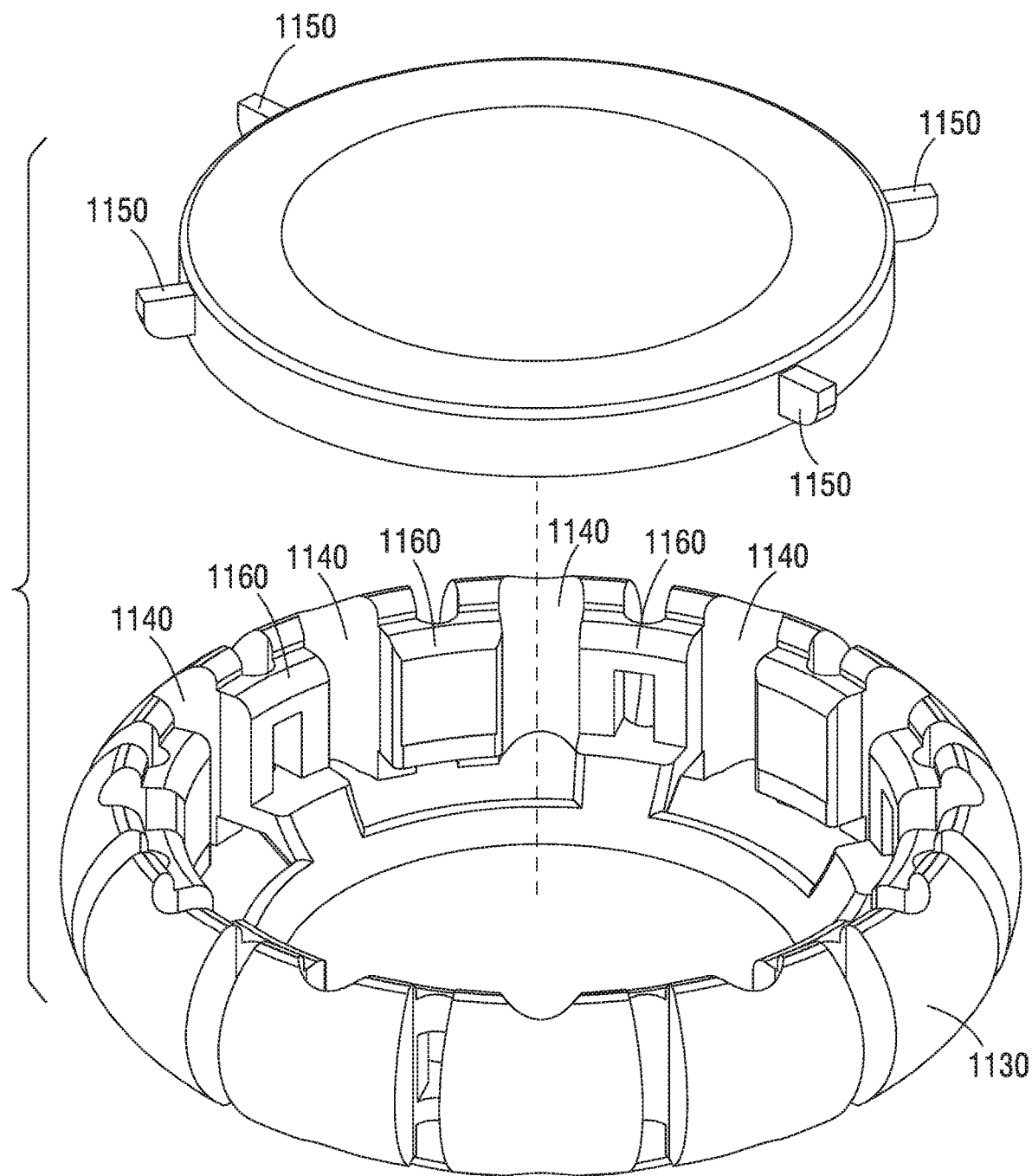
FIG. 11B depicts an exploded perspective view of the accommodating IOL of FIG. 11A.
Figure 11C:
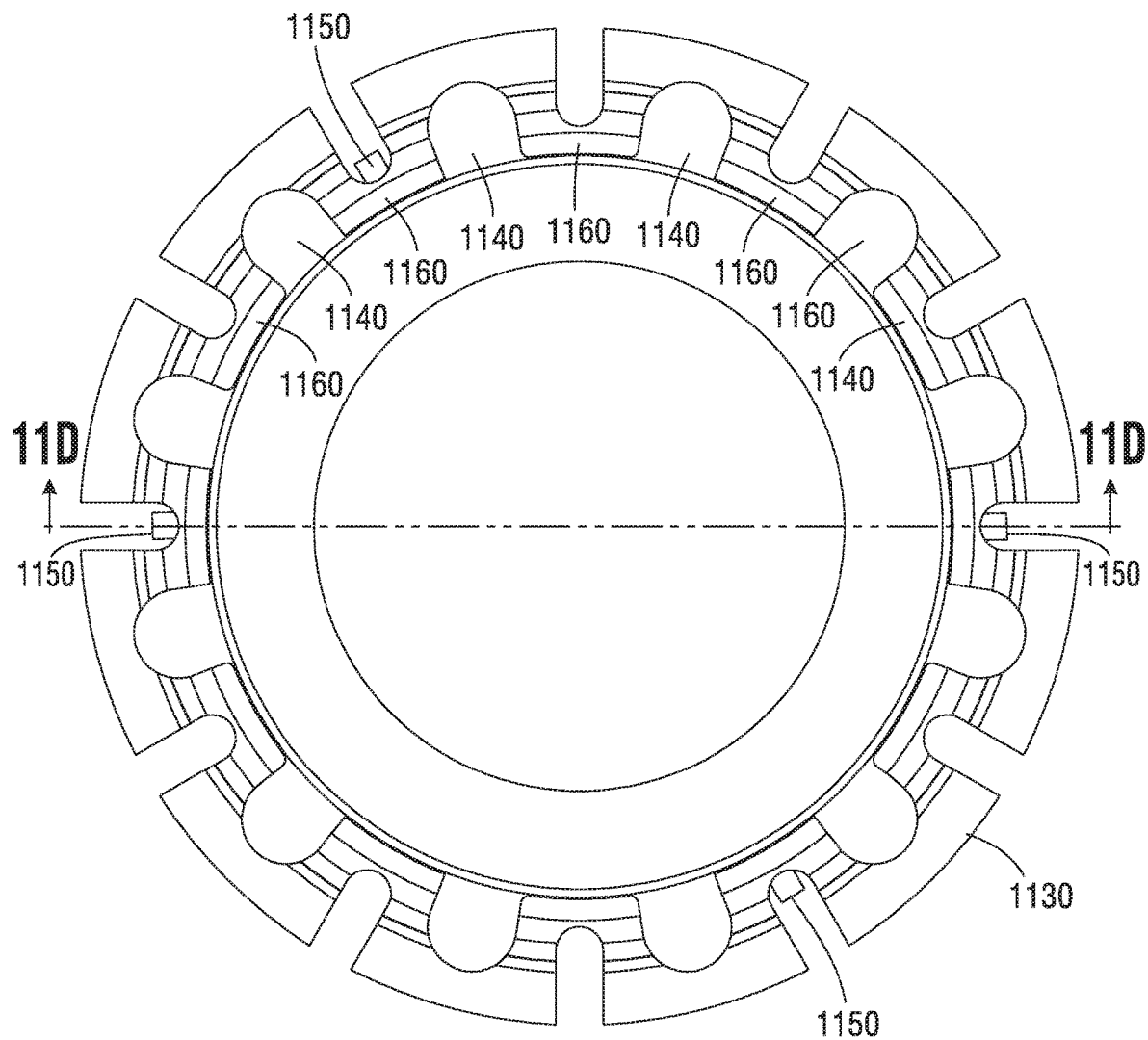
FIG. 11C depicts a top plan view of the accommodating IOL of FIG. 11A.
Figure 11D:
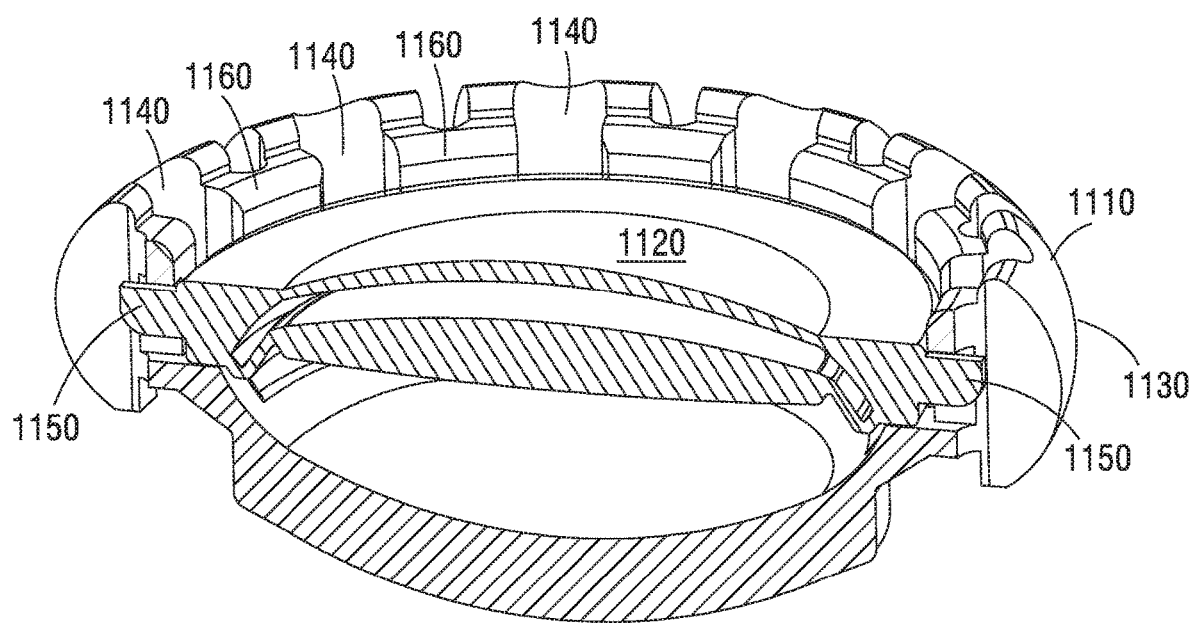
FIG. 11D depicts a cross-sectional view of the accommodating IOL of FIG. 11A.
Figure 12A:
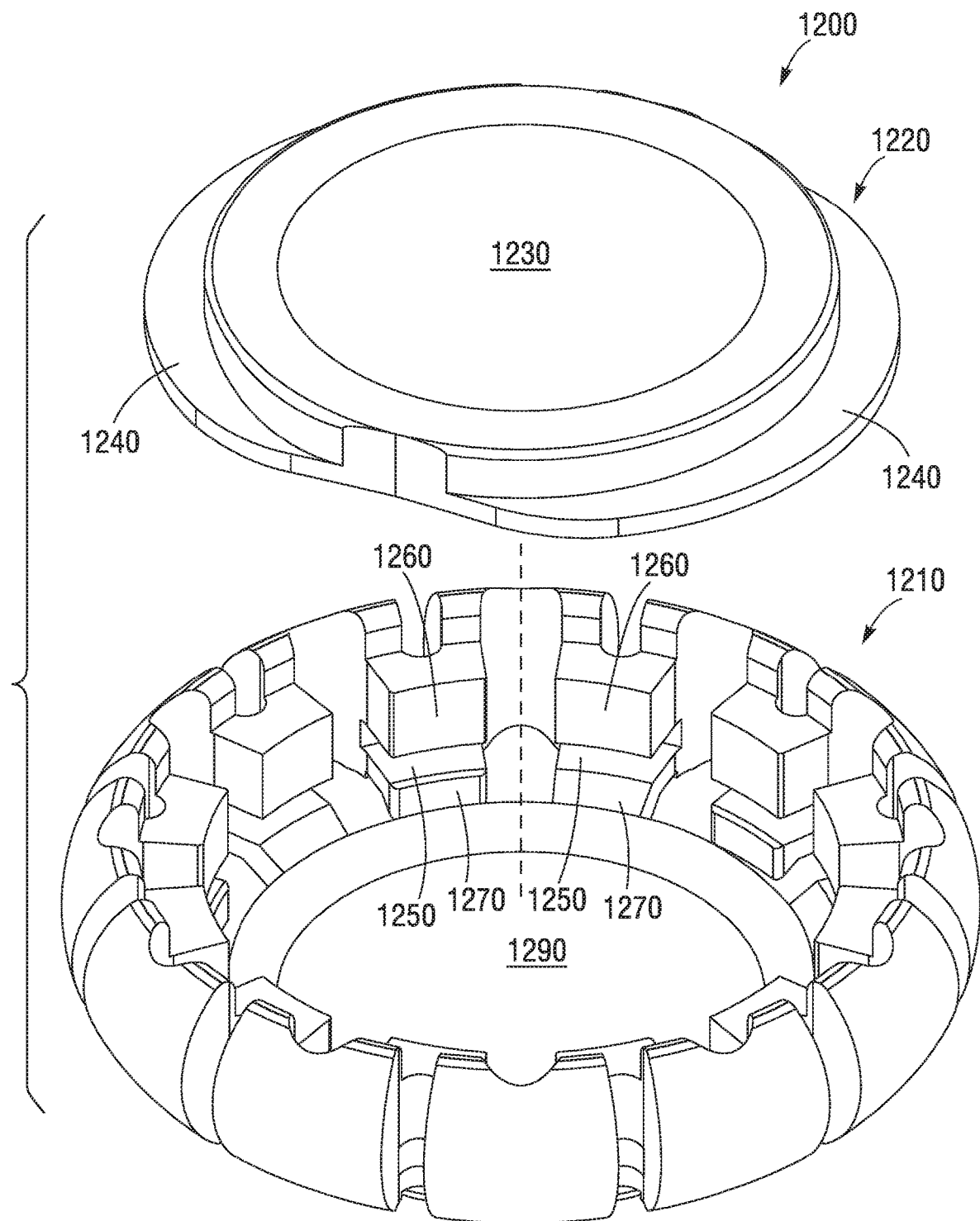
FIG. 12A depicts an exploded perspective view of an accommodating IOL having a base assembly and a power lens with a plate haptic, in accordance with an embodiment of the present disclosure.
Figure 12B:
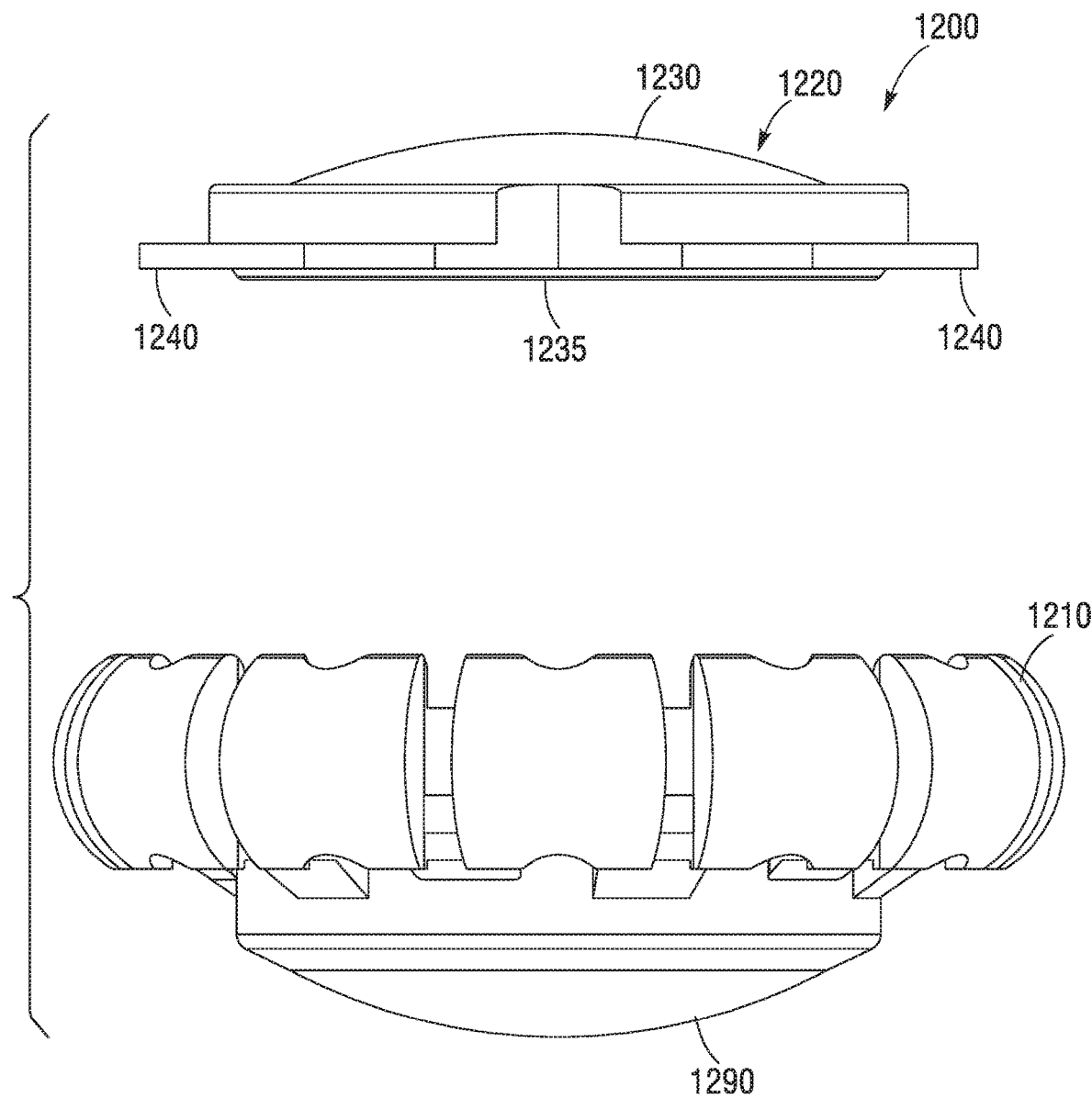
FIG. 12B depicts an exploded plan view of the accommodating IOL of FIG. 12A.
Figure 12C:
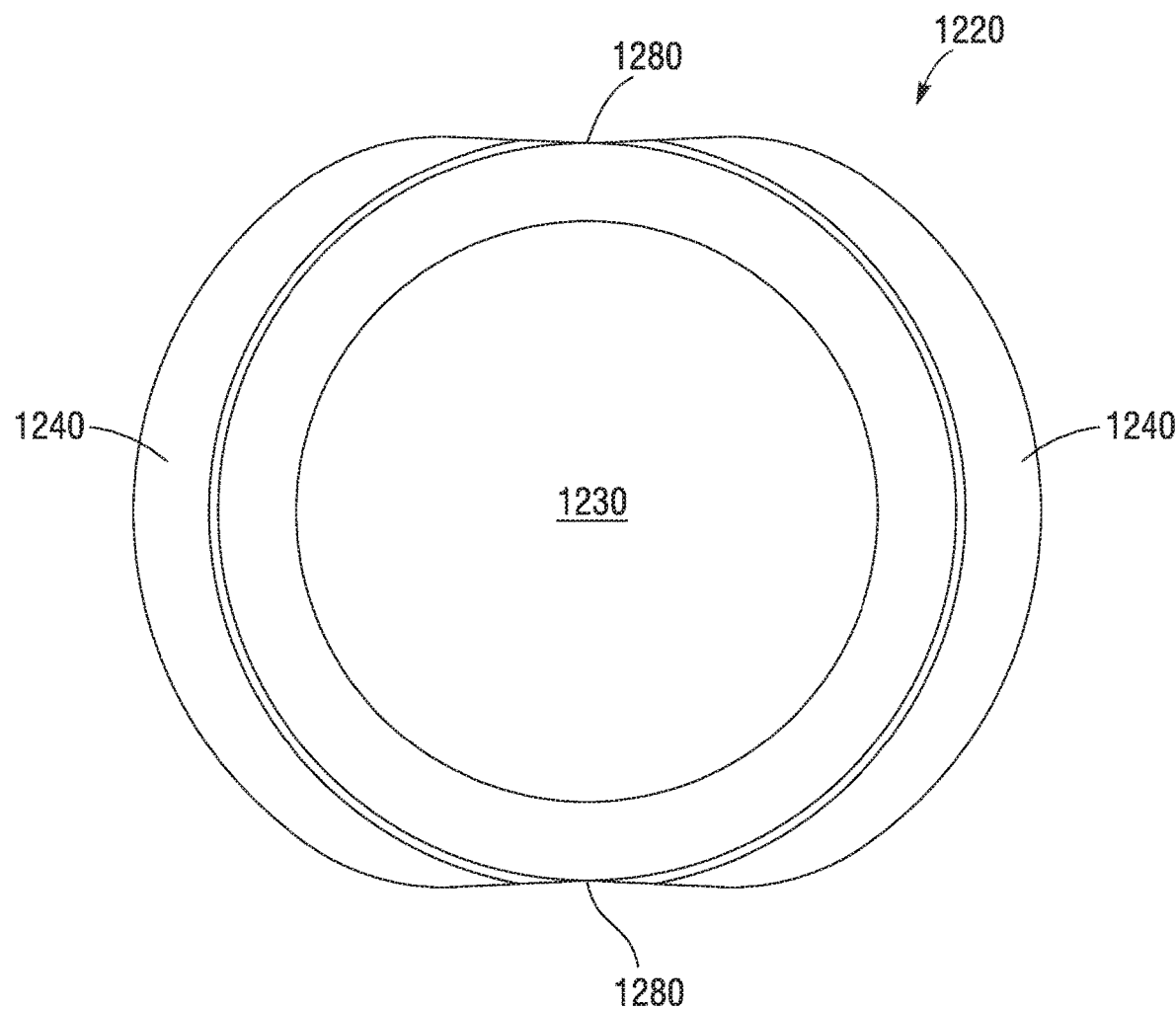
FIG. 12C depicts a top plan view of the power lens of the accommodating IOL of FIG. 12A.
Figure 12D:
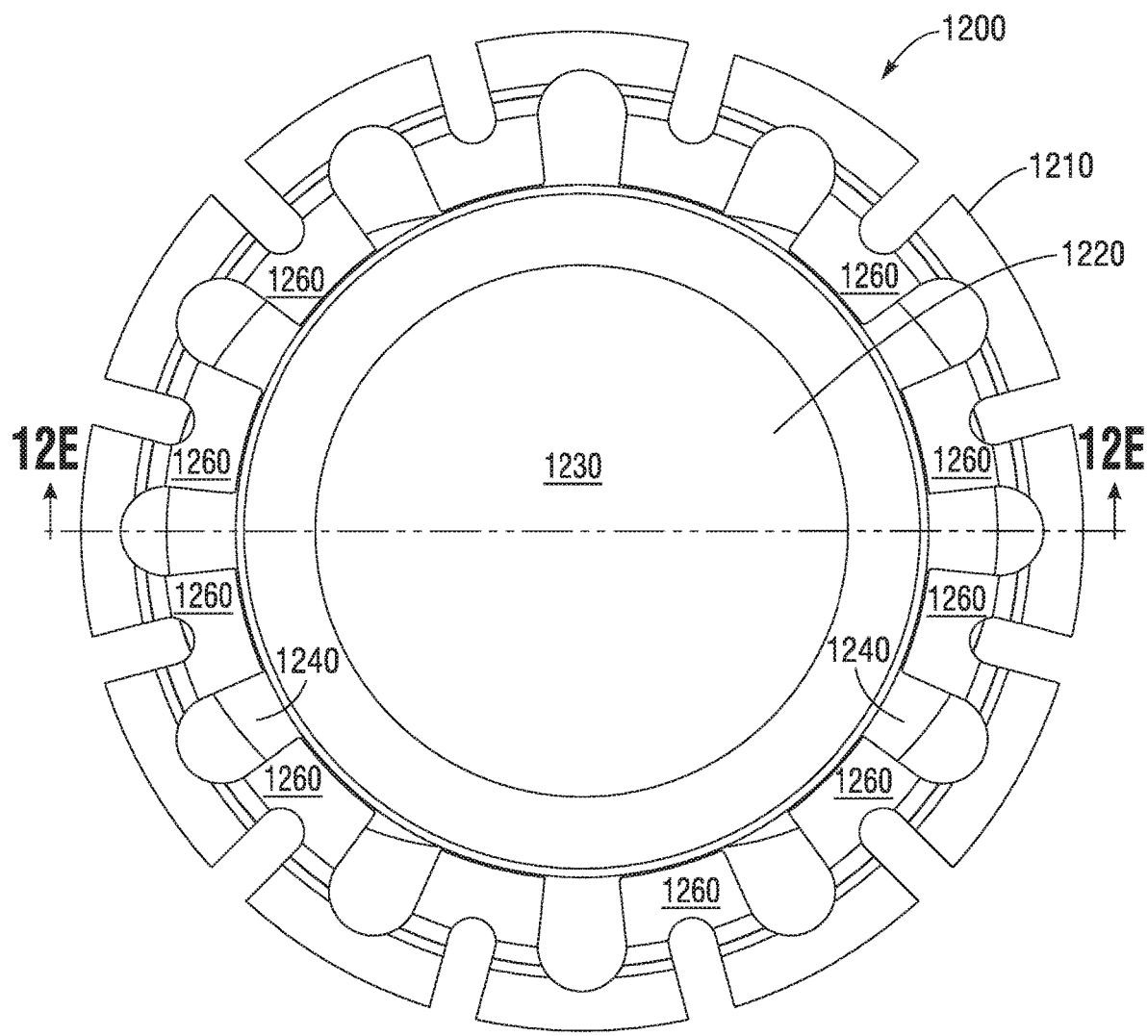
FIG. 12D depicts a top plan view of the accommodating IOL of FIG. 12A.
Figure 12E:
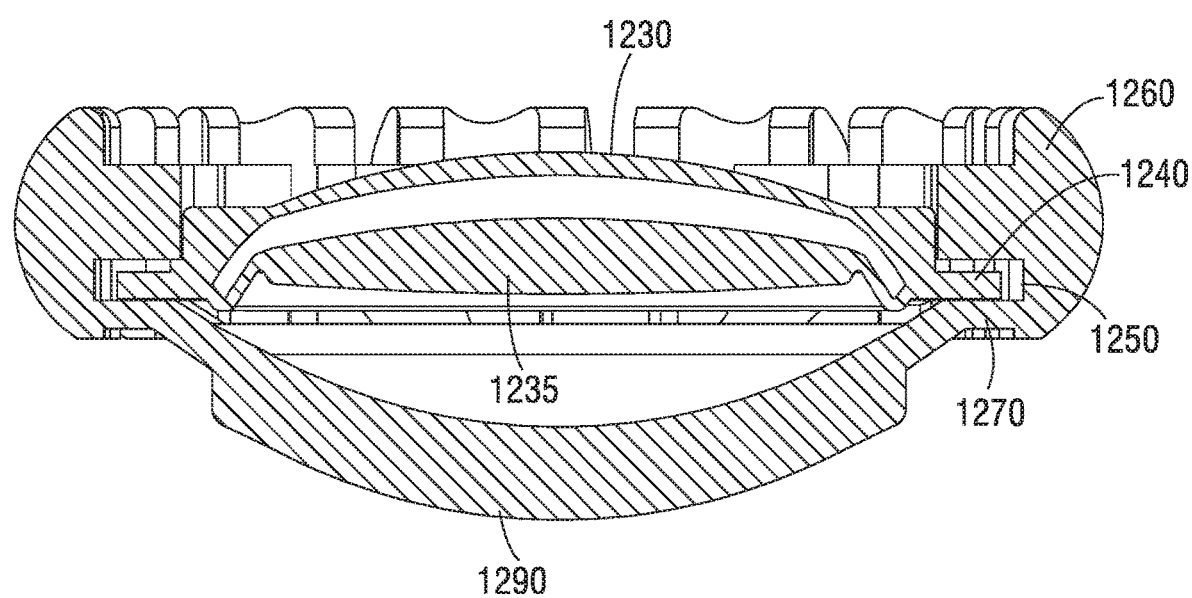
FIG. 12E depicts a cross-section view of the accommodating IOL of FIG. 12A.
Figure 12F:
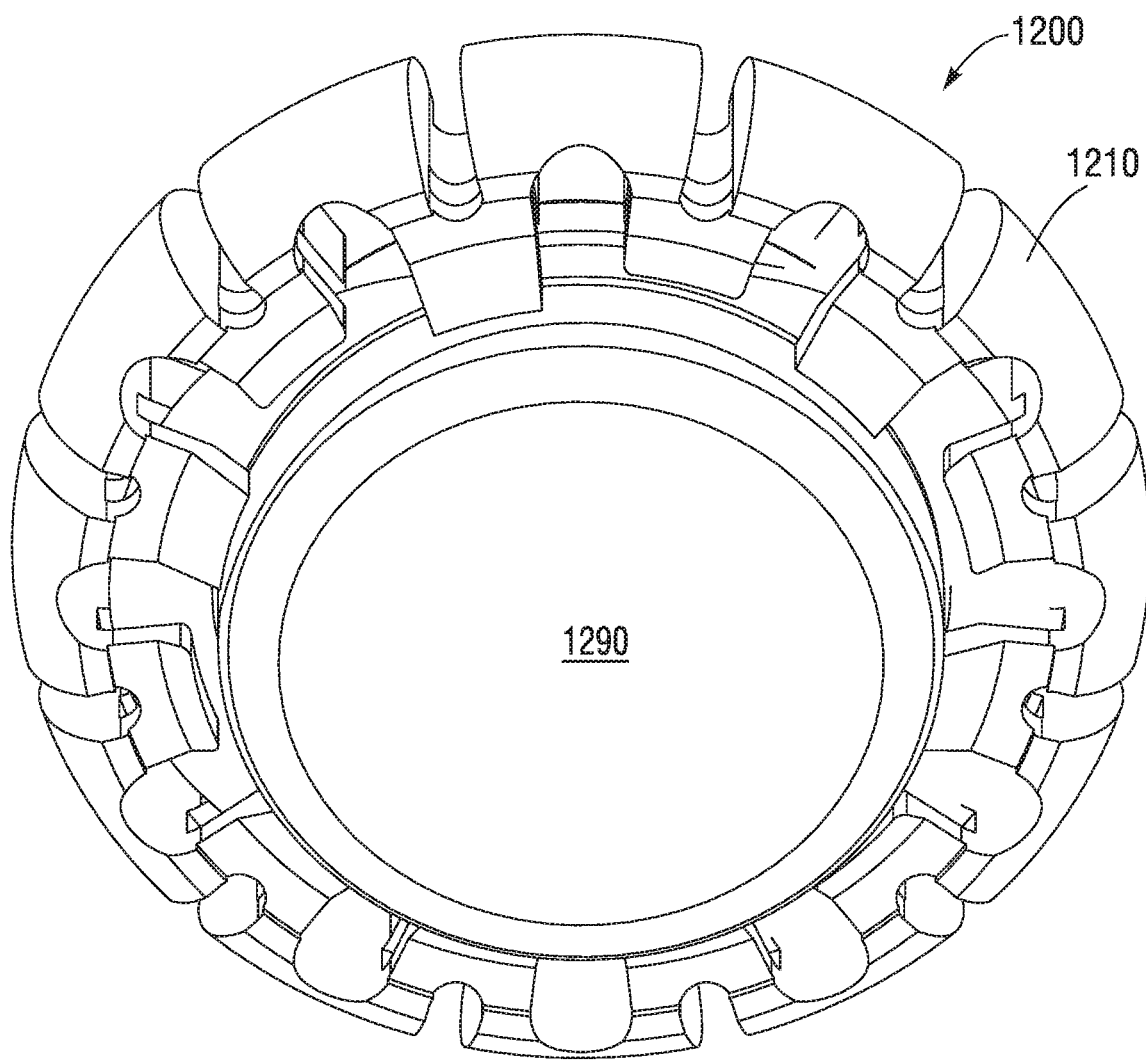
FIG. 12F depicts a bottom perspective view of the accommodating IOL of FIG. 12A.

FIG. 11A depicts a perspective view of an accommodating IOL 1100 including a base assembly 1110 and a power lens 1120, in accordance with an embodiment of the present disclosure. FIG. 11B provides an exploded view of the accommodating IOL 1100, FIG. 11C provides a top plan view of the accommodating IOL 1100, and FIG. 11D provides a cross-sectional view of the accommodating IOL 1100. The base assembly 1110 includes a haptic system 1130. As most clearly seen in FIG. 11C, the haptic system 1130 includes a plurality of recesses or cutouts 1140 defined within an inner periphery of the haptic system 1130 for receiving one or more fins 1150 extending from a peripheral edge of the power lens 1120. The plurality of recesses or cutouts 1140 may be defined by a raised portion or tab 1160 and an entry passage on at least one side of the raised portion. The power lens 1120 is lowered into the base assembly 1110 such that each of the fins 1150 enter in through one of the plurality of cutouts 1140. The power lens 1120 is then rotated, such that each fin 1150 is no longer positioned within one of the cutouts 1140, but rather, is positioned below one of a plurality of tabs 1160. Once each fin 1150 (or at least one of the fins 1150) is positioned below a tab 1160, the power lens 1120 becomes secured to the base assembly 1110. In certain embodiments, manipulation holes may be created on the power lens 1120 to allow a user to insert a tool into the one or more manipulation holes to assist in rotating the power lens 1120.

FIGS. 12A-12F provide various views of an accommodating IOL 1200, according to an embodiment of the present disclosure. In this embodiment, the accommodating IOL 1200 comprises a base assembly 1210 and a power lens 1220. The base assembly 1210 includes a base lens 1290. The power lens 1220 includes a flexible membrane 1230 and an optic 1235 and flanges 1240 that extend outwardly from a peripheral edge of the power lens 1220. The flanges 1240 can be inserted into a channel 1250 that is formed in the inner periphery of the base assembly 1240 or haptic by a plurality of upper tabs 1260 and lower tabs 1270. The positioning of the flanges 1240 towards the anterior portion of the power lens 1220 may be advantageous in that the flanges 1240 and the tabs 1260 securing the flanges 1240 are positioned such that they do not interfere with the visual elements of the accommodating IOL, i.e., the flexible membrane 1230, the optic 1235, and the base lens 1290. As such, visual artifacts or light distortions caused by the flanges and the tabs 1260, 1270 are minimized or eliminated altogether. The flanges 1240 do not extend out of the power lens 1220 at regions 1280 to allow for easier insertion of the power lens 1220 into the base assembly 1210.

Figure 13A:
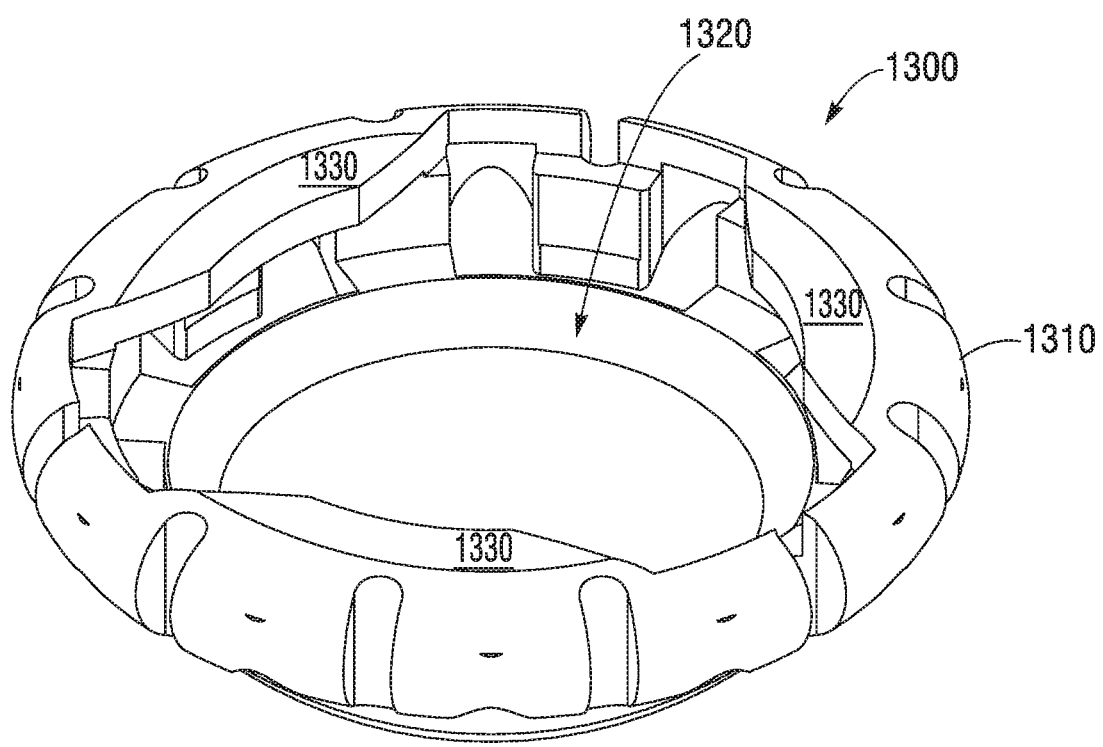
FIG. 13A depicts a perspective view of a base assembly having extended tabs, in accordance with an embodiment of the present disclosure.
Figure 13B:
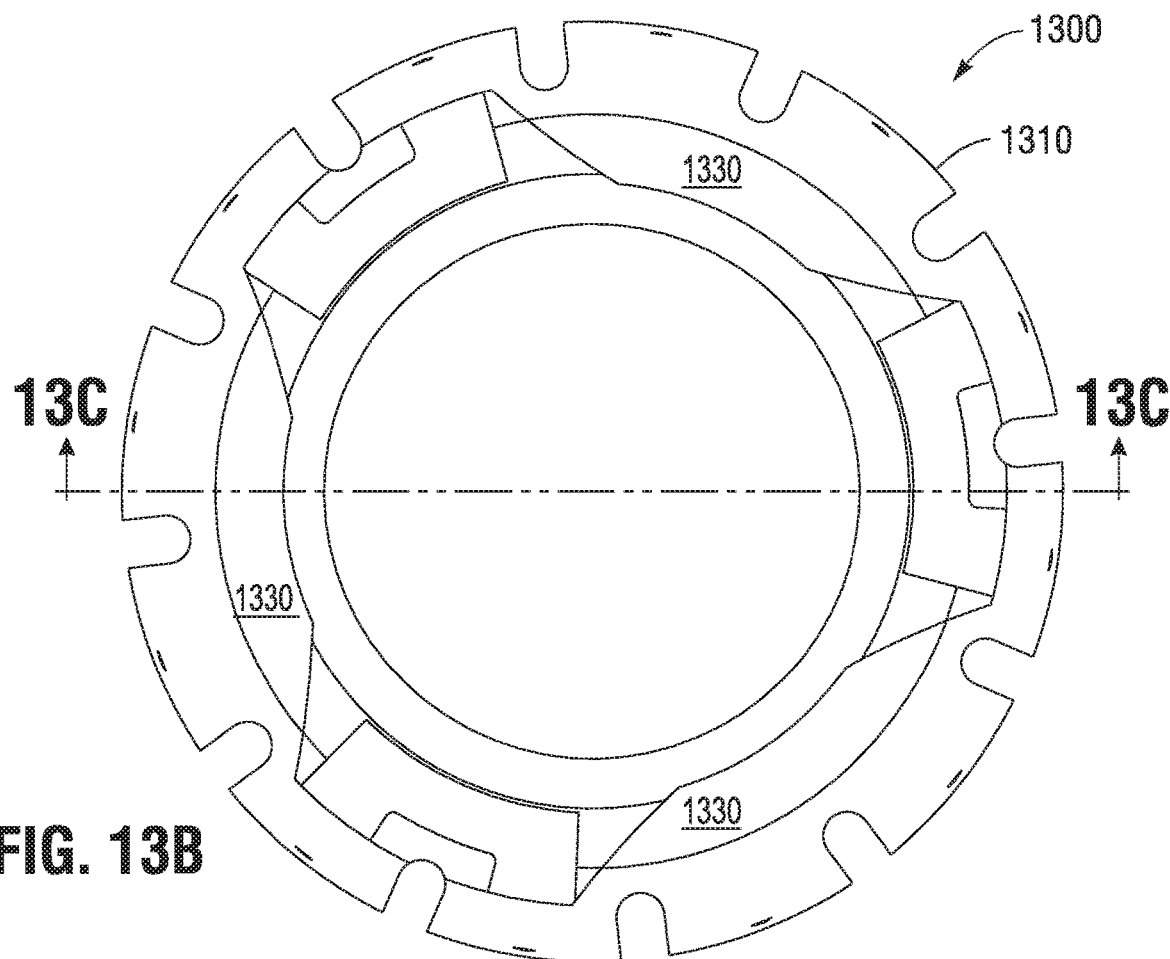
FIG. 13B depicts a top plan view of the base assembly of FIG. 13A.
Figure 13C:
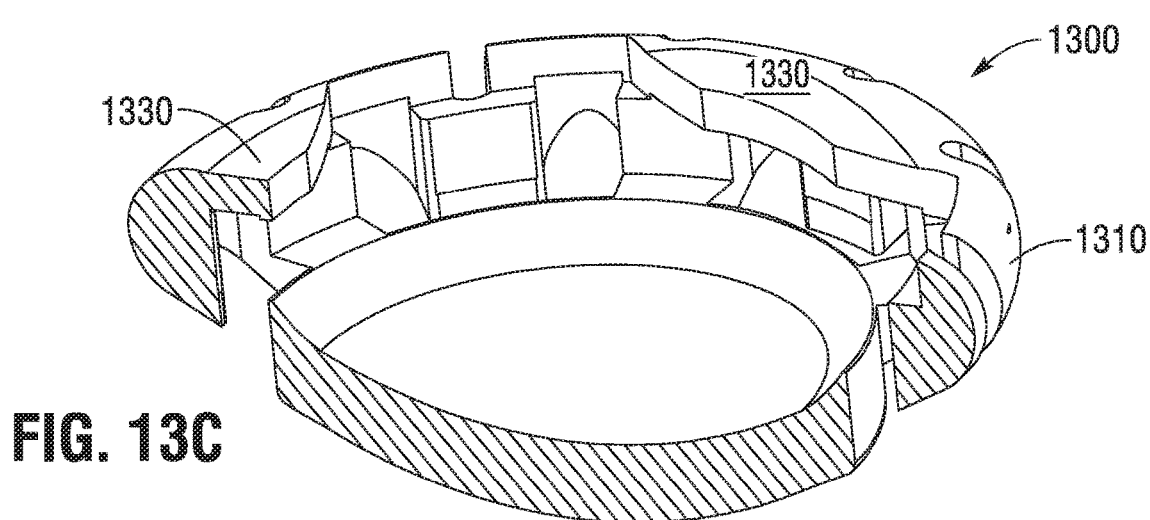
FIG. 13C depicts a cross-sectional view of the base assembly of FIG. 13A.

FIGS. 13A-13C depict an embodiment a base assembly 1300 with extended tabs for an accommodating IOL. The base assembly 1300 includes a haptic system 1310 and a cavity 1320 for receiving a power lens. Extended tabs 1330 extend over a portion of the circumference of the haptic system 1310 and into the cavity. The extended tabs 1330 are used to secure a power lens within the base assembly 1310. In certain embodiments, each tab 1330 may be measured by an angular coverage, indicative of the portion of the circumference encompassed by each tab 1330. In certain embodiments, each tab 1330 may encompass between 30 degrees and 180 degrees. Each tab 1330 may also include a width measurement, indicative of how far in towards the center of the base assembly the tab 1330 extends. An outer edge of the haptic system 1310 and applicable haptic systems described in this disclosure can be approximately 1 mm thick.

FIGS. 14A-D depict various views of an astigmatism-free base ring 1400, in accordance with an embodiment of the present disclosure. The astigmatism-free base ring 1400 is a fluid-filled base ring configured to receive a power lens in a manner as depicted with reference to FIGS. 1C and 3C. The astigmatism-free base ring 1400 includes a haptic system 1410 and may be provided as a ring shaped to enclose a region 1420. A power lens may be inserted into the region 1420 to form an accommodating IOL. The astigmatism-free base ring 1400 includes upper flanges 1430 and a lower surface 1435 to secure the power lens between the upper flanges 1430 and the lower surface 1435.

Figure 14A:
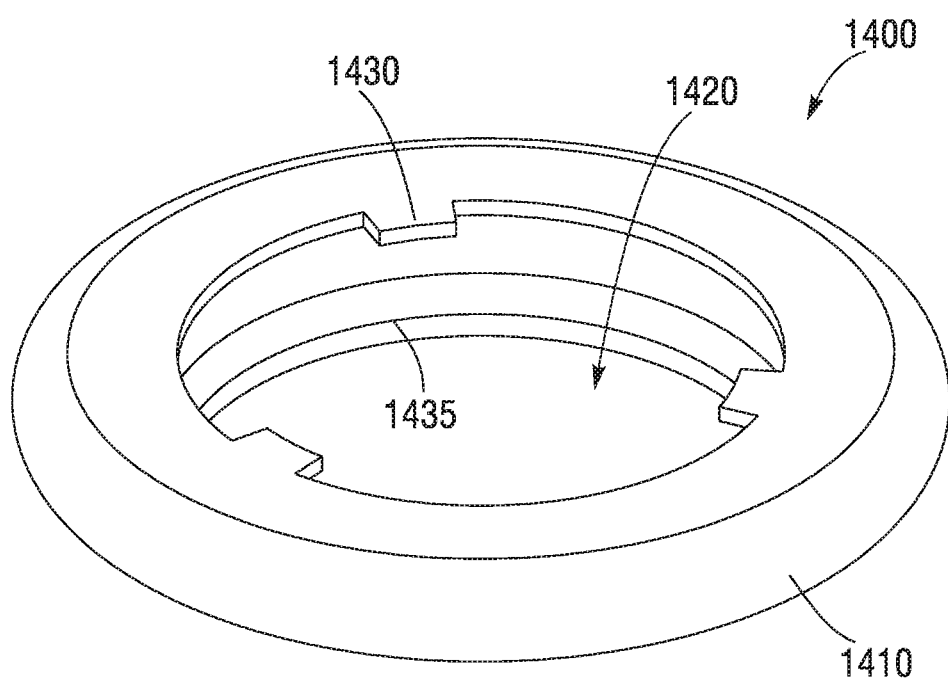
FIG. 14A depicts a perspective view of a base ring, in accordance with an embodiment of the present disclosure.
Figure 14B:
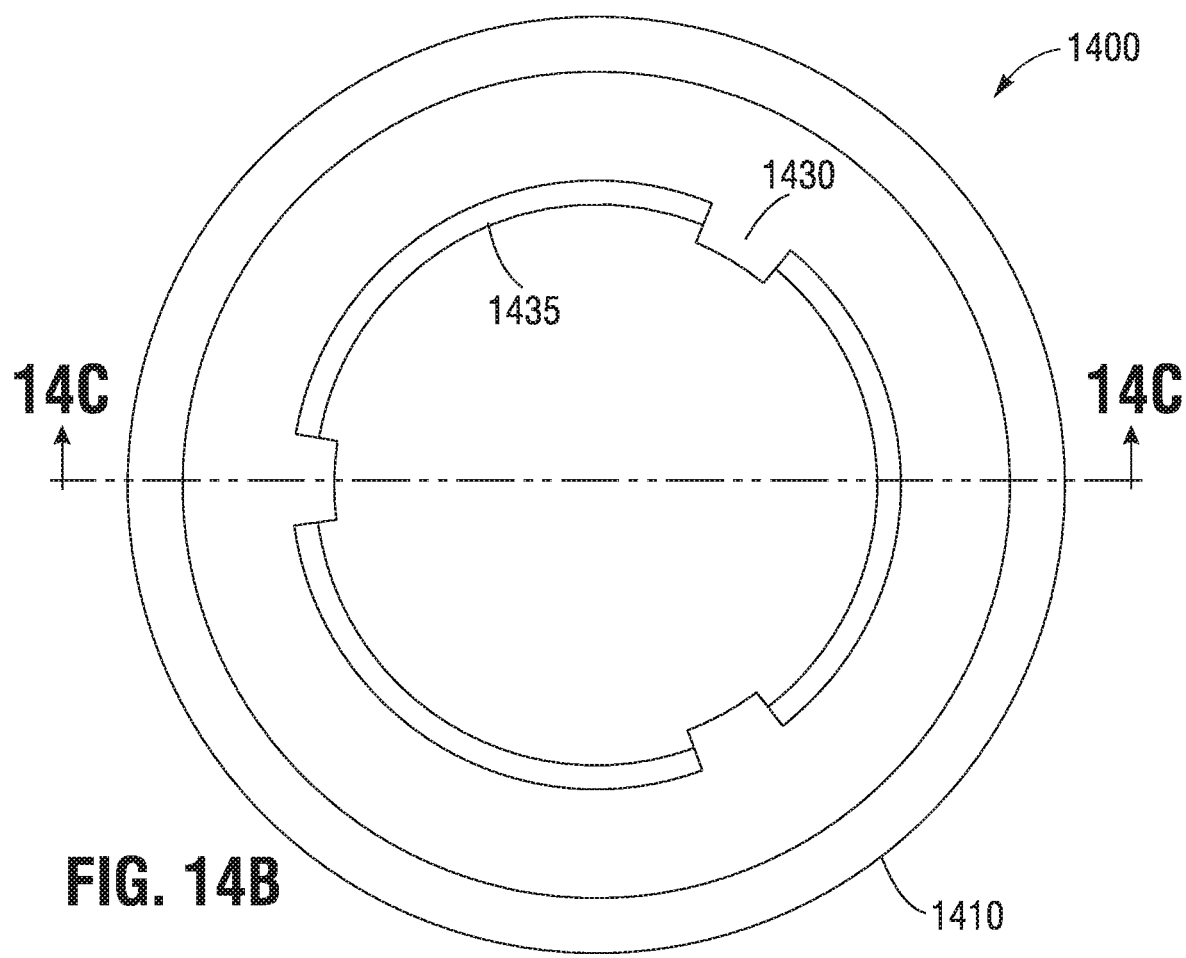
FIG. 14B depicts a top plan view of the base ring of FIG. 14A.
Figure 14C:
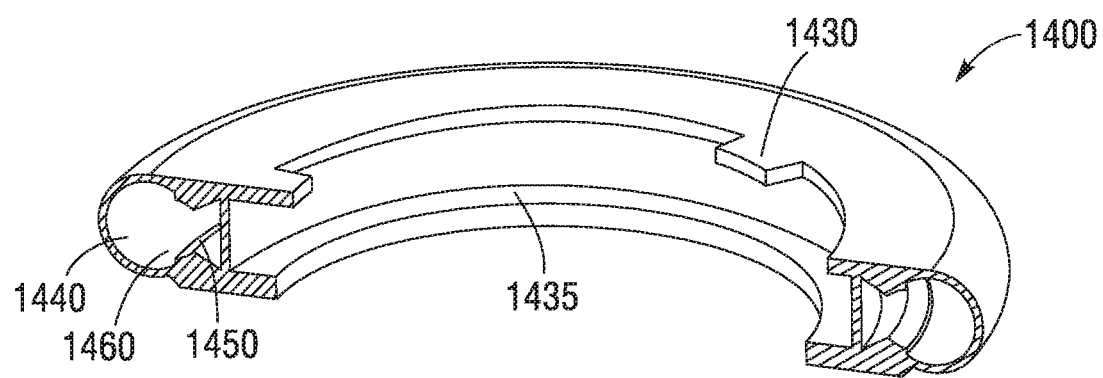
FIG. 14C depicts a cross-sectional view of the base ring of FIG. 14A.

FIG. 14C provides a cross-sectional view of the astigmatic free base ring 1400. The astigmatism-free base ring 1400 may include an outer reservoir 1440 and an inner reservoir 1450. The outer reservoir 1440 and the inner reservoir 1450 may contain a fluid, and may be in fluid communication with one another. In one embodiment, the outer reservoir 1440 and the inner reservoir 1450 may be provided in fluid communication with one another through a channel 1460 that is narrower than at least one of the outer reservoir 1440 and the inner reservoir 1450. The use of the two reservoirs 1440, 1450 in fluid communication with one other through a narrowed channel 1460 more evenly distributes a radially-compressive force onto the inner surface of the base ring 1400 that is located between the upper flange 1420 and the lower surface 1435 when a radially compressive force applied to the periphery of the haptic system 1410. As such, a more even, non-toric deformation is created in the accommodating IOL.

Figure 14D:
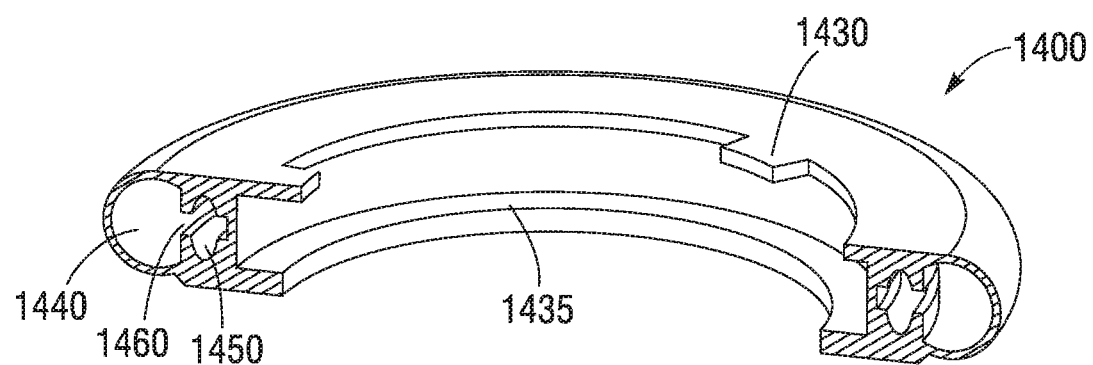
FIG. 14D depicts an alternative cross-sectional view of the base ring of FIG. 14A.
Figure 14E:
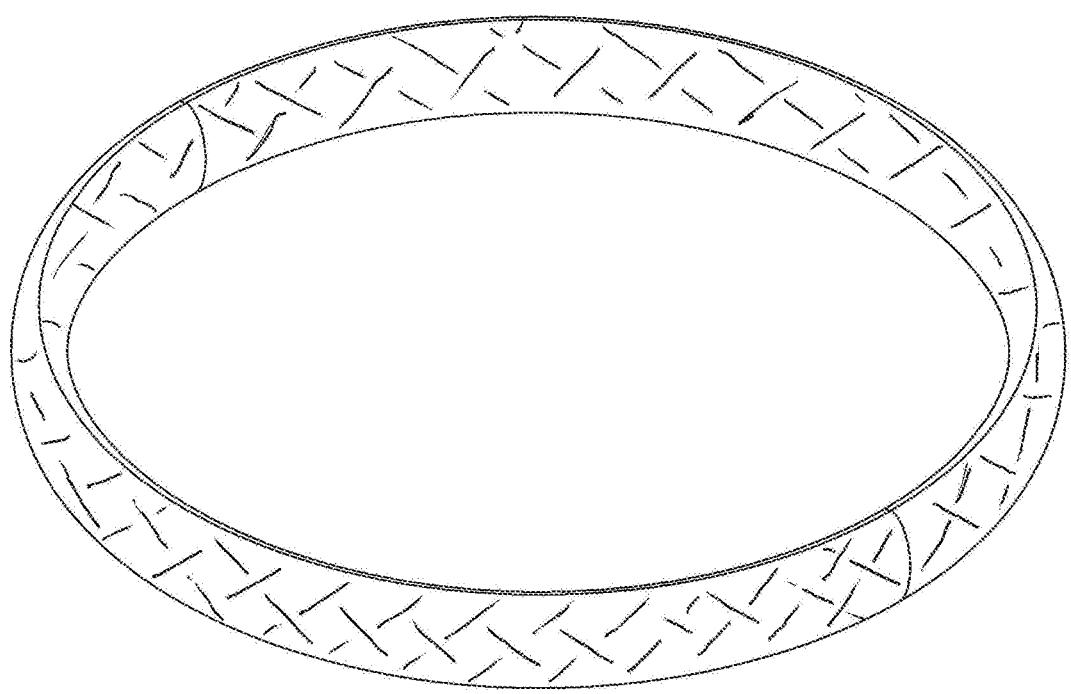
FIG. 14E depicts a perspective view of a mesh braid that may be incorporated into the base ring of FIG. 14D.

FIG. 14D provides a cross-sectional view of an alternative embodiment of the astigmatism-free base ring 1400. In certain embodiments, a mesh braid, such as that shown in FIG. 14E, may be incorporated into the inner reservoir 1450. In certain embodiments, the mesh braid may comprise a Nitinol braid. The mesh braid (FIG. 14E) may allow for fluid to flow between the inner and outer reservoirs 1450, 1440, while providing additional structure support for the inner reservoir, thereby facilitating even disbursement of forces applied to the astigmatism-free base ring 1400. Thus, in one embodiment, the base ring 1400 described above may further comprise a porous support structure or a mesh braid, such as the one depicted in FIG. 14E, which may be disposed along a portion of or along an entirety of the inner reservoir 1450.

Figure 15A:
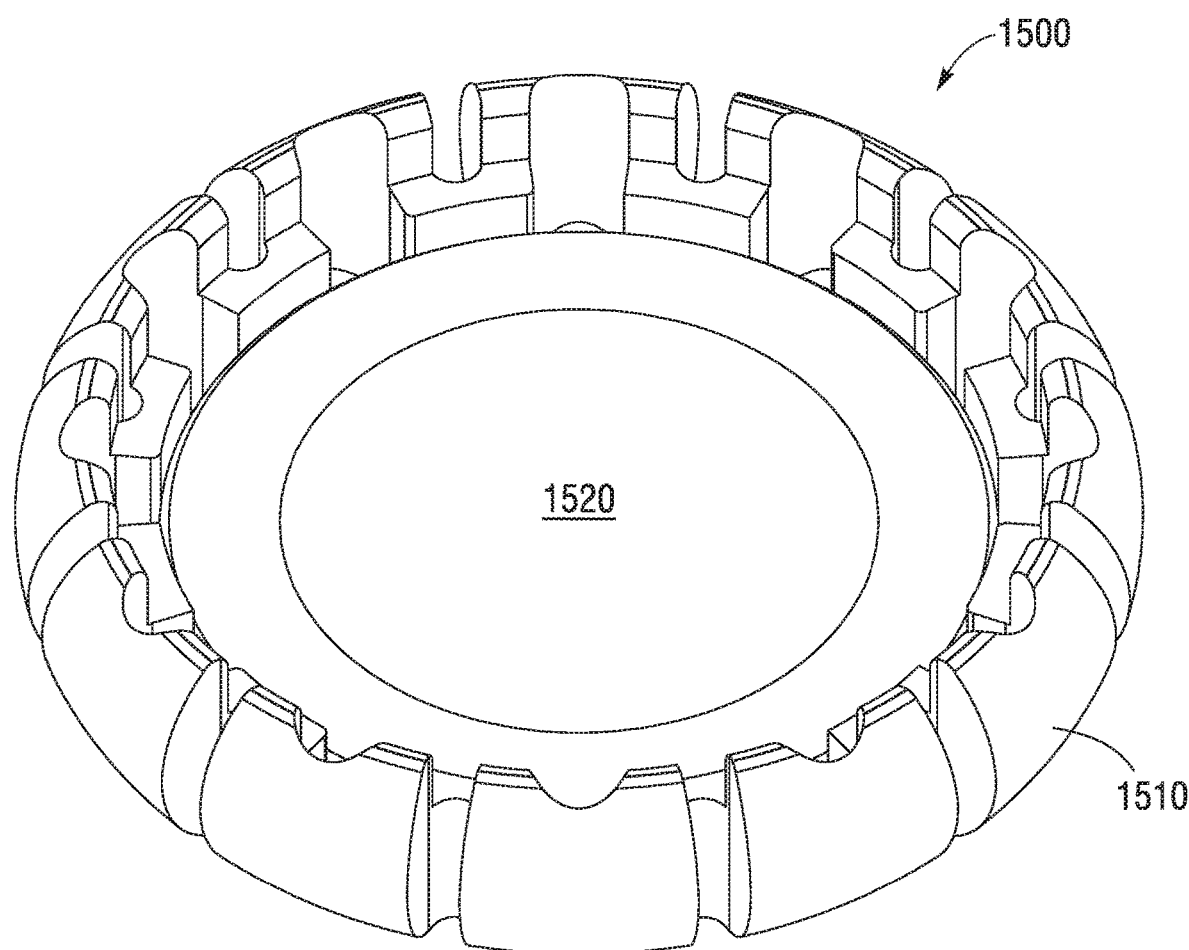
FIG. 15A depicts a perspective view of an accommodating IOL having a one-piece base assembly and a power lens, in accordance with an embodiment of the present disclosure.
Figure 15B:
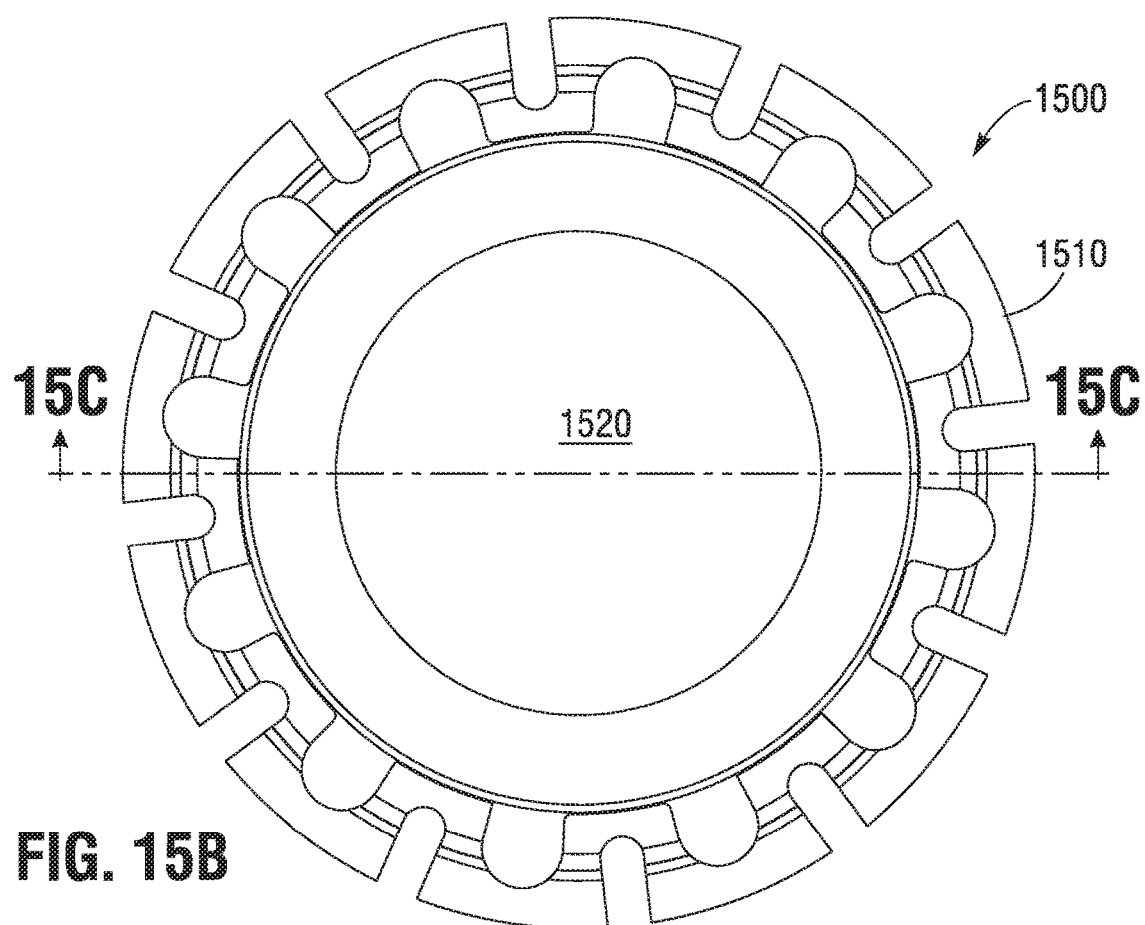
FIG. 15B depicts a top plan view of the accommodating IOL of FIG. 15A.
Figure 15C:
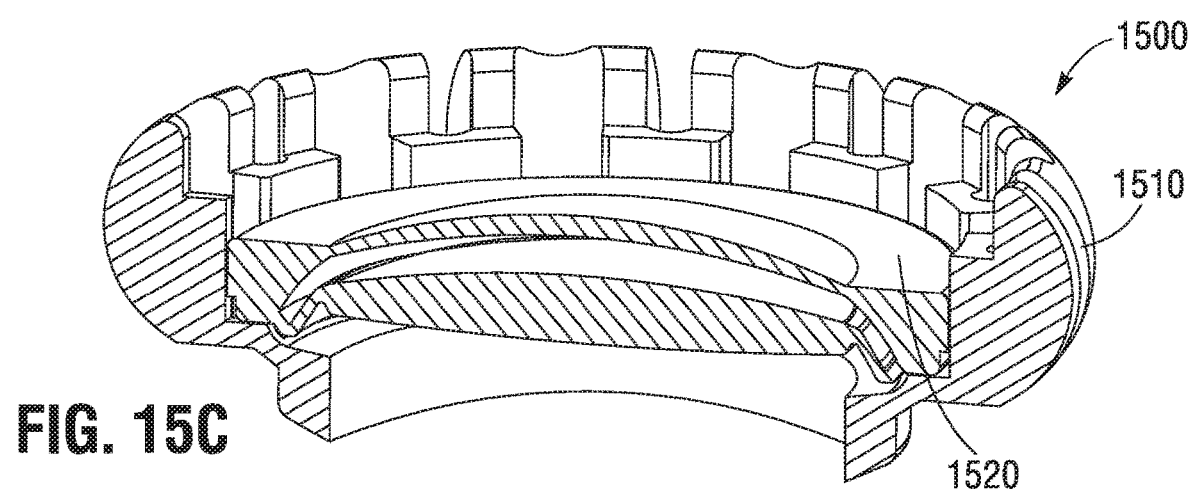
FIG. 15C depicts a cross-sectional view of the accommodating IOL of FIG. 15A.
Figure 15D:
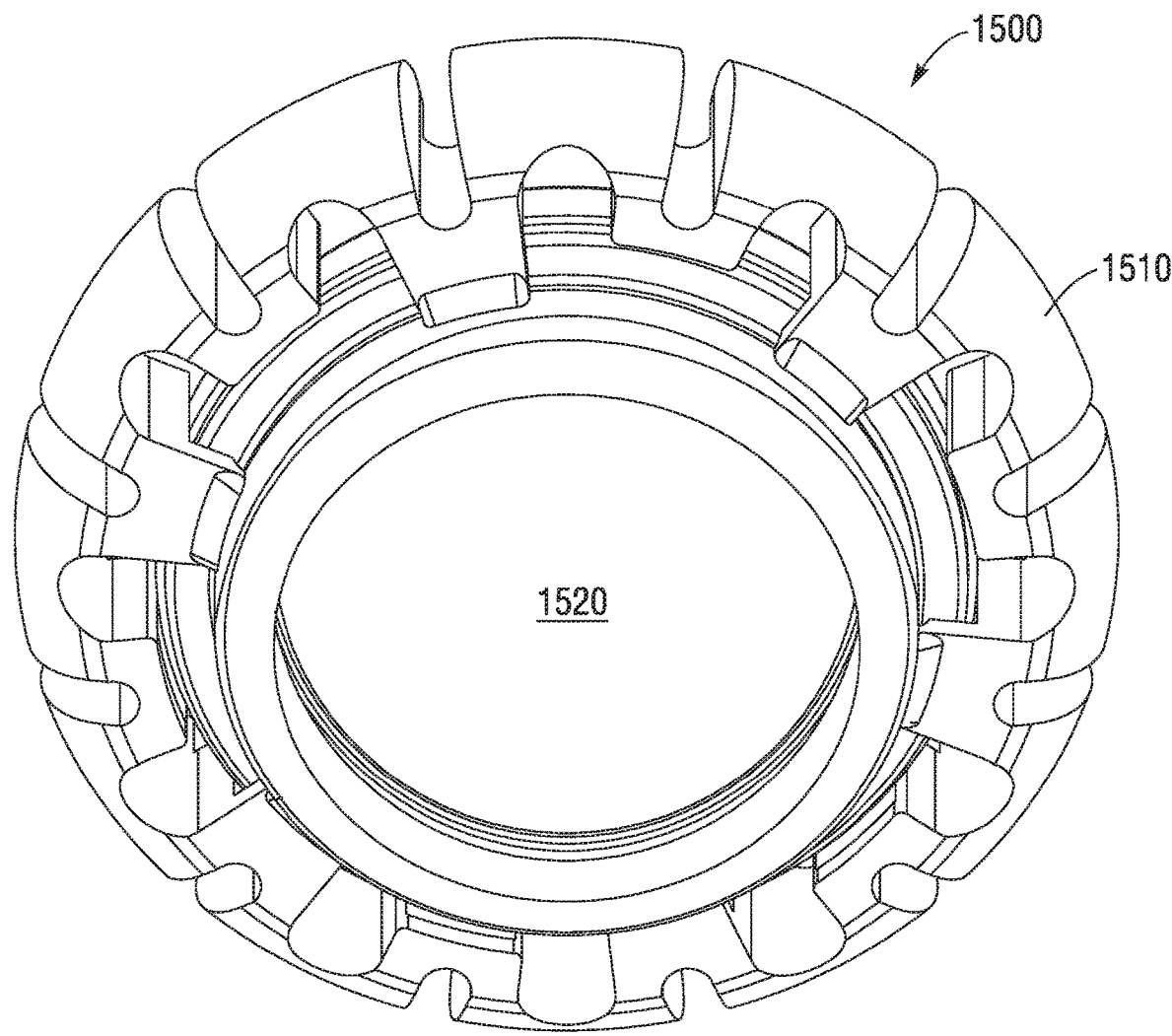
FIG. 15D depicts a bottom perspective view of the accommodating IOL of FIG. 15A.
Figure 16A:
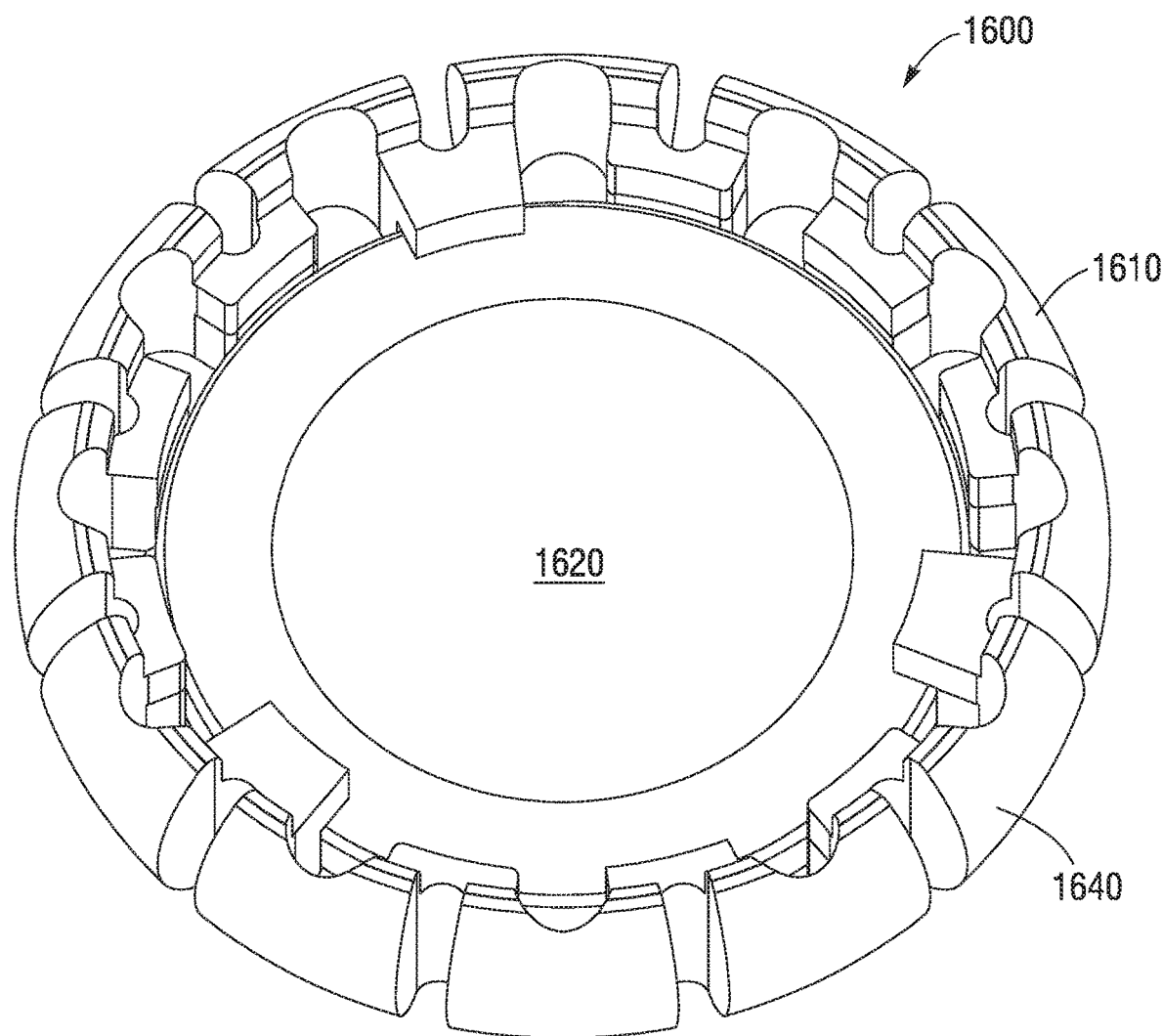
FIG. 16A depicts a perspective view of an accommodating IOL having a no gap base assembly, in accordance with an embodiment of the present disclosure.
Figure 16B:
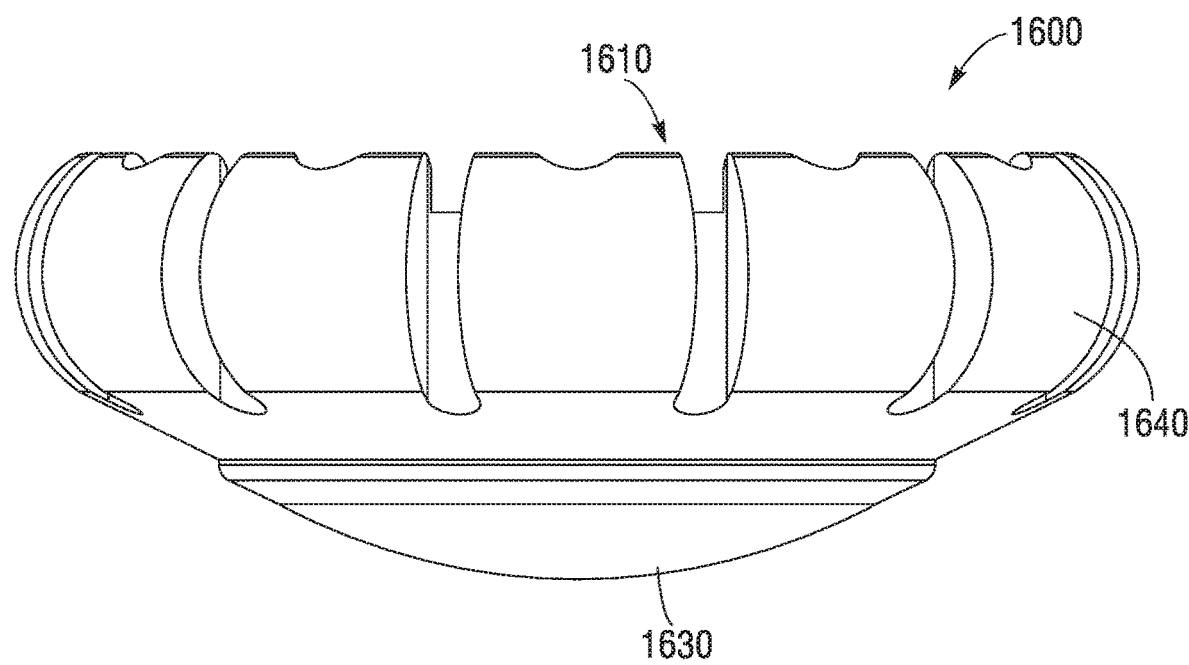
FIG. 16B depicts a side plan view of the accommodating IOL of FIG. 16A.
Figure 16C:
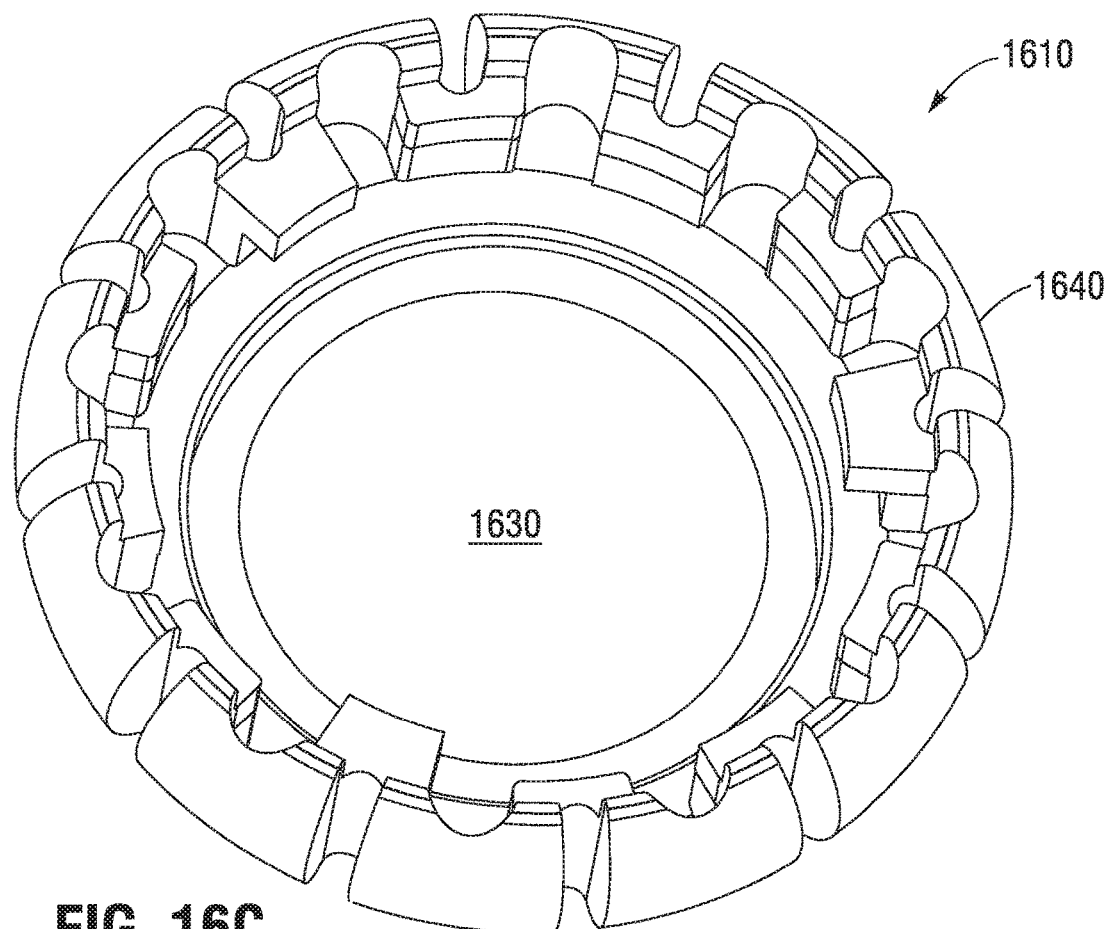
FIG. 16C depicts a perspective view of a no gap base assembly that may be utilized in the accommodating IOL of FIG. 16A.
Figure 16D:
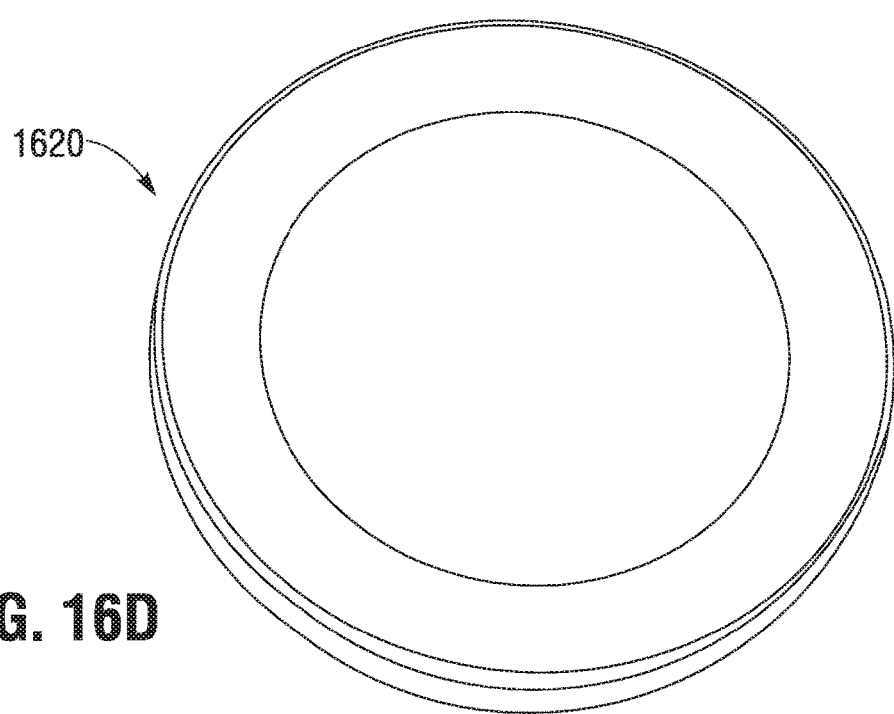
FIG. 16D depicts a perspective view of a power lens that may be utilized in the accommodating IOL of FIG. 16A.
Figure 16E:
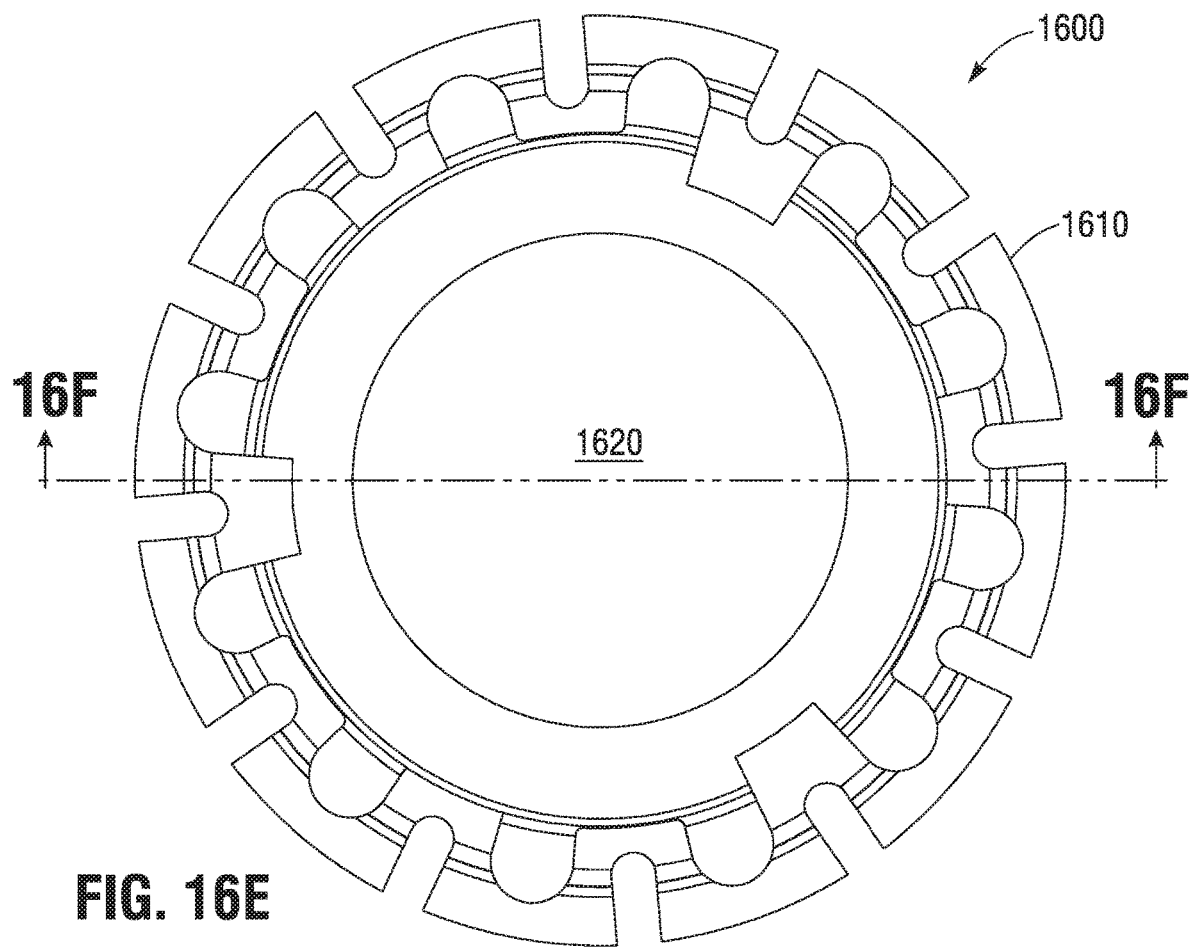
FIG. 16E depicts a top plan view of the accommodating IOL of FIG. 16A.
Figure 16F:
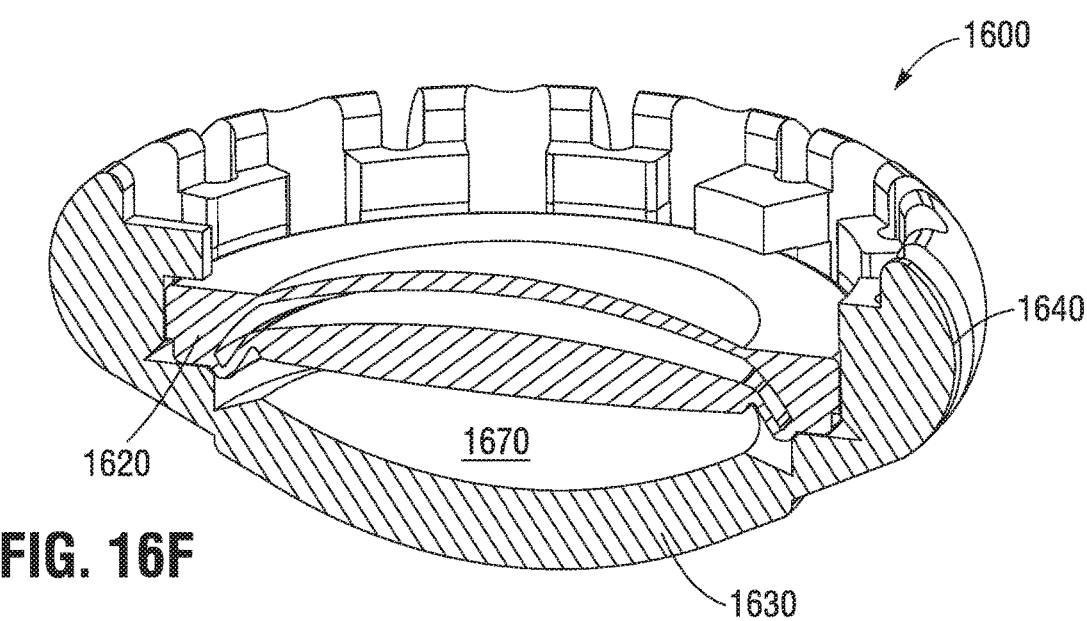
FIG. 16F depicts a cross-sectional view of the accommodating IOL of FIG. 16A.

FIG. 15A depicts a perspective view of an accommodating IOL 1500 having a base assembly and power lens that is attached or attachable to one another by bonding or insert molding. FIG. 15B provides a top plan view of the accommodating IOL 1500. FIG. 15C depicts a cross-sectional view of the accommodating IOL 1500. FIG. 15D depicts a bottom perspective view of the accommodating IOL 1500. The accommodating IOL 1500 includes a haptic base assembly 1510 attached to a power lens 1520 during manufacture. The attachment may be effectuated by one or both of bonding or insert molding, in which one of the base assembly 1510 and the power lens 1520 is molded and then the other of the base assembly 1510 and the power lens 1520 is molded directly onto the first molded part (i.e., the base assembly 1510 or the power lens 1520). The portion of the power lens 1520 that is attached to the base assembly 1510 may be one or both of a portion of the circumferential peripheral edge 1522 or a posterior edge 1524 of the power lens 1520. The entire accommodating IOL 1500 can then be inserted into a patient. In order to reduce the bulk of the bonded base and power lens, the accommodating IOL 1500 can include just a single optic, such that power correction comes only from the power lens 1520. Thus, in one embodiment, the base assembly 1510 itself does not comprise an optic that provides refractive correction and the IOL 1500 only comprises the power lens 1520 to provide refractive correction.

FIGS. 16A-F depict various views a no gap accommodating IOL 1600 including a gapless base assembly 1610 and a power lens 1620. The gapless base assembly 1610 includes a base lens 1630 and a haptic system 1640. The base lens 1630 and the haptic system 1104 are secured together so no gaps are formed leading into the power lens 1620. This limits the ability of cells to flow into a cavity 1670 between the base lens 1630 and the power lens 1620 when a power lens 1620 is inserted into the gapless base assembly 1610. In various embodiments, a similar effect may be had by applying a Parylene coating a base assembly having gaps to prevent cell migration into and out of the cavity between the power lens and the base lens.

In various embodiments, the base assemblies described in this paper can provide a portion of power correction. As a result, a base assembly can be installed and an appropriate power lens to install can be selected to allow for correction within ¼ of a diopter. Further, in various embodiments, an optic of the base assemblies can include a UV absorber or UV absorbent coating to absorb UV entering the eye of the patient. In various embodiments Purkinje images can be used to adjust a power lens or a base assembly to ensure that they are properly installed during the installation of the accommodating IOL.

In various embodiments, through the use of a power lens and a base assembly, such as the base assemblies described in this disclosure, the two-part accommodating IOLs disclosed herein allow for greater efficiency in cataloguing products. For example, 4 base assemblies and 9 power lenses are needed to cover a range of 12 to 27.5 diopters at half diopter steps. Using single lenses requires 32 different lenses. As only 4 base assemblies and 9 power lenses are needed, only 13 stock keeping units (hereinafter referred to as "SKUs") are needed to store and organize the power lenses and base assemblies as opposed to 32 different SKUs. This reduces chances of misplacement and leads to easier organization. This increase in efficiency is even greater with respect to toric lenses. For example, assuming 4 different toric powers, for 32 single lens types, 128 SKUs are need to organize the lenses. However, with a two-part accommodating IOL, assuming 4 different toric powers of the base assemblies, only 16 base assemblies and 9 power lenses are needed, for a total of 25 SKUs, which is dramatically less than the 128 SKUs needed for single toric lenses.

In various embodiments, the tabs and the flanges of the base assemblies discussed in this paper can be colored differently than a power lens to allow a surgeon to see when a power lens has been correctly inserted into a base assembly. In various embodiments, a power lens or an edge of a power lens can be colored to further aid in insertion of the power lens into a base assembly. In various embodiments a base lens or a haptic system of a base assembly can be colored. Coloration can be achieved by adding roughness or a coating to outer surfaces of any of the previously described components.

In various embodiments, Purkinje images may be utilized to assist in adjustment and placement of a power lens into a base assembly. Images can be used to adjust the power lens and base lens after implantation to assure the best fit. This approach gives immediate and simple feedback for the surgeon through the eye piece of a scope. For example, a surgeon can receive an indication that a power lens is correctly placed into a base lens if the surgeon can see a perfect circle when looking through the scope. If the circle is deformed or misshaped at all, the surgeon will know that they have to continue adjusting the power lens.

What is claimed is:

1. An accommodating intraocular lens device comprising:
    a base assembly comprising a first open end, a second end coupled to a base lens, and a haptic surrounding a central cavity, wherein the haptic comprising an outer periphery, an inner surface and a height between a first edge and a second edge; and
    a power lens configured to fit within the central cavity, the power lens comprising a first side, a second side, a peripheral edge coupling the first and second sides, and a closed cavity configured to house a fluid;
    wherein the first side of the power lens is configured to be inserted into the eye separately from the base assembly and configured to be positioned within the cavity after being inserted into the eye at a predetermined distance from the first edge of the haptic.

2. The accommodating intraocular lens device of claim 1, wherein the inner surface faces the central cavity and comprises a plurality of spaced apart contact points configured to engage a portion of the peripheral edge of the power lens.

3. The accommodating intraocular lens device of claim 2, further comprising outer grooves disposed in the outer periphery opposite the inner surface contact points, wherein the outer grooves extend along at least a portion of the height of the haptic, and are configured to permit the haptic to be radially compressed, radially expanded, or both.

4. The accommodating intraocular lens device of claim 3, wherein the haptic further comprises a plurality of tabs extending radially inwardly into the central cavity and wherein the power lens is secured to the base assembly by the plurality of tabs.

5. The accommodating intraocular lens device of claim 4, wherein the haptic further comprises a plurality of tables extending radially inwardly into the central cavity and wherein a channel is formed between the plurality of tabs and the plurality of tables to secure the power lens to the base assembly.

6. The accommodating intraocular lens device of claim 4, wherein a bottom surface of the plurality of tabs is positioned at a distance of 0.75 mm to 1 mm from the first edge of the haptic.

7. The accommodating intraocular lens device of claim 4, wherein a bottom surface of the plurality of tabs is positioned at a distance, from the first edge of the haptic, of 38% to 75% of the height of the haptic.

8. The accommodating intraocular lens device of claim 7, further comprising a plurality of arms coupling the base lens to the haptic.

9. The accommodating intraocular lens device of claim 8, wherein the arms vault the base lens away from the central cavity.

10. The accommodating intraocular lens device of claim 8, wherein the first side of the power lens comprises a flexible membrane and wherein the second side of the power lens comprises an optic.

11. The accommodating intraocular lens device of claim 10, wherein the power lens further comprises:
    a membrane coupler extending radially inwardly from the peripheral edge to couple the flexible membrane with the peripheral edge; and
    an optic coupler disposed from the peripheral edge to couple the optic to the peripheral edge, wherein the optic coupler is angled to vault the optic toward the flexible membrane.

12. The accommodating intraocular lens device of claim 1, wherein:
    the first side of the power lens comprises a flexible membrane and the second side of the power lens comprises an optic;
    the outer periphery of the haptic is configured to engage a capsular bag of a patient's eye;
    the engaging contact enables external forces exerted on the outer periphery of the haptic to be radially transmitted to the peripheral edge of the power lens;
    the radially transmitted forces transmitted to the peripheral edge of the power lens cause the peripheral edge to be radially compressed; and
    the radially compressed peripheral edge causes a change in curvature of the flexible membrane without contact between the flexible membrane and the optic.

13. The accommodating intraocular lens device of claim 12, wherein, by virtue of pressure of the closed cavity, the change in curvature of the flexible membrane causes an axial displacement of the optic further away from the base lens.

14. The accommodating intraocular lens device of claim 1, wherein the first side of the power lens is configured to be positioned entirely within the cavity after being inserted into the eye.

15. An accommodating intraocular lens device comprising:
    a base assembly comprising a first open end, a second end comprising a base lens, and a haptic surrounding the base lens, the haptic comprising an outer periphery surrounding a cavity;
    a power lens sized to fit within the cavity, wherein a first side of the power lens comprises a flexible membrane and a second side of the power lens comprises an optic; and a retaining system spaced away from an edge of the cavity, extending radially inward, and positioned opposite the base lens along an optical axis and configured to secure the power lens within the cavity.

16. The accommodating intraocular lens device of claim 15, wherein the retaining system comprises a plurality of tabs extending radially inwardly from the haptic and into the cavity.

17. The accommodating intraocular lens device of claim 16, wherein the haptic is substantially circular.

18. The accommodating intraocular lens device of claim 17, wherein:
the outer periphery of the haptic is configured to engage a capsular bag of a patient's eye;
the engaging contact enables external forces exerted on the outer periphery of the haptic to be radially transmitted to the peripheral edge of the power lens;
the radially transmitted forces transmitted to the peripheral edge of the power lens cause the peripheral edge to be radially compressed; and
the radially compressed peripheral edge causes a change in curvature of the flexible membrane without contact between the flexible membrane and the optic.

19. The accommodating intraocular lens device of claim 18, wherein the change in curvature of the flexible membrane causes an axial displacement of the optic further away from the base lens.

20. The accommodating intraocular lens device of claim 19, wherein a bottom surface of the plurality of tabs is positioned at a distance, from a first edge of the haptic, of 38% to 75% of a height between the first edge and a second edge of the haptic.

21. An accommodating intraocular lens device comprising:
a base assembly comprising a first open end, a second end comprising a base lens, and a haptic surrounding the base lens, the haptic comprising an outer periphery surrounding the cavity;
a power lens comprising a circumferential peripheral portion comprising an anterior surface, a posterior surface, and a circumferential surface disposed between and transverse to the anterior surface and to the posterior surface, the power lens being sized to fit within the cavity; and
a retaining system comprising a C-shaped recess having a first surface configured to be placed in contact with the anterior surface of the circumferential portion and a second surface configured to be placed in contact with the posterior surface of the circumferential portion, the retaining system configured to secure the power lens within the cavity.

22. An accommodating intraocular lens device comprising:
a base assembly comprising a first open end, a second end comprising a base lens, and a haptic surrounding the base lens, the haptic comprising an outer periphery surrounding the cavity;
a power lens comprising a circumferential peripheral portion comprising an anterior surface, a posterior surface, and a circumferential surface disposed between and transverse to the anterior surface and to the posterior surface, the power lens being sized to fit within the cavity; and
a retaining system comprising a first radially inward projection and a second radially inward projection, the first radially inward projection having a posterior surface configured to be placed in contact with the anterior surface of the circumferential portion and an anterior surface spaced posteriorly from an anterior-most edge of the haptic at the circumferential position of the first radially inward projection, the second radially inward projection having an anterior surface configured to be placed in contact with the posterior surface of the circumferential portion, the retaining system configured to secure the power lens within the cavity.

23. An accommodating intraocular lens device comprising:
a base assembly comprising a first open end, a second end comprising a base lens, and a haptic surrounding the base lens, the haptic comprising an outer periphery surrounding the cavity;
a power lens comprising a flexible membrane, an optic, and a circumferential peripheral portion comprising an anterior surface adjacent to the flexible membrane, a posterior surface adjacent to the optic and a circumferential surface disposed between and transverse to the anterior surface and to the posterior surface, the anterior surface of the circumferential portion disposed posterior to an anterior-most portion of the flexible membrane, the power lens being sized to fit within the cavity; and
a retaining system configured to secure the power lens within the cavity.

* * * * *